US006795736B2

(12) United States Patent
Connelly et al.

(10) Patent No.: US 6,795,736 B2
(45) Date of Patent: Sep. 21, 2004

(54) ELECTROMAGNETIC INTERFERENCE IMMUNE TISSUE INVASIVE SYSTEM

(75) Inventors: Patrick R. Connelly, Rochester, NY (US); Wilson Greatbatch, Akron, NY (US); Victor Miller, Clarence, NY (US)

(73) Assignee: Biophan Technologies, Inc., West Henrietta, NY (US)

( * ) Notice: Subject to any disclaimer, the term of this patent is extended or adjusted under 35 U.S.C. 154(b) by 258 days.

(21) Appl. No.: 10/077,868

(22) Filed: Feb. 19, 2002

(65) Prior Publication Data

US 2002/0138112 A1 Sep. 26, 2002

Related U.S. Application Data

(60) Provisional application No. 60/269,817, filed on Feb. 20, 2001.

(51) Int. Cl.$^7$ ............................................... A61N 1/362
(52) U.S. Cl. .......................................................... 607/36
(58) Field of Search ........................ 607/1–156; 606/15, 606/108; 600/300–595

(56) References Cited

U.S. PATENT DOCUMENTS

| | | |
|---|---|---|
| 3,057,356 A | 10/1962 | Greatbatch |
| 3,478,746 A | 11/1969 | Greatbatch |
| 3,508,167 A | 4/1970 | Russell, Jr. |
| 3,669,095 A | 6/1972 | Kobayashi et al. |
| 3,686,958 A | 8/1972 | Porter et al. |
| 3,718,142 A | 2/1973 | Mulier |
| 3,789,667 A | 2/1974 | Porter et al. |
| 3,825,015 A | 7/1974 | Berkovits |
| 4,012,641 A | 3/1977 | Brickerd, Jr. et al. |
| 4,041,954 A | 8/1977 | Ohara |
| 4,050,004 A | 9/1977 | Greatbatch |
| 4,071,032 A | 1/1978 | Schulman |
| 4,091,818 A | 5/1978 | Brownlee et al. |
| 4,200,110 A | 4/1980 | Peterson et al. |
| 4,210,029 A | 7/1980 | Porter |
| 4,254,776 A | 3/1981 | Tanie et al. |
| 4,325,382 A | 4/1982 | Miodownik |
| 4,333,053 A | 6/1982 | Harrison et al. |
| 4,341,221 A | 7/1982 | Testerman |
| 4,379,262 A | 4/1983 | Young |
| 4,432,363 A | 2/1984 | Kakegawa |
| 4,450,408 A | 5/1984 | Tiemann |
| 4,476,870 A | 10/1984 | Peterson et al. |
| 4,491,768 A | 1/1985 | Slicker |
| 4,545,381 A | 10/1985 | Bournay, Jr. et al. |
| 4,611,127 A | 9/1986 | Ibrahim et al. |
| 4,677,471 A | 6/1987 | Takamura et al. |
| 4,686,964 A | 8/1987 | Yunoki et al. |
| 4,691,164 A | 9/1987 | Haragashira |
| 4,719,159 A | 1/1988 | Clark et al. |

(List continued on next page.)

FOREIGN PATENT DOCUMENTS

WO     WO0174241     10/2001

OTHER PUBLICATIONS

A. Jerwzewski et al.; "Development of an MRI–Compatible Catheter for Pacing the Heart: Initial In Vitro and In Vivo Results," JMRI, ISHRM (US), vol. 6 (No. 6), p. 948–949, (Jun. 14, 1996).

(List continued on next page.)

*Primary Examiner*—Scott M. Getzow
(74) *Attorney, Agent, or Firm*—Basch & Nickerson LLP

(57) ABSTRACT

An electromagnetic immune tissue invasive system includes a primary device housing. The primary device housing having a control circuit therein. A shielding is formed around the primary device housing to shield the primary device housing and any circuits therein from electromagnetic interference. A lead system transmits and receives signals between the primary device housing. The lead system is either a fiber optic system or an electrically shielded electrical lead system.

24 Claims, 58 Drawing Sheets

U.S. PATENT DOCUMENTS

| | | |
|---|---|---|
| 4,727,874 A | 3/1988 | Bowers et al. |
| 4,763,075 A | 8/1988 | Weigert |
| 4,784,461 A | 11/1988 | Abe et al. |
| 4,798,443 A | 1/1989 | Knipe et al. |
| 4,800,883 A | 1/1989 | Winstrom |
| 4,804,244 A | 2/1989 | Hasegawa et al. |
| 4,827,906 A | 5/1989 | Robicsek et al. |
| 4,827,934 A | 5/1989 | Ekwall |
| 4,858,610 A | 8/1989 | Callaghan et al. |
| 4,879,992 A | 11/1989 | Nishigaki et al. |
| 4,880,004 A | 11/1989 | Baker, Jr. et al. |
| 4,903,701 A | 2/1990 | Moore et al. |
| 4,911,525 A | 3/1990 | Hicks et al. |
| 4,930,521 A | 6/1990 | Metzger et al. |
| 4,934,785 A | 6/1990 | Mathis et al. |
| 4,987,897 A | 1/1991 | Funke |
| 4,991,590 A | 2/1991 | Shi |
| 5,010,888 A | 4/1991 | Jadvar et al. |
| 5,055,810 A | 10/1991 | de La Chapelle et al. |
| 5,058,586 A | 10/1991 | Heinze |
| 5,061,680 A | 10/1991 | Paulson et al. |
| 5,089,697 A | 2/1992 | Prohaska |
| 5,113,859 A | 5/1992 | Funke |
| 5,131,409 A | 7/1992 | Lobarev et al. |
| 5,154,387 A | 10/1992 | Trailer |
| 5,158,932 A | 10/1992 | Hinshaw et al. |
| 5,168,871 A | 12/1992 | Grevious |
| 5,178,149 A | 1/1993 | Imburgia et al. |
| 5,214,730 A | 5/1993 | Nagasawa et al. |
| 5,217,009 A | 6/1993 | Kronberg |
| 5,217,010 A | 6/1993 | Tsitlik et al. |
| 5,226,210 A | 7/1993 | Koskenmaki et al. |
| 5,240,004 A | 8/1993 | Walinsky et al. |
| 5,243,979 A | 9/1993 | Stein et al. |
| 5,265,602 A | 11/1993 | Anderson et al. |
| 5,267,564 A | 12/1993 | Barcel et al. |
| 5,324,310 A | 6/1994 | Greeninger et al. |
| 5,330,512 A | 7/1994 | Hauck et al. |
| 5,348,010 A | 9/1994 | Schnall et al. |
| 5,354,220 A | 10/1994 | Ganguly et al. |
| 5,370,668 A | 12/1994 | Shelton et al. |
| 5,387,229 A | 2/1995 | Poore |
| 5,387,232 A | 2/1995 | Trailer |
| 5,402,070 A | 3/1995 | Shelton et al. |
| 5,410,413 A | 4/1995 | Sela |
| 5,415,653 A | 5/1995 | Wardle et al. |
| 5,425,373 A | 6/1995 | Causey, III |
| 5,435,308 A | 7/1995 | Gallup et al. |
| 5,435,316 A | 7/1995 | Kruse |
| 5,438,987 A | 8/1995 | Thacker et al. |
| 5,445,151 A | 8/1995 | Darrow et al. |
| 5,453,838 A | 9/1995 | Danielian et al. |
| 5,454,837 A | 10/1995 | Lindegren et al. |
| 5,456,698 A | 10/1995 | Byland et al. |
| 5,464,014 A | 11/1995 | Sugahara |
| 5,476,095 A | 12/1995 | Schnall et al. |
| 5,520,190 A | 5/1996 | Benedict et al. |
| 5,523,534 A | 6/1996 | Meister et al. |
| 5,569,158 A | 10/1996 | Suzuki et al. |
| 5,570,671 A | 11/1996 | Hickey |
| 5,574,811 A | 11/1996 | Bricheno et al. |
| 5,575,772 A | 11/1996 | Lennox |
| 5,582,170 A | 12/1996 | Soller |
| 5,590,227 A | 12/1996 | Osaka et al. |
| 5,601,611 A | 2/1997 | Fayram et al. |
| 5,603,697 A | 2/1997 | Grundy et al. |
| 5,604,433 A | 2/1997 | Theus et al. |
| 5,611,016 A | 3/1997 | Fangmann et al. |
| 5,619,605 A | 4/1997 | Ueda et al. |
| 5,626,618 A | 5/1997 | Ward et al. |
| 5,626,619 A | 5/1997 | Jacobson et al. |
| 5,631,988 A | 5/1997 | Swirhun et al. |
| 5,634,720 A | 6/1997 | Gallup et al. |
| 5,649,965 A | 7/1997 | Pons et al. |
| 5,653,735 A | 8/1997 | Chen et al. |
| 5,654,317 A | 8/1997 | Fujioka et al. |
| 5,658,966 A | 8/1997 | Tsukamoto et al. |
| 5,679,026 A | 10/1997 | Fain et al. |
| 5,683,435 A | 11/1997 | Truex et al. |
| 5,697,958 A | 12/1997 | Paul et al. |
| 5,699,801 A | 12/1997 | Atalar et al. |
| 5,709,225 A | 1/1998 | Budgifvars et al. |
| 5,716,386 A | 2/1998 | Ward et al. |
| 5,723,856 A | 3/1998 | Yao et al. |
| 5,733,247 A | 3/1998 | Fallon |
| 5,738,105 A | 4/1998 | Kroll |
| 5,749,910 A | 5/1998 | Brumwell et al. |
| 5,752,977 A | 5/1998 | Grevious et al. |
| 5,755,739 A | 5/1998 | Sun et al. |
| 5,755,742 A | 5/1998 | Schuelke et al. |
| 5,759,197 A | 6/1998 | Sawchuk et al. |
| 5,761,354 A | 6/1998 | Kuwano et al. |
| 5,766,227 A | 6/1998 | Nappholz et al. |
| 5,772,604 A | 6/1998 | Langberg et al. |
| 5,774,501 A | 6/1998 | Halpern et al. |
| 5,776,167 A | 7/1998 | Levine et al. |
| 5,776,168 A | 7/1998 | Gunderson |
| 5,782,241 A | 7/1998 | Felblinger et al. |
| 5,782,880 A | 7/1998 | Lahtinen et al. |
| 5,808,730 A | 9/1998 | Danielian et al. |
| 5,814,087 A | 9/1998 | Renirie |
| 5,814,089 A | 9/1998 | Stokes et al. |
| 5,814,090 A | 9/1998 | Latterell et al. |
| 5,814,091 A | 9/1998 | Dahlberg et al. |
| 5,817,130 A | 10/1998 | Cox et al. |
| 5,817,133 A | 10/1998 | Houben |
| 5,817,136 A | 10/1998 | Nappholz et al. |
| 5,818,990 A | 10/1998 | Steijer et al. |
| 5,827,195 A | 10/1998 | Lander |
| 5,827,997 A | 10/1998 | Chung et al. |
| 5,830,209 A | 11/1998 | Savage et al. |
| 5,836,895 A | 11/1998 | Ramsey, III |
| 5,861,012 A | 1/1999 | Stroebel |
| 5,865,839 A | 2/1999 | Doorish |
| 5,867,361 A | 2/1999 | Wolf et al. |
| 5,868,664 A | 2/1999 | Speier et al. |
| 5,869,412 A | 2/1999 | Yenni, Jr. et al. |
| 5,870,272 A | 2/1999 | Seifried et al. |
| 5,871,509 A | 2/1999 | Noren |
| 5,871,512 A | 2/1999 | Hemming et al. |
| 5,873,898 A | 2/1999 | Hemming et al. |
| 5,882,108 A | 3/1999 | Fraizer |
| 5,882,305 A | 3/1999 | Dumoulin et al. |
| 5,891,171 A | 4/1999 | Wickham |
| 5,895,980 A | 4/1999 | Thompson |
| 5,897,577 A | 4/1999 | Cinbis et al. |
| 5,899,927 A | 5/1999 | Ecker et al. |
| 5,902,326 A | 5/1999 | Lessar et al. |
| 5,916,162 A | 6/1999 | Snelten et al. |
| 5,916,237 A | 6/1999 | Schu |
| 5,917,625 A | 6/1999 | Ogusu et al. |
| 5,919,135 A | 7/1999 | Lemelson |
| 5,928,145 A | 7/1999 | Ocali et al. |
| 5,928,270 A | 7/1999 | Ramsey, III |
| 5,928,570 A | 7/1999 | Reo |
| 5,940,554 A | 8/1999 | Chang et al. |
| 5,946,086 A | 8/1999 | Bruce |
| 5,951,596 A | 9/1999 | Bellinger |
| 5,954,660 A | 9/1999 | Legay et al. |
| 5,957,857 A | 9/1999 | Hartley |
| 5,963,034 A | 10/1999 | Mahapatra et al. |

| | | |
|---|---|---|
| 5,963,690 A | 10/1999 | Cheng |
| 5,967,977 A | 10/1999 | Mullis et al. |
| 5,968,083 A | 10/1999 | Ciciarelli et al. |
| 5,973,779 A | 10/1999 | Ansari et al. |
| 5,973,906 A | 10/1999 | Stevenson et al. |
| 5,978,710 A | 11/1999 | Prutchi et al. |
| 5,982,961 A | 11/1999 | Pan et al. |
| 5,985,129 A | 11/1999 | Gough et al. |
| 5,987,995 A | 11/1999 | Sawatari et al. |
| 5,999,853 A | 12/1999 | Stoop et al. |
| 5,999,857 A | 12/1999 | Weijand et al. |
| 6,005,191 A | 12/1999 | Tzeng et al. |
| 6,011,994 A | 1/2000 | Kronberg |
| 6,013,376 A | 1/2000 | Yenni, Jr. |
| 6,016,448 A | 1/2000 | Busacker et al. |
| 6,016,477 A | 1/2000 | Ehnebuske et al. |
| 6,023,641 A | 2/2000 | Thompson |
| 6,024,738 A | 2/2000 | Daikuzono et al. |
| 6,026,316 A | 2/2000 | Kucharczyk et al. |
| 6,029,086 A | 2/2000 | Kim et al. |
| 6,029,087 A | 2/2000 | Wohlgemuth |
| 6,031,710 A | 2/2000 | Wolf et al. |
| 6,036,639 A | 3/2000 | Allred, III et al. |
| 6,036,654 A | 3/2000 | Quinn et al. |
| 6,044,301 A | 3/2000 | Hartlaub et al. |
| 6,052,613 A | 4/2000 | Takaki |
| 6,052,614 A | 4/2000 | Morris, Sr. et al. |
| 6,052,623 A | 4/2000 | Fenner et al. |
| 6,055,455 A | 4/2000 | O'Phelan et al. |
| 6,056,415 A | 5/2000 | Allred, III et al. |
| 6,056,721 A | 5/2000 | Shulze |
| 6,064,906 A | 5/2000 | Langberg et al. |
| 6,066,096 A | 5/2000 | Smith et al. |
| 6,067,472 A | 5/2000 | Vonk et al. |
| 6,076,003 A | 6/2000 | Rogel |
| 6,080,829 A | 6/2000 | Tapsak et al. |
| 6,090,473 A | 7/2000 | Yoshikawa et al. |
| 6,090,728 A | 7/2000 | Yenni, Jr. et al. |
| 6,091,015 A | 7/2000 | del Valle et al. |
| 6,091,744 A | 7/2000 | Sorin et al. |
| 6,091,987 A | 7/2000 | Thompson |
| 6,101,973 A | 8/2000 | Stewart et al. |
| 6,118,910 A | 9/2000 | Chang |
| 6,119,031 A | 9/2000 | Crowley |
| 6,129,745 A | 10/2000 | Sun et al. |
| 6,134,003 A | 10/2000 | Tearney et al. |
| 6,134,478 A | 10/2000 | Spehr |
| 6,142,678 A | 11/2000 | Cheng |
| 6,144,205 A | 11/2000 | Souza et al. |
| 6,144,866 A | 11/2000 | Miesel et al. |
| 6,144,881 A | 11/2000 | Hemming et al. |
| 6,146,415 A | 11/2000 | Fitz |
| 6,148,222 A | 11/2000 | Ramsey, III |
| 6,148,229 A | 11/2000 | Morris, Sr. et al. |
| 6,149,313 A | 11/2000 | Giebel et al. |
| 6,163,724 A | 12/2000 | Hemming et al. |
| 6,166,806 A | 12/2000 | Tjin |
| 6,169,921 B1 | 1/2001 | Ken Knight et al. |
| 6,171,240 B1 | 1/2001 | Young et al. |
| 6,173,203 B1 | 1/2001 | Barkley et al. |
| 6,179,482 B1 | 1/2001 | Takizawa et al. |
| 6,188,926 B1 | 2/2001 | Vock |
| 6,192,261 B1 | 2/2001 | Gratton et al. |
| 6,198,968 B1 | 3/2001 | Prutchi et al. |
| 6,198,972 B1 | 3/2001 | Hartlaub et al. |
| 6,208,899 B1 | 3/2001 | Kroll |
| 6,216,041 B1 | 4/2001 | Tierney et al. |
| 6,223,083 B1 | 4/2001 | Rosar |
| 6,226,545 B1 | 5/2001 | Gilderdale |
| 6,230,060 B1 | 5/2001 | Mawhinney |
| 6,236,879 B1 | 5/2001 | Konings |
| 6,238,686 B1 | 5/2001 | Burrell et al. |
| 6,240,317 B1 | 5/2001 | Villaseca et al. |
| 6,245,020 B1 | 6/2001 | Moore et al. |
| 6,246,910 B1 | 6/2001 | Bonnet et al. |
| 6,247,474 B1 | 6/2001 | Greeninger et al. |
| 6,254,632 B1 | 7/2001 | Wu et al. |
| 6,256,537 B1 | 7/2001 | Stoop et al. |
| 6,256,541 B1 | 7/2001 | Heil et al. |
| 6,258,087 B1 | 7/2001 | Edwards et al. |
| 6,259,843 B1 | 7/2001 | Kondo |
| 6,259,954 B1 | 7/2001 | Conger et al. |
| 6,263,229 B1 | 7/2001 | Atalar et al. |
| 6,263,242 B1 | 7/2001 | Mika et al. |
| 6,266,555 B1 | 7/2001 | Werner et al. |
| 6,266,563 B1 | 7/2001 | Ken Knight et al. |
| 6,266,564 B1 | 7/2001 | Hill et al. |
| 6,266,566 B1 | 7/2001 | Nichols et al. |
| 6,270,457 B1 | 8/2001 | Bardy |
| 6,270,831 B2 | 8/2001 | Kumar et al. |
| 6,272,377 B1 | 8/2001 | Sweeney et al. |
| 6,272,380 B1 | 8/2001 | Warman et al. |
| 6,274,265 B1 | 8/2001 | Kraska et al. |
| 6,275,730 B1 | 8/2001 | Ken Knight et al. |
| 6,275,732 B1 | 8/2001 | Hsu et al. |
| 6,275,734 B1 | 8/2001 | McClure et al. |
| 6,277,078 B1 | 8/2001 | Porat et al. |
| 6,277,107 B1 | 8/2001 | Lurie et al. |
| 6,278,057 B1 | 8/2001 | Avellanet |
| 6,278,277 B1 | 8/2001 | Zeiger |
| 6,278,894 B1 | 8/2001 | Salo et al. |
| 6,278,897 B1 | 8/2001 | Rutten et al. |
| 6,296,654 B1 | 10/2001 | Ward |
| 6,317,633 B1 | 11/2001 | Jorgenson et al. |
| 6,367,984 B1 | 4/2002 | Stephenson et al. |

OTHER PUBLICATIONS

W. Moshage et al., "A Non–Magnetic, MRI Compatible Pacing Center for Clinical Application in Magnetocardiography," Biomedizinixche Technik Band, Erganzungsband (Germany), p. 162–163,(Jun. 14, 1990).

C. Roos, et al., "Fiber Optic Pressure Transducer for Use Near MR Magnetic Fields," RSNA 1985; one page.

K. Wickersheim et al., "Fiberoptic Thermometry and its Applications," J. Microwave Power (1987); pp. 85–94.

Mark B. M. Hofman; "MRI–Compatible Cardiac Pacing Catheter," JMRI; May/Jun. 1997; p. 612.

A.A. Damji et al., "RF Interference Suppression in a Cardiac Synchronization System Operating in High Magnetic Field NMR Imaging System," Magnetic Resonance Imaging, vol. 6, pp 637–640, (1988).

Frank G. Shellock et al., "Burns Associated with the use of Monitoring Equipment during MR Procedures," JMRI, Jan./Feb. 1996; pp. 271–272.

J. Nyenhuis et al., "Heating Near Implanted Medical Devices by the MRI RF–Magnetic Field," IEEE Trans. Mag.; Sep. 1999; four pages.

Frank Shellock et al., "Cardiovascular Catheters and Accessories: Ex Vivo Testing of Ferromagnetism, Heating, and Artifacts Associated with MRI," JMRI, Nov./Dec. 1998, vol. 8 #6; pp, 1338–1342.

J. Rod Gimbel et al., "Safe Performance of magnetic REsonance," Pace; vol. 19; Jun. 1996; pp. 913–919.

National Library of Medicine; "Rapid Ventricular Pacing in a Pacemaker Patient Undergoing Magnetic Resonance Imaging," Pub Med; Pacing Clin Electrophysiol; Jun. 1998; p. 1.

National Library of Medicine;"Effects of Magnetic Resonance Imaging on Cardiac Pacemakers and Electrodes," Pub Med; Am Heart J; (1997); pp. 1–2.

M. Kusumoto et al., "Cardiac Pacing for the Clinician," Lippincott Williams & Wilkins; (2001); Chapter 1, pp. 9, 12, 13, 18, 22, 24.

Donald Fink; "Electronic Engineering," Electronic Engineers Handbook; 2nd edition, Mcgraw Hill; (1982); Section 14; pp. 29–45.

X Luo et al., "Electromagnetic Interference Shielding Using Continuous Carbon–Fiber Carbon–Matrix and Polymer–Matrix Composites," Composites Part B: Engineering; (1999); pp. 227–231.

D.D.L. Chung, "Flexible Graphite for Gasketing, Absorption, Electromagnetic Interference Shielding, Vibration Damping, Electrochemical Applications, and Stress Sensing," Journal of Materials Engineering and Performance; Apr. 2000; vol. 9, p. 161–163.

M. Konings et al., "Catheters and Guidewires in Interventional MRI: Problems and Solutions," Medical Mundi; 45/1; Mar. (2001).

M. Konings; "Development of an MR–Safe Tracking Catheter with a Laser DrivenTip Coil," Journal of Magnetic Resonance Imaging 2001:13:131–135. c. Wiley–Liss, Inc.

Ey Young et al., "An Optical System for Wireles Detuning of Parallel Resonant Circuits" Journal of Magnetic Resonance Imaging;(2000); vol. 12, pp. 632–638.

Bernd Nowak; "Taking Advantage of Sophisticated Pacemaker Diagnostics," Excerpta Medica; (1999); pp. 172D–179D.

Jose A. Jogler et al., "Interaction of a Commercial Heart Rate Monitor With Implanted Pacemakers," Excerpta Medica; (1999); pp. 790–792.

J.A. Pomposo et al., "Polypyrrole–based Conducting Hot Melt Adhesives for EMI Shielding Applications," Elsevier; Synthetic Metals 104;(1999); pp. 107–111.

K. Grattan et al., "Fiber Optic Sensor Technology: An Overview," Elsevier; Sensors and Actuators 82; (2000);pp. 40–61.

L. Rippert et al., "Optical andn Acoustic Damage Detection in Laminated CFRP Composite Materials," Elsevier; Composites Science and Technology 60; (2000); pp. 2713–2724.

C. Strandman et al., "A Production Process of Silicon Sensor Elements for a Fibre–Optic Pressure Sensor," Elsevier; Sensors and Actuators A63; (1997); pp. 69–74.

D. Howard et al., "A Single–Fringe Etalon Silicon Pressure Transducer," Elsevier; Sensors and Actuators 86; (2000); pp. 21–25.

Dan Haronian, "Displacement Sensing Using Geometrical Modulation in Reflection Mode (GM–RM) of Coupled Optical Waveguides," J. Micromech, Microeng., (UK), (1998); pp. 323–326.

H Ghafouri–Shiraz, "A Novel Distributed Feedback Laser Diode Structure foran Optical Wavelength Tunable Filter," Semicond. Sci. Technol. 12; (UK), (1997); pp. 1161–1165.

L. Kasarian, "A New Optical Fiber Multiplexer for Distortim–Gree LIght Transfer in Multichannel fiber Optic Sensor Systems," Elsevier; Sensors and Actuators 84; (2000); pp. 250–258.

X. Yan et al., "Electric Field Controlled 2x2 Bypass Exchange Photorefractive Switch," IOP Publishing; (UK) (1998), pp. 383–386.

E. Piener et al., "A Micromachined Vibration Sensor Based on the Control of Power Transmitted Between Optical Fibres," Elsevier; Sensors and Actuators A65; (1998) pp. 23–29.

Engin Molva; "Microchip Lasers and Their Applications in Optical Microsystems," Elsevier; Optical Materials 11; (1999); pp. 289–299.

D. Sun et al., "High Performance Unidirectional Electrooptic Modulator Based On Polymeric Highly Multi–Mode Waveguides,"Elsevier; Optics & Laser Technology 30; (1998); 481–489.

Engin Molva; "Microchip Lasers and Their Applications in Optical Microsystems," Elsevier; Optical Materials 11; (1999); pp. 289–299.

J. Linares et al., "Theory and Design of an Integrated Optical Sensor Based on Planar Waveguiding Lenses," Elsevier; Optics Communications 180; (2000); pp. 29–36.

O. Parriaux et al., "Coupling Gratings as Waveguide Functional Elements," IOP Publishing; Pure Appl. Opt. 5; (1996); pp. 453–469.

E T Enikov et al., "Three–Dimensional Microfabrication for a Multi–Degree of Freedom Capacitive Force Sensor Using Fibre–Chip Coupling" IOP Publishing; (UK); J. Micromechl. Microeng. 10;(2000) pp. 492–497.

J. Holm et al., "Through–Etched Silicon Carriers for Passive Alighnment of Optical Fibers to Surface–Active Optoelectronic Components" Elsevier;Sensors and Actuators 82; (2000) pp. 245–248.

M. Kimura et al., "Vibration Sensor Using Optical–Fiber Catilever with Bulb–Lens" Elsevier; Sensors and Actuators A66; (2000) pp. 178–183.

Y. Mao et al., "Three–Stage Wavelength Converter Based on Cross–Grain Modulation in Semiconductor Optical Amplifiers" Elsevier; Optics Communications 167: (1999) pp. 57–66.

X. Hu et al., "Dynamically Induced Irreversibility: Light Amplification and Wuantum Noise Reduction in a V–Type Three–Level System" IOP Publshing; J. Opt. B: Quantum Semiclass. Opt. 2; (UK) (2000); pp. 570–575.

Y. Yim et al., "Lithium Niobate Integrated–Optic Voltage Snsorwith Variable Sensing Ranges" Elsevier; Optics Communications 152; Jul. 1, 1998; pp. 225–228.

C. Lee et al., "Electromagnetic Interference Shilding Efficiency of Polyaniline Mixtures and Multilayer Films"0 Elsevier; Synthetic Metals 102; (1999) pp. 1346–1349.

Marc Desmulliez, "Optoelectronics–VLSI System Integration Technological Challenges" Elsevier; Materials Science and Engineering B74;(2000) pp. 269–275.

J. Zook et al., "Fiber–optic Vibration Sensor Based on Frequency Modulation of Light–Excited Oscillators" Elsevier; Sensors and Actuators 83; (2000); pp. 270–276.

M. Reta–Hernandez et al., "Attenuation of Low Frequency Magnetic Fields Using Active Shielding" Elsevier; Electric Power Systems Research 45; (1998); pp. 57–63.

C. Huang et al., "The EMI Shielding Effectiveness of PC/ABS/Nickel–Coated Carbon–Fibre COmposites" Elsevier; European Polymer Journal 36; (2000) pp. 2727–2737.

ELECTROMAGNETIC INTERFERENCE IMMUNE TISSUE INVASIVE SYSTEM

PRIORITY INFORMATION

This application claims priority from U.S. Provisional Patent Application, Serial No. 60/269,817, filed on Feb. 20, 2001; the entire contents of which are hereby incorporated by reference.

CROSS REFERENCE TO RELATED PATENT APPLICATIONS

The subject matter of co-pending U.S. patent application Ser. No. 09/885,867, filed on Jun. 20, 2001, entitled "Controllable, Wearable MRI-Compatible Cardiac Pacemaker With Pulse Carrying Photonic Catheter And VOO Functionality"; co-pending U.S. patent application Ser. No. 09/885,868, filed on Jun. 20, 2001, entitled "Controllable, Wearable MRI-Compatible Cardiac Pacemaker With Power Carrying Photonic Catheter And VOO Functionality"; co-pending U.S. patent application Ser. No. 10/037,513, filed on Jan. 4, 2002, entitled "Optical Pulse Generator For Battery Powered Photonic Pacemakers And Other Light Driven Medical Stimulation Equipment"; co-pending U.S. patent application Ser. No. 10/037,720, filed on Jan. 4, 2002, entitled "Opto-Electric Coupling Device For Photonic Pacemakers And Other OptoElectric Medical Stimulation Equipment"; co-pending U.S. patent application Ser. No. 09/943,216, filed on Aug. 30, 2001, entitled "Pulse width Cardiac Pacing Apparatus"; co-pending U.S. patent application Ser. No. 09/964,095, filed on Sep. 26, 2001, entitled "Process for Converting Light"; and co-pending U.S. patent application Ser. No. 09/921,066, filed on Aug. 2, 2001, entitled "MRI-Resistant Implantable Device". The entire contents of each of the above noted co-pending U.S. patent applications (Ser. Nos.: 09/885,867; 09/885,868; 10/037,513; 10/037,720; 09/943,216; 09/964,095; and 09/921,066) are hereby incorporated by reference.

FIELD OF THE PRESENT INVENTION

The present invention relates generally to an implantable device that is immune or hardened to electromagnetic insult or interference. More particularly, the present invention is directed to implantable systems that utilize fiber optic leads and other components to hardened or immune the systems from electromagnetic insult, namely magnetic-resonance imaging insult.

BACKGROUND OF THE PRESENT INVENTION

Magnetic resonance imaging ("MRI") has been developed as an imaging technique adapted to obtain both images of anatomical features of human patients as well as some aspects of the functional activities of biological tissue. These images have medical diagnostic value in determining the state of the health of the tissue examined.

In an MRI process, a patient is typically aligned to place the portion of the patient's anatomy to be examined in the imaging volume of the MRI apparatus. Such an MRI apparatus typically comprises a primary magnet for supplying a constant magnetic field ($B_0$) which, by convention, is along the z-axis and is substantially homogeneous over the imaging volume and secondary magnets that can provide linear magnetic field gradients along each of three principal Cartesian axes in space (generally x, y, and z, or $x_1$, $X_2$ and $X_3$, respectively). A magnetic field gradient ($\Delta B_0/\Delta x_1$) refers to the variation of the field along the direction parallel to $B_0$ with respect to each of the three principal Cartesian axes, $x_1$. The apparatus also comprises one or more RF (radio frequency) coils which provide excitation and detection of the MRI signal.

The use of the MRI process with patients who have implanted medical assist devices; such as cardiac assist devices or implanted insulin pumps; often presents problems. As is known to those skilled in the art, implantable devices (such as implantable pulse generators (IPGs) and cardioverter/defibrillator/pacemakers (CDPs)) are sensitive to a variety of forms of electromagnetic interference (EMI) because these enumerated devices include sensing and logic systems that respond to low-level electrical signals emanating from the monitored tissue region of the patient. Since the sensing systems and conductive elements of these implantable devices are responsive to changes in local electromagnetic fields, the implanted devices are vulnerable to external sources of severe electromagnetic noise, and in particular, to electromagnetic fields emitted during the magnetic resonance imaging (MRI) procedure. Thus, patients with implantable devices are generally advised not to undergo magnetic resonance imaging (MRI) procedures.

To more appreciate the problem, the use of implantable cardiac assist devices during a MRI process will be briefly discussed.

The human heart may suffer from two classes of rhythmic disorders or arrhythmias: bradycardia and tachyarrhythmia. Bradycardia occurs when the heart beats too slowly, and may be treated by a common implantable pacemaker delivering low voltage (about 3 V) pacing pulses.

The common implantable pacemaker is usually contained within a hermetically sealed enclosure, in order to protect the operational components of the device from the harsh environment of the body, as well as to protect the body from the device.

The common implantable pacemaker operates in conjunction with one or more electrically conductive leads, adapted to conduct electrical stimulating pulses to sites within the patient's heart, and to communicate sensed signals from those sites back to the implanted device.

Furthermore, the common implantable pacemaker typically has a metal case and a connector block mounted to the metal case that includes receptacles for leads which may be used for electrical stimulation or which may be used for sensing of physiological signals. The battery and the circuitry associated with the common implantable pacemaker are hermetically sealed within the case. Electrical interfaces are employed to connect the leads outside the metal case with the medical device circuitry and the battery inside the metal case.

Electrical interfaces serve the purpose of providing an electrical circuit path extending from the interior of a hermetically sealed metal case to an external point outside the case while maintaining the hermetic seal of the case. A conductive path is provided through the interface by a conductive pin that is electrically insulated from the case itself.

Such interfaces typically include a ferrule that permits attachment of the interface to the case, the conductive pin, and a hermetic glass or ceramic seal that supports the pin within the ferrule and isolates the pin from the metal case.

A common implantable pacemaker can, under some circumstances, be susceptible to electrical interference such that the desired functionality of the pacemaker is impaired. For example, common implantable pacemaker requires protection against electrical interference from electromagnetic interference (EMI), defibrillation pulses, electrostatic discharge, or other generally large voltages or currents generated by other devices external to the medical device. As noted above, more recently, it has become crucial that cardiac assist systems be protected from magnetic-resonance imaging sources.

Such electrical interference can damage the circuitry of the cardiac assist systems or cause interference in the proper operation or functionality of the cardiac assist systems. For example, damage may occur due to high voltages or excessive currents introduced into the cardiac assist system.

Therefore, it is required that such voltages and currents be limited at the input of such cardiac assist systems, e.g., at the interface. Protection from such voltages and currents has typically been provided at the input of a cardiac assist system by the use of one or more zener diodes and one or more filter capacitors.

For example, one or more zener diodes may be connected between the circuitry to be protected, e.g., pacemaker circuitry, and the metal case of the medical device in a manner which grounds voltage surges and current surges through the diode(s). Such zener diodes and capacitors used for such applications may be in the form of discrete components mounted relative to circuitry at the input of a connector block where various leads are connected to the implantable medical device, e.g., at the interfaces for such leads.

However, such protection, provided by zener diodes and capacitors placed at the input of the medical device, increases the congestion of the medical device circuits, at least one zener diode and one capacitor per input/output connection or interface. This is contrary to the desire for increased miniaturization of implantable medical devices.

Further, when such protection is provided, interconnect wire length for connecting such protection circuitry and pins of the interfaces to the medical device circuitry that performs desired functions for the medical device tends to be undesirably long. The excessive wire length may lead to signal loss and undesirable inductive effects. The wire length can also act as an antenna that conducts undesirable electrical interference signals to sensitive CMOS circuits within the medical device to be protected.

Additionally, the radio frequency (RF) energy that is inductively coupled into the wire causes intense heating along the length of the wire, and at the electrodes that are attached to the heart wall. This heating may be sufficient to ablate the interior surface of the blood vessel through which the wire lead is placed, and may be sufficient to cause scarring at the point where the electrodes contact the heart. A further result of this ablation and scarring is that the sensitive node that the electrode is intended to pace with low voltage signals becomes desensitized, so that pacing the patient's heart becomes less reliable, and in some cases fails altogether.

Another conventional solution for protecting the implantable medical device from electromagnetic interference is illustrated in FIG. 1. FIG. 1 is a schematic view of an implantable medical device 12 embodying protection against electrical interference. At least one lead 14 is connected to the implantable medical device 12 in connector block region 13 using an interface.

In the case where implantable medical device 12 is a pacemaker implanted in a body 10, the pacemaker 12 includes at least one or both of pacing and sensing leads represented generally as leads 14 to sense electrical signals attendant to the depolarization and repolarization of the heart 16, and to provide pacing pulses for causing depolarization of cardiac tissue in the vicinity of the distal ends thereof.

FIG. 2 more particularly illustrates the circuit that is used conventionally to protect from electromagnetic interference. As shown in FIG. 2, protection circuitry 15 is provided using a diode array component 30. The diode array consists of five zener diode triggered semiconductor controlled rectifiers (SCRs) with anti-parallel diodes arranged in an array with one common connection. This allows for a small footprint despite the large currents that may be carried through the device during defibrillation, e.g., 10 amps. The SCRs 20–24 turn on and limit the voltage across the device when excessive voltage and current surges occur.

As shown in FIG. 2, each of the zener diode triggered SCRs 20–24 is connected to an electrically conductive pin 25–26, 28, 29, respectively. Further, each electrically conductive pin 25, 26, 28, 29 is connected to a medical device contact region 31, 32, 34, 35 to be wire bonded to pads of a printed circuit board. The diode array component 30 is connected to the electrically conductive pins 25, 26, 28, 29 via the die contact regions respectively, along with other electrical conductive traces of the printed circuit board.

Other attempts have been made to protect implantable devices from MRI fields. For example, U.S. Pat. No. 5,968, 083 (to Ciciarelli et al.) describes a device adapted to switch between low and high impedance modes of operation in response to EMI insult. Furthermore, U.S. Pat. No. 6,188, 926 (to Vock) discloses a control unit for adjusting a cardiac pacing rate of a pacing unit to an interference backup rate when heart activity cannot be sensed due to EMI.

Although, conventional medical devices provide some means for protection against electromagnetic interference, these conventional devices require much circuitry and fail to provide fail-safe protection against radiation produced by magnetic-resonance imaging procedures. Moreover, the conventional devices fail to address the possible damage that can be done at the tissue interface due to RF-induced heating, and they fail to address the unwanted heart stimulation that may result from RF-induced electrical currents.

Thus, it is desirable to provide protection against electromagnetic interference, without requiring much circuitry and to provide fail-safe protection against radiation produced by magnetic-resonance imaging procedures. Moreover, it is desirable to provide devices that prevent the possible damage that can be done at the tissue interface due to induced electrical signals and due to thermal tissue damage. Furthermore, it is desirable to provide to provide an effective means for transferring energy from one point in the body to another point without having the energy causing a detrimental effect upon the body.

SUMMARY OF THE PRESENT INVENTION

A first aspect of the present invention is a cardiac assist system. The cardiac assist system includes a primary device housing; the primary device housing having a control circuit therein; a shielding formed around the primary device housing to shield the primary device housing and any circuits therein from electromagnetic interference; and a lead system to transmit and receive signals between a heart and the primary device housing.

A second aspect of the present invention is a cardiac assist system. The cardiac assist system includes a primary device housing; the primary device housing having a control circuit therein; a lead system to transmit and receive signals between a heart and the primary device housing; and a detection circuit, located in the primary device housing, to detect an electromagnetic interference insult upon the cardiac assist system. The control circuit places the cardiac assist system in an a synchronous mode upon detection of the electromagnetic interference insult by the detection system.

A third aspect of the present invention is a cardiac assist system. The cardiac assist system includes a primary device housing; the primary device housing having a control circuit therein; a shielding formed around the primary device housing to shield the primary device housing and any circuits therein from electromagnetic interference; a fiber optic based lead system to receive signals at the primary housing from a heart; and an electrical based lead system to transmit signals to the heart from the primary device housing.

A fourth aspect of the present invention is a cardiac assist system. The cardiac assist system includes a primary device housing; the primary device housing having a control circuit therein; a shielding formed around the primary device housing to shield the primary device housing and any circuits therein from electromagnetic interference; and a fiber optic based lead system to receive signals at the primary housing from a heart and to transmit signals to the heart from the primary device housing.

A fifth aspect of the present invention is a cardiac assist system for implanting in a body of a patient, the cardiac assist system comprising; a main module; a magnetic-resonance imaging-immune auxiliary module; a communication channel between the main module and the magnetic-resonance imaging-immune auxiliary module for the magnetic-resonance imaging-immune auxiliary module to detect failure of the main module; and controller for activating the magnetic-resonance imaging-immune auxiliary module upon detection of failure of the main module.

A sixth aspect of the present invention is a cardiac assist system. The cardiac assist system includes a primary device housing including a power supply and a light source; the primary device housing having a control circuit therein; a shielding formed around the primary device housing to shield the primary device housing and any circuits therein from electromagnetic interference; a cardiac assist device associated with a heart; and a photonic lead system to transmit between the primary device housing and the cardiac assist device, both power and control signals in the form of light.

A further aspect of the present invention is a cardiac assist system. The cardiac assist system includes a primary device housing; the primary device housing having a first control circuit, therein, to perform synchronous cardiac assist operations; a secondary device housing having a second control circuit therein, to perform asynchronous cardiac assist operations; and a detection circuit, communicatively coupled to the first and second control circuits, to detect an electromagnetic interference insult upon the cardiac assist system. The first control circuit terminates synchronous cardiac assist operations and the second control circuit initiates asynchronous cardiac assist operations upon detection of the electromagnetic interference insult by the detection system.

A further aspect of the present invention is an implantable cable for transmission of a signal to and from a body tissue of a vertebrate. The implantable cable includes a fiber optic bundle having a surface of non-immunogenic, physiologically compatible material, the fiber optic bundle being capable of being permanently implanted in a body cavity or subcutaneously, the fiber optic bundle having a distal end for implantation at or adjacent to the body tissue and a proximal end. The proximal end is adapted to couple to and direct an optical signal source; the distal end is adapted to couple to an optical stimulator. The fiber optic bundle delivers an optical signal intended to cause an optical simulator located at the distal end to deliver an excitatory stimulus to a selected body tissue, the stimulus being causing the selected body tissue to function as desired.

A further aspect of the present invention is an implantable cable for transmission of a signal to and from a body tissue of a vertebrate. The implantable cable includes a fiber optic bundle having a surface of non-immunogenic, physiologically compatible material, the fiber optic bundle being capable of being permanently implanted in a body cavity or subcutaneously, the fiber optic bundle having a distal end for implantation at or adjacent to the body tissue and a proximal end. The proximal end is adapted to couple to an optical signal receiver, the distal end is adapted to couple to a sensor; the fiber optic bundle delivers an optical signal from a coupled sensor intended to cause an optical signal receiver coupled to the proximal end to monitor characteristics of a selected body tissue.

A further aspect of the present invention is an implantable cable for transmission of power to a body tissue of a vertebrate. The implantable cable consists of a fiber optic lead having a surface of non-immunogenic, physiologically compatible material and being capable of being permanently implanted in a body cavity or subcutaneously. The fiber optic lead has a proximal end adapted to couple to an optical portal, a coupled optical portal being able to receive light from a source external to the vertebrate, and a distal end adapted to couple to a photoelectric receiver, a coupled photoelectric receiver being able to convert light into electrical energy for use at the distal end.

A further aspect of the present invention is an implantable cable for the transmission of power to a body tissue of a vertebrate. The implantable cable consists of a fiber optic lead having a surface of non-immunogenic, physiologically compatible material and being capable of being permanently implanted in a body cavity or subcutaneously. The fiber optic lead has a distal end adapted to couple to a sensor, a coupled sensor being able to produce light signal based on a measured characteristic of a selected body tissue region, and a proximal end being adapted to couple to an optical portal, the optical portal being able to receive light produced by a coupled sensor.

A further aspect of the present invention is an implantable cable for the transmission of power to a body tissue of a vertebrate. The implantable cable consists of a fiber optic lead having a surface of non-immunogenic, physiologically compatible material and being capable of being permanently implanted in a body cavity or subcutaneously. The fiber optic lead has a proximal end being adapted to be coupled to an optical portal, a coupled optical portal being able to receive light from a light source, and a distal end being adapted to be coupled to a photoelectric receiver, a coupled photoelectric receiver being able to convert light into electrical energy for use at the distal end.

A further aspect of the present invention is an implantable cable for the transmission of power to a body tissue of a vertebrate. The implantable cable includes a fiber optic lead having a cylindrical surface of non-immunogenic, physiologically compatible material and being capable of being permanently implanted in a body cavity or subcutaneously.

The fiber optic lead has a proximal end coupled to an electro-optical source; the electro-optical source converts electrical energy into light energy. The distal end coupled to a photoelectric receiver, the photoelectric receiver converts light energy into electrical energy for use at the distal end.

A further aspect of the present invention is a cardiac assist system. The cardiac assist system includes a primary device housing, having a control circuit therein, and a fiber optic based communication system to transmit and receive signals between a desired anatomical cardiac tissue region and the primary device housing.

A still further aspect of the present invention is a tissue invasive device. The tissue invasive device includes a primary device housing, having a control circuit therein and a fiber optic based communication system to transmit and receive signals between a selected tissue region and the primary device housing.

A further aspect of the present invention is a cardiac assist system. The cardiac assist system includes a primary device housing, having a control circuit therein, and a lead system to transmit and receive signals between a desired anatomical cardiac tissue region and the primary device housing. The lead system includes a sensing and stimulation system at an epicardial-lead interface with the desired anatomical cardiac tissue region. sensing and stimulation system includes optical sensing components to detect physiological signals from the desired anatomical cardiac tissue region.

A still further aspect of the present invention is a tissue invasive device. The tissue invasive device includes a primary device housing, having a control circuit therein, and a lead system to transmit and receive signals between a selected tissue region and the primary device housing. The lead system includes a sensing and stimulation system at an interface with the selected tissue region. The sensing and stimulation system includes optical sensing components to detect physiological signals from the selected tissue region.

A further aspect of the present invention is a cardiac assist system. The cardiac assist system consists of a primary device housing, having a control circuit therein, and a lead system to transmit and receive signals between a desired anatomical cardiac tissue region and the primary device housing. The lead system includes a sensing and stimulation system at an epicardial-lead interface with the desired anatomical cardiac tissue region; the sensing and stimulation system includes optical sensing components to detect physiological signals from the desired anatomical cardiac tissue region and electrical sensing components to detect physiological signals from the desired anatomical cardiac tissue region.

A still further aspect of the present invention is a tissue invasive device. The tissue invasive device includes a primary device housing, having a control circuit therein, and a lead system to transmit and receive signals between a selected tissue region and the primary device housing. The lead system includes a sensing and stimulation system at an epicardial-lead interface with the selected tissue region. The sensing and stimulation system includes optical sensing components to detect physiological signals from the selected tissue region and electrical sensing components to detect physiological signals from the selected tissue region.

A further aspect of the present invention is a transducer system to transmit and receive signals between a selected tissue region and a tissue invasive device. The transducer system consists of an electrical lead and an electrode located on an end of the electrical lead having an anti-antenna geometrical shape, the anti-antenna geometrical shape preventing the electrode from picking up and conducting stray electromagnetic interference.

A further aspect of the present invention is a cardiac assist transducer system to transmit and receive signals between a cardiac tissue region and a cardiac assist device. The cardiac assist transducer system consists of an electrical lead to deliver electrical pulses to the cardiac tissue region; and an electrode located on an end of the electrical lead having an anti-antenna geometrical shape, the anti-antenna geometrical shape preventing the electrode from picking up and conducting stray electromagnetic interference.

A still further aspect of the present invention is a cardiac assist system. The cardiac assist system consists of a primary device housing; the primary device housing has a control circuit therein; a lead system to transmit and receive signals between a heart and the primary device housing; a shielding formed around the lead system to shield the lead system from electromagnetic interference; and a biocompatible material formed around the shielding.

A further aspect of the present invention is a cardiac assist system. The cardiac assist system consists of a primary device housing; the primary device housing has a control circuit therein; a fiber optic EMI-immune lead system to transmit and receive signals between a heart and the primary device housing; and a biocompatible material formed around the fiber optic EMI-immune lead system.

A further aspect of the present invention is a cardiac assist system. The cardiac assist system consists of a primary device housing; the primary device housing has a control circuit therein; an optical-electrical lead system to transmit and receive signals between a heart and the primary device housing; a shielding formed around the optical-electrical lead system to shield the optical-electrical lead system from electromagnetic interference; and a biocompatible material formed around the shielding.

A further aspect of the present invention is a tissue invasive device. The tissue invasive device consists of a primary device housing; the primary device housing has a control circuit therein; a lead system to transmit and receive signals between a selected tissue region and the primary device housing; a shielding formed around the lead system to shield the lead system from electromagnetic interference; and a biocompatible material formed around the shielding.

A still further aspect of the present invention is a tissue invasive device. The tissue invasive device consists of a primary device housing; the primary device housing having a control circuit therein; a fiber optic EMI-immune lead system to transmit and receive signals between a selected tissue region and the primary device housing; and a biocompatible material formed around the fiber optic EMI-immune lead system.

A further aspect of the present invention is a tissue invasive device. The tissue invasive device consists of a primary device housing; the primary device housing having a control circuit therein; an optical-electrical lead system to transmit and receive signals between a selected tissue region and the primary device housing; a shielding formed around the optical-electrical lead system to shield the optical-electrical lead system from electromagnetic interference; and a biocompatible material formed around the shielding.

A further aspect of the present invention is a cardiac assist system. The cardiac assist system consists of a primary device housing; the primary device housing has a control circuit therein; a shielding formed around the primary device housing to shield the primary device housing and any circuits therein from electromagnetic interference; and a biocompatible material formed around the shielding.

A further aspect of the present invention is a tissue invasive device. The tissue invasive device consists of a primary device housing; the primary device housing having a control circuit therein; a shielding formed around the primary device housing to shield the primary device housing and any circuits therein from electromagnetic interference; and a biocompatible material formed around the shielding.

A further aspect of the present invention is a cardiac assist system to The cardiac assist system consists of a primary device housing; the primary device housing having a control circuit therein; a shielding formed around the primary device housing to shield the primary device housing and any circuits therein from electromagnetic interference; a biocompatible material formed around the shielding; and a detection circuit, located in the primary device housing, to detect an electromagnetic interference insult upon the cardiac assist system. The control circuit will place the cardiac assist system in an asynchronous mode upon detection of the electromagnetic interference insult by the detection system.

A still further aspect of the present invention is a tissue invasive device. The tissue invasive device consists of a primary device housing; the primary device housing has a control circuit therein operating in a first mode. A shielding formed around the primary device housing to shield the primary device housing and any circuits therein from electromagnetic interference; a biocompatible material formed around the shielding; and a detection circuit, located in the primary device housing, to detect an electromagnetic interference insult upon the tissue invasive device. The control circuit places the tissue invasive device in a second mode upon detection of the electromagnetic interference insult by the detection system.

A further aspect of the present invention is a cardiac assist system. The cardiac assist system consists of a primary device housing having a first control circuit, therein, to perform synchronous cardiac assist operations; a first shielding formed around the primary device housing to shield the primary device housing and any circuits therein from electromagnetic interference; a first biocompatible material formed around the first shielding; a secondary device housing having a second control circuit, therein, to perform asynchronous cardiac assist operations; a second shielding formed around the secondary device housing to shield the secondary device housing and any circuits therein from electromagnetic interference; a second biocompatible material formed around the second shielding; and a detection circuit, communicatively coupled to the first and second control circuits, to detect an electromagnetic interference insult upon the cardiac assist system. The first control circuit terminates synchronous cardiac assist operations and the second control circuit initiates asynchronous cardiac assist operations upon detection of the electromagnetic interference insult by the detection system.

A still further aspect of the present invention is a cardiac assist system for implanting in a body of a patient. The cardiac assist system consists of a main module; a first shielding formed around the main module to shield the main module and any circuits therein from magnetic-resonance imaging interference; a first biocompatible material formed around the first shielding; a magnetic-resonance imaging-immune auxiliary module; a second shielding formed around the magnetic-resonance imaging-immune auxiliary module to shield the magnetic-resonance imaging-immune auxiliary module and any circuits therein from magnetic-resonance imaging interference; a second biocompatible material formed around the second shielding; a communication channel between the main module and the magnetic-resonance imaging-immune auxiliary module for the magnetic-resonance imaging-immune auxiliary module to detect failure of the main module; and a controller for activating the magnetic-resonance imaging-immune auxiliary module upon detection of failure of the main module.

A further aspect of the present invention is a cardiac assist system for implanting in the body of a patient. The cardiac assist system consists of a main module; a first biocompatible material formed around the main module; an magnetic-resonance imaging-hardened auxiliary module; a shielding formed around the magnetic-resonance imaging-hardened auxiliary module to shield the magnetic-resonance imaging-hardened auxiliary module and any circuits therein from magnetic-resonance imaging interference; a second biocompatible material formed around the second shielding; and a communication channel between the main module and the magnetic-resonance imaging-hardened auxiliary module. The magnetic-resonance imaging-hardened auxiliary module detecting, through the communication channel, failure of the main module; the magnetic-resonance imaging-hardened auxiliary module including a controller for activating the magnetic-resonance imaging-hardened auxiliary module upon detection of failure of the main module.

A further aspect of the present invention is a cardiac assist device. The cardiac assist device consists of a primary device housing; the primary device housing having a control circuit therein; a shielding formed around the primary device housing to shield the primary device housing and any circuits therein from electromagnetic interference; a lead system to transmit and receive signals between a selected cardiac tissue region and the primary device housing; a switch to place the control circuitry into a fixed-rate mode of operation; an acoustic sensor to sense a predetermined acoustic signal. The switch places the control circuitry into a fixed-rate mode of operation when the acoustic sensor senses the predetermined acoustic signal.

A further aspect of the present invention is a cardiac assist system. The cardiac assist system includes a primary device housing; the primary device housing having a control circuit therein; a shielding formed around the primary device housing to shield the primary device housing and any circuits therein from electromagnetic interference; a lead system to transmit and receive signals between a selected cardiac tissue region and the primary device housing; a switch to place the control circuitry into a fixed-rate mode of operation; a near infrared sensor to sense a predetermined near infrared signal; the switch placing the control circuitry into a fixed-rate mode of operations when the near infrared sensor senses the predetermined near infrared signal.

A still further aspect of the present invention is an implantable cable for the transmission of signals to and from a body tissue of a vertebrate. The implantable cable consists of a fiber optic lead having a surface of non-immunogenic, physiologically compatible material and being capable of being permanently implanted in a body cavity or subcutaneously; the fiber optic lead having a distal end for implantation at or adjacent to the body tissue and a proximal end; the fiber optic lead including a first optical fiber and a second optical fiber; the first optical fiber having, a proximal end coupled to an optical signal source, and a distal end coupled to an optical stimulator. The optical signal source generating an optical signal intended to cause the optical stimulator located at a distal end to deliver an excitatory stimulus to a selected body tissue, the stimulus causing the selected body tissue to function as desired. The second optical fiber having a distal end coupled to a sensor, and a proximal end coupled to a device responsive to an optical signal delivered by the second optical fiber; the sensor generating an optical signal to represent a state of a function of the selected body tissue to provide feedback to affect the activity of the optical signal source.

A further aspect of the present invention is an implantable cable for the transmission of signals to and from a body tissue of a vertebrate. The implantable cable includes a fiber optic lead having a surface of non-immunogenic, physiologically compatible material and being capable of being permanently implanted in a body cavity or subcutaneously; the fiber optic lead having a distal end for implantation at or adjacent to the body tissue and a proximal end; the proximal end of the fiber optic lead being coupled to an optical signal source and an optical device. The distal end of the fiber optic lead being coupled to an optical stimulator and a sensor; the optical signal source generating an optical signal intended to cause the optical stimulator located at a distal end to deliver an excitatory stimulus to a selected body tissue, the stimulus being causing the selected body tissue to function as desired. The optical device being responsive to an optical signal generated by the sensor, the optical signal generated by the sensor rep representing a state of a function of the selected body tissue to provide feedback to affect the activity of the optical signal source.

A further aspect of the present invention is a cardiac assist system. The cardiac assist system includes a primary device housing including a power supply and a light source; the primary device housing having a control circuit therein; a shielding formed around the primary device housing to shield the primary device housing and any circuits therein from electromagnetic interference; a cardiac assist device associated with a heart; a photonic lead system to transmit between the primary device housing and the cardiac assist device, both power and control signals in the form of light; a photoresponsive device to convert the light transmitted by the photonic lead system into electrical energy and to sense variations in the light energy to produce control signals; a charge accumulating device to receive and store the electrical energy produced by the photoresponsive device; and a discharge control device, responsive to the control signals, to direct the stored electrical energy from the charge accumulating device to the cardiac assist device associated with the heart.

A further aspect of the present invention is a tissue implantable device. The tissue implantable device includes a primary device housing including a power supply and a light source; the primary device housing having a control circuit therein; a shielding formed around the primary device housing to shield the primary device housing and any circuits therein from electromagnetic interference; a tissue interface device associated with a distinct tissue region; a photonic lead system to transmit between the primary device housing and the tissue interface device, both power and control signals in the form of light; a photoresponsive device to convert the light transmitted by the photonic lead system into electrical energy and to sense variations in the light energy to produce control signals; a discharge control device, responsive to the control signals, to direct the stored electrical energy from the charge accumulating device to the tissue interface device associated with a distinct tissue region.

A further aspect of the present invention is a tissue implantable device. The tissue implantable device includes a primary device housing; the primary device housing having a control circuit therein a shielding formed around the primary device housing to shield the primary device housing and any circuits therein from electromagnetic interference; a lead system to transmit and receive signals between a tissue region of concern and the primary device housing; and a detection circuit to detect a phase timing of an external electromagnetic field; the control circuit altering its operations to avoid interfering with the detected external electromagnetic field.

A still further aspect of the present invention is a method for preventing a tissue implantable device failure during magnetic resonance imaging. The method includes determining a quiet period for a tissue implantable device and generating a magnetic resonance imaging pulse during a quiet period of the tissue implantable device.

A further aspect of the present invention is a method for preventing a tissue implantable device failure due to an external electromagnetic field source. The method includes detecting a phase timing of an external electromagnetic field and altering operations of the tissue implantable device to avoid interfering with the detected external electromagnetic field.

A further aspect of the present invention is a method for preventing a tissue implantable device failure during magnetic resonance imaging. The method includes detecting a phase timing of an external magnetic resonance imaging pulse field and altering operations of the tissue implantable device to avoid interfering with the detected external magnetic resonance imaging pulse field.

A further aspect of the present invention is a cardiac assist system for implanting in the body of a patient. The cardiac assist system includes a main module; an magnetic-resonance imaging-hardened auxiliary module; and a communication channel between the main module and the magnetic-resonance imaging-hardened auxiliary module; the magnetic-resonance imaging-hardened auxiliary module detecting, through the communication channel, failure of the main module; the magnetic-resonance imaging-hardened auxiliary module including a controller for activating the auxiliary module upon detection of failure of the main module.

A further aspect of the present invention is a signaling system for a two-module implantable medical device having a main module and an auxiliary module. The signaling system consists of signaling means in the main module for generating a signal to the auxiliary module, the signal representing a status of the main module or an instruction for the auxiliary module to activate; sensing means in the auxiliary module, in response to the signal from the signaling means, for determining if the auxiliary module should activate; and a switch to activate the auxiliary module when the sensing means determines that the signal from the signaling means indicates that the auxiliary module should activate.

A further aspect of the present invention is a cardiac assist system. The cardiac assist system includes a primary device housing; the primary device housing having a control circuit therein; a shielding formed around the primary device housing to shield the primary device housing and any circuits therein from electromagnetic interference; and a lead system to transmit and receive signals between a heart and the primary device housing; the control circuitry including an oscillator and amplifier operating at an amplitude level above that of an induced signal from a magnetic-resonance imaging field.

A still further aspect of the present invention is a cardiac assist system. The cardiac assist system includes a primary device housing; the primary device housing having a control circuit therein; a shielding formed around the primary device housing to shield the primary device housing and any circuits therein from electromagnetic interference; a lead system to transmit and receive signals between a heart and the primary device housing; a switch to place the control circuitry into a fixed-rate mode of operation; a changing magnetic field sensor to sense a change in magnetic field around the primary housing, the switch placing the control circuitry into a fixed-rate mode of operation when the changing magnetic field sensor senses a predetermined encoded changing magnetic field.

A further aspect of the present invention is an electromagnetic radiation immune tissue invasive delivery system. The electromagnetic radiation immune tissue invasive delivery system includes a photonic lead having a proximal end and a distal end; a storage device, located at the proximal end of the photonic lead, to store a therapeutic substance to be introduced into a tissue region; a delivery device to delivery a portion of the stored therapeutic substance to a tissue region; a light source, in the proximal end of the photonic lead, to produce a first light having a first wavelength and a second light having a second wavelength; a wave-guide between the proximal end and distal end of the photonic lead; a bio-sensor, in the distal end of the photonic lead, to sense characteristics of a predetermined tissue region; a distal sensor, in the distal end of the photonic lead, to convert the first light into electrical energy and, responsive to the bio-sensor, to reflect the second light back the proximal end of the photonic lead such that a characteristic of the second light is modulated to encode the sensed characteristics of the predetermined tissue region; a proximal sensor, in the proximal end of the photonic lead, to convert the modulated second light into electrical energy; and a control circuit, in response to the electrical energy from the proximal sensor, to control an amount of the stored therapeutic substance to be introduced into the tissue region.

A further aspect of the present invention is an electromagnetic radiation immune tissue invasive delivery system. The electromagnetic radiation immune tissue invasive delivery system includes a photonic lead having a proximal end and a distal end; a storage device, located at the proximal end of the photonic lead, to store a therapeutic substance to be introduced into a tissue region; a delivery device to deliver a portion of the stored therapeutic substance to a tissue region; a light source, in the proximal end of the photonic lead, to produce a first light having a first wavelength and a second light having a second wavelength; a wave-guide between the proximal end and distal end of the photonic lead; a bio-sensor, in the distal end of the photonic lead, to sense characteristics of a predetermined tissue region; a distal sensor, in the distal end of the photonic lead, to convert the first light into electrical energy and, responsive to the bio-sensor, to emit a second light having a second wavelength to proximal end of the photonic lead such that a characteristic of the second light is modulated to encode the sensed characteristics of the predetermined tissue region; a proximal sensor, in the proximal end of the photonic lead, to convert the modulated second light into electrical energy; and a control circuit, in response to the electrical energy from the proximal sensor, to control an amount of the stored therapeutic substance to be introduced into the tissue region.

A further aspect of the present invention is an electromagnetic radiation immune tissue invasive stimulation system. The electromagnetic radiation immune tissue invasive stimulation system includes a photonic lead having a proximal end and a distal end; a light source, in the proximal end of the photonic lead, to produce a first light having a first wavelength; a wave-guide between the proximal end and distal end of the photonic lead; a distal sensor, in the distal end of the photonic lead, to convert the first light into electrical energy into control signals; an electrical energy storage device to store electrical energy; and a control circuit, in response to the control signals, to cause a portion of the stored electrical energy to be delivered to a predetermined tissue region.

A further aspect of the present invention is an electromagnetic radiation immune tissue invasive sensing system. The electromagnetic radiation immune tissue invasive sensing system includes a photonic lead having a proximal end and a distal end; a light source, in the proximal end of the photonic lead, to produce a first light having a first wavelength; a waveguide between the proximal end and distal end of the photonic lead; a distal sensor, in the distal end of the photonic lead, to convert the first light into electrical energy into control signals; an electrical energy storage device to store electrical energy; and a bio-sensor, in the distal end of the photonic lead, to sense a characteristic of a predetermined tissue region. The light source, in the proximal end of the photonic lead, produces a second light having a second wavelength. The distal sensor, in the distal end of the photonic lead and responsive to the bio-sensor, reflects the second light back the proximal end of the photonic lead such that a characteristic of the second light is modulated to encode the sensed characteristic of the predetermined tissue region.

A still further aspect of the present invention is an electromagnetic radiation immune tissue invasive sensing system. The electromagnetic radiation immune tissue invasive sensing system includes a photonic lead having a proximal end and a distal end; a light source, in the proximal end of the photonic lead, to produce a first light having a first wavelength and a second light having a second wavelength; a wave-guide between the proximal end and the distal end of the photonic lead; a bio-sensor, in the distal end of the photonic lead, to sense characteristics of a predetermined tissue region; and a distal sensor, in the distal end of the photonic lead, to convert the first light into electrical energy and, responsive to the bio-sensor, to reflect the second light back the proximal end of the photonic lead such that a characteristic of the second light is modulated to encode the sensed characteristics of the predetermined tissue region.

A further aspect of the present invention is an electromagnetic radiation immune tissue invasive sensing system. The electromagnetic radiation immune tissue invasive sensing system includes a photonic lead having a proximal end and a distal end; a light source, in the proximal end of the photonic lead, to produce a first light having a first wavelength; a wave-guide between the proximal end and distal end of the photonic lead; a bio-sensor, in the distal end of the photonic lead, to sense characteristics of a predetermined tissue region; and a distal sensor, in the distal end of the photonic lead, to convert the first light into electrical energy and, responsive to the bio-sensor, to emit a second light having a second wavelength to proximal end of the photonic lead such that a characteristic of the second light is modulated to encode the sensed characteristics of the predetermined tissue region.

A further aspect of the present invention is a photonic lead system. The photonic lead system includes a photonic lead having a distal end and a proximal end; and a magnetic radiation coil, located in the distal end, to detect characteristics of magnetic radiation of a predetermined nature.

A still further aspect of the present invention is an electromagnetic radiation immune sensing system. The electromagnetic radiation immune sensing system includes a photonic lead having a proximal end and a distal end; a light source, in the proximal end of the photonic lead, to produce a first light having a first wavelength and a second light having a second wavelength; a wave-guide between the proximal end and distal end of the photonic lead; a biosensor, in the distal end of the photonic lead, to measure changes in an electric field located outside a body, the electric field being generated by the shifting voltages on a body's skin surface; and a distal sensor, in the distal end of the photonic lead, to convert the first light into electrical energy and, responsive to the bio-sensor, to reflect the second light back the proximal end of the photonic lead such that a characteristic of the second light is modulated to encode the measured changes in the electric field.

A further aspect of the present invention is an electromagnetic radiation immune sensing system. The electromagnetic radiation immune sensing system includes a photonic lead having a proximal end and a distal end; a light source, in the proximal end of the photonic lead, to produce a first light having a first wavelength; a wave-guide between the proximal end and distal end of the photonic lead; a bio-sensor, in the distal end of the photonic lead, to measure changes in an electric field located outside a body, the electric field being generated by the shifting voltages on a body's skin surface; and a distal sensor, in the distal end of the photonic lead, to convert the first light into electrical energy and, responsive to the bio-sensor, to emit a second light having a second wavelength to proximal end of the photonic lead such that a characteristic of the second light is modulated to encode the measured changes in the electric field.

A further aspect of the present invention is a cardiac assist system. The cardiac assist system includes a primary device housing, the primary device housing having a control circuit therein; a shielding formed around the primary device housing to shield the primary device housing and any circuits therein from electromagnetic interference; a lead system to transmit and receive signals between a heart and the primary device housing; a switch to place the control circuitry into a fixed-rate mode of operation; and a changing magnetic field sensor to sense a change in magnetic field around the primary housing. The switch causes the control circuitry to turn-off and cease operation when the changing magnetic field sensor senses a predetermined encoded changing magnetic field.

A further aspect of the present invention is an electromagnetic radiation immune tissue invasive energy transfer system. The electromagnetic radiation immune tissue invasive energy transfer system includes a photonic lead having a proximal end and a distal end; a light source, at the proximal end of the photonic lead; a wave-guide between the proximal end and distal end of the photonic lead; a radiation scattering medium at the distal end of the photonic lead to receive radiation from the wave-guide; and a plurality of sensors to receive scattered radiation from the radiation scattering medium and convert the received scattered radiation into electrical energy.

A further aspect of the present invention is an electromagnetic radiation immune tissue invasive energy transfer system. The electromagnetic radiation immune tissue invasive energy transfer system includes a photonic lead having a proximal end and a distal end; a light source, at the proximal end of the photonic lead; a first wave-guide between the proximal end and distal end of the photonic lead; a second wave-guide, having a plurality of beam splitters therein at the distal end of the photonic lead to receive radiation from the first wave-guide; and a plurality of sensors to receive radiation from the beam splitters in the second wave-guide and a convert the received radiation into electrical energy.

A further aspect of the present invention is an electromagnetic radiation immune tissue invasive energy transfer system. The electromagnetic radiation immune tissue invasive energy transfer system includes a photonic lead having a proximal end and a distal end; a light source, at the proximal end of the photonic lead; a wave-guide between the proximal end and distal end of the photonic lead; and a plurality of stacked sensors to receive radiation from the wave-guide and convert the received radiation into electrical energy. Each sensor absorbs a fraction of radiation incident upon the stack of sensors.

A further aspect of the present invention is an electromagnetic radiation immune tissue invasive energy transfer system. The electromagnetic radiation immune tissue invasive energy transfer system includes a photonic lead having a proximal end and a distal end; a light source, at the proximal end of the photonic lead; a wave-guide between the proximal end and distal end of the photonic lead; and a plurality of concentric sensors to receive radiation from the wave-guide and convert the received radiation into electrical energy. Each concentric sensors absorbs a fraction of radiation from said wave-guide.

A further aspect of the present invention is an electromagnetic radiation immune tissue invasive energy transfer system. The electromagnetic radiation immune tissue invasive energy transfer system includes a photonic lead having a proximal end and a distal end; a light source, at the proximal end of the photonic lead; a wave-guide between the proximal end and distal end of the photonic lead; a sensor to receive radiation from the wave-guide and convert the received radiation into electrical energy; and a plurality of switchable capacitors connected in parallel to an output of the sensor to enable simultaneous charging of the capacitors.

A further aspect of the present invention is an electromagnetic radiation immune tissue invasive energy transfer system. The electromagnetic radiation immune tissue invasive energy transfer system includes a photonic lead having a proximal end and a distal end; a light source, at the proximal end of the photonic lead; a wave-guide between the proximal end and distal end of the photonic lead; a sensor to receive radiation from the wave-guide and convert the received radiation into electrical energy; a control circuit connected to an output of the sensor; and a plurality of switchable capacitors connected to the control circuit.

A further aspect of the present invention is an electromagnetic radiation immune tissue invasive energy transfer system. The electromagnetic radiation immune tissue invasive energy transfer system includes a photonic lead having a proximal end and a distal end; a light source, at the proximal end of the photonic lead; a wave-guide between the proximal end and distal end of the photonic lead; a sensor to receive radiation from the wave-guide and convert the received radiation into electrical energy; and a plurality of switchable capacitors connected to an output of the sensor to enable sequential charging of the capacitors with a pre-determined pulse intensity and duration.

A further aspect of the present invention is an electromagnetic radiation immune tissue invasive energy transfer system. The electromagnetic radiation immune tissue invasive energy transfer system includes a light source; a radiation beam splitter having multiple beam splitters; a plurality of wave-guides, each wave-guide receiving radiation from a beam splitter; and a plurality of sensors, each sensor receiving radiation from one of the plurality of wave-guides to convert the received radiation into electrical energy.

A further aspect of the present invention is a tissue invasive photonic system. The tissue invasive photonic system includes a photonic lead having a proximal end and a distal end; a light source, in the proximal end of the photonic lead, to produce a first light having a first wavelength and a second light having a second wavelength; a wave-guide between the proximal end and distal end of the photonic lead; a radiation scattering medium at the distal end of the photonic lead to receive radiation from the wave-guide; a plurality of power sensors to receive scattered radiation from the radiation scattering medium and convert the received scattered radiation into electrical energy; a bio-sensor, in the distal end of the photonic lead, to sense characteristics of a predetermined tissue region; and a distal emitter, in the distal end of the photonic lead and responsive to the bio-sensor, to emit a second light having a second wavelength to proximal end of the photonic lead such that a characteristic of the second light is modulated to encode the sensed characteristics of the predetermined tissue region.

A further aspect of the present invention is a tissue invasive photonic system. The tissue invasive photonic system includes a photonic lead having a proximal end and a distal end; a light source, in the proximal end of the photonic lead, to produce a first light having a first wavelength and a second light having a second wavelength; a first wave-guide between the proximal end and distal end of the photonic lead; a second wave-guide, having a plurality of power beam splitters therein at the distal end of the photonic lead to receive and reflect the first light from the first wave-guide; a plurality of power sensors to receive the first light from the power beam splitters in the second wave-guide and convert the received first light into electrical energy; a bio-sensor, in the distal end of the photonic lead, to sense characteristics of a predetermined tissue region; and a distal emitter, in the distal end of the photonic lead and responsive to the bio-sensor, to emit a second light having a second wavelength to proximal end of the photonic lead such that a characteristic of the second light is modulated to encode the sensed characteristics of the predetermined tissue region.

A further aspect of the present invention is a tissue invasive photonic system. The tissue invasive photonic system includes a photonic lead having a proximal end and a distal end; a light source, in the proximal end of the photonic lead, to produce a first light having a first wavelength and a second light having a second wavelength; a wave-guide between the proximal end and distal end of the photonic lead; a plurality of power sensors to receive the first light from the wave-guide and convert the received first light into electrical energy, each power sensor absorbing a fraction of the received first light; a bio-sensor, in the distal end of the photonic lead, to sense characteristics of a predetermined tissue region; and a distal emitter, in the distal end of the photonic lead and responsive to the bio-sensor, to emit a second light having a second wavelength to proximal end of the photonic lead such that a characteristic of the second light is modulated to encode the sensed characteristics of the predetermined tissue region.

A further aspect of the present invention is a tissue invasive photonic system. The tissue invasive photonic system includes a photonic lead having a proximal end and a distal end; a light source, in the proximal end of the photonic lead, to produce a first light having a first wavelength and a second light having a second wavelength; a wave-guide between the proximal end and distal end of the photonic lead; a bio-sensor, in the distal end of the photonic lead, to sense characteristics of a predetermined tissue region; a distal emitter, in the distal end of the photonic lead and responsive to the bio-sensor, to emit a second light having a second wavelength to proximal end of the photonic lead such that a characteristic of the second light is modulated to encode the sensed characteristics of the predetermined tissue region; a power sensor to receive the first light from the wave-guide and convert the received first light into electrical energy; and a plurality of switchable capacitors operatively connected to an output of the power sensor.

A further aspect of the present invention is a tissue invasive photonic system. The tissue invasive photonic system includes a photonic lead having a proximal end and a distal end; a light source, in the proximal end of the photonic lead, to produce a first light having a first wavelength and a second light having a second wavelength; a wave-guide between the proximal end and distal end of the photonic lead; a radiation scattering medium at the distal end of the photonic lead to receive radiation from the wave-guide; a plurality of power sensors to receive scattered radiation from the radiation scattering medium and convert the received scattered radiation into electrical energy; a bio-sensor, in the distal end of the photonic lead, to sense characteristics of a predetermined tissue region; a distal sensor, in the distal end of the photonic lead, responsive to the bio-sensor, to reflect the second light back to the proximal end of the photonic lead such that a characteristic of the second light is modulated to encode the sensed characteristics of the predetermined tissue region; and a beam splitter to direct the second light to the distal sensor.

A further aspect of the present invention is a tissue invasive photonic system. The tissue invasive photonic system includes a photonic lead having a proximal end and a distal end; a light source, in the proximal end of the photonic lead, to produce a first light having a first wavelength and a second light having a second wavelength; a first wave-guide between the proximal end and distal end of the photonic lead; a second wave-guide, having a plurality of power beam splitters therein at the distal end of the photonic lead to receive and reflect the first light from the first wave-guide; a plurality of power sensors to receive the first light from the power beam splitters in the second wave-guide and convert the received first light into electrical energy; a bio-sensor, in the distal end of the photonic lead, to sense characteristics of a predetermined tissue region; a sensor beam splitter to reflect the second light from the first wave-guide; and a distal sensor, in the distal end of the photonic lead, responsive to the bio-sensor, to receive the second light from the sensor beam splitter and to reflect the second light back to the proximal end of the photonic lead such that a characteristic of the second light is modulated to encode the sensed characteristics of the predetermined tissue region.

A further aspect of the present invention is a tissue invasive photonic system. The tissue invasive photonic system a photonic lead having a proximal end and a distal end; a light source, in the proximal end of the photonic lead, to produce a first light having a first wavelength and a second light having a second wavelength; a wave-guide between the proximal end and distal end of the photonic lead; a plurality of power sensors to receive the first light from the wave-guide and convert the received first light into electrical energy, each power sensor absorbing a fraction of the received first light; a bio-sensor, in the distal end of the photonic lead, to sense characteristics of a predetermined tissue region; a sensor beam splitter to reflect the second light from the wave-guide; and a distal sensor, in the distal end of the photonic lead, responsive to the bio-sensor, to receive the second light from the sensor beam splitter and to reflect the second light back to the proximal end of the photonic lead such that a characteristic of the second light is modulated to encode the sensed characteristics of the predetermined tissue region.

A further aspect of the present invention is a tissue invasive photonic system. The tissue invasive photonic system includes a photonic lead having a proximal end and a distal end; a light source, in the proximal end of the photonic lead, to produce a first light having a first wavelength and a second light having a second wavelength; a wave-guide between the proximal end and distal end of the photonic lead; a bio-sensor, in the distal end of the photonic lead, to sense characteristics of a predetermined tissue region; a sensor beam splitter to reflect the second light from the waveguide; a distal sensor, in the distal end of the photonic lead, responsive to the bio-sensor, to receive the second light from the sensor beam splitter and to reflect the second light back to the proximal end of the photonic lead such that a characteristic of the second light is modulated to encode the sensed characteristics of the predetermined tissue region; a power sensor to receive the first light from the wave-guide and convert the received first light into electrical energy; and a plurality of switchable capacitors operatively connected to an output of the power sensor.

BRIEF DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein.

DETAILED DESCRIPTION OF THE PRESENT INVENTION

Figure 1:
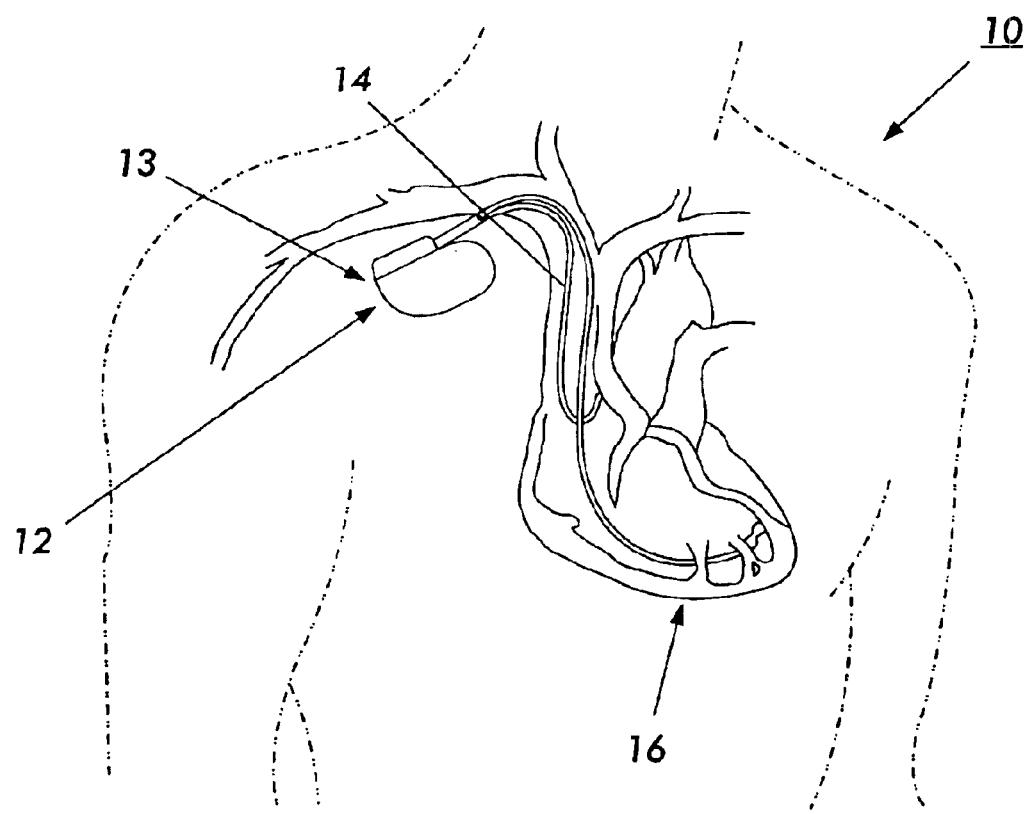
FIGS. 1 and 2 are illustrations of conventional techniques used to protect against electromagnetic interference.
Figure 2:
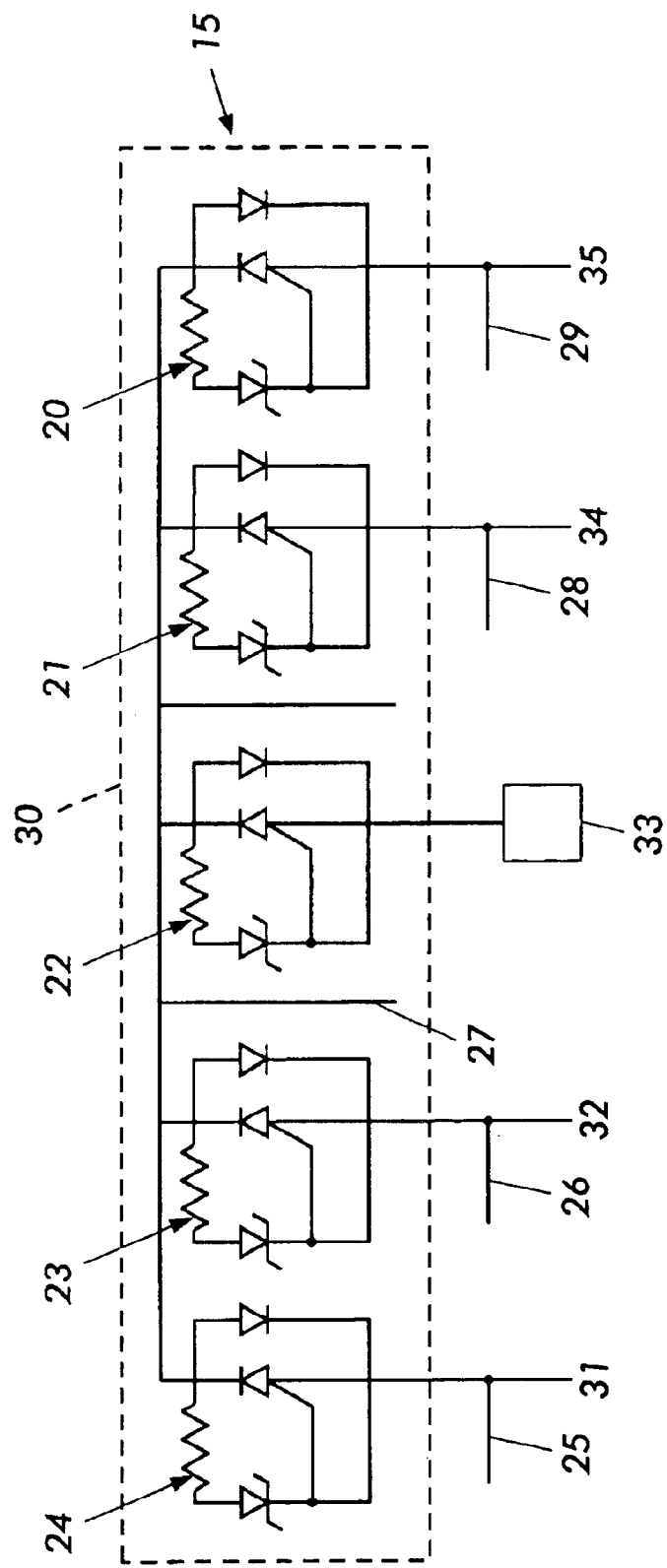
Figure 3:
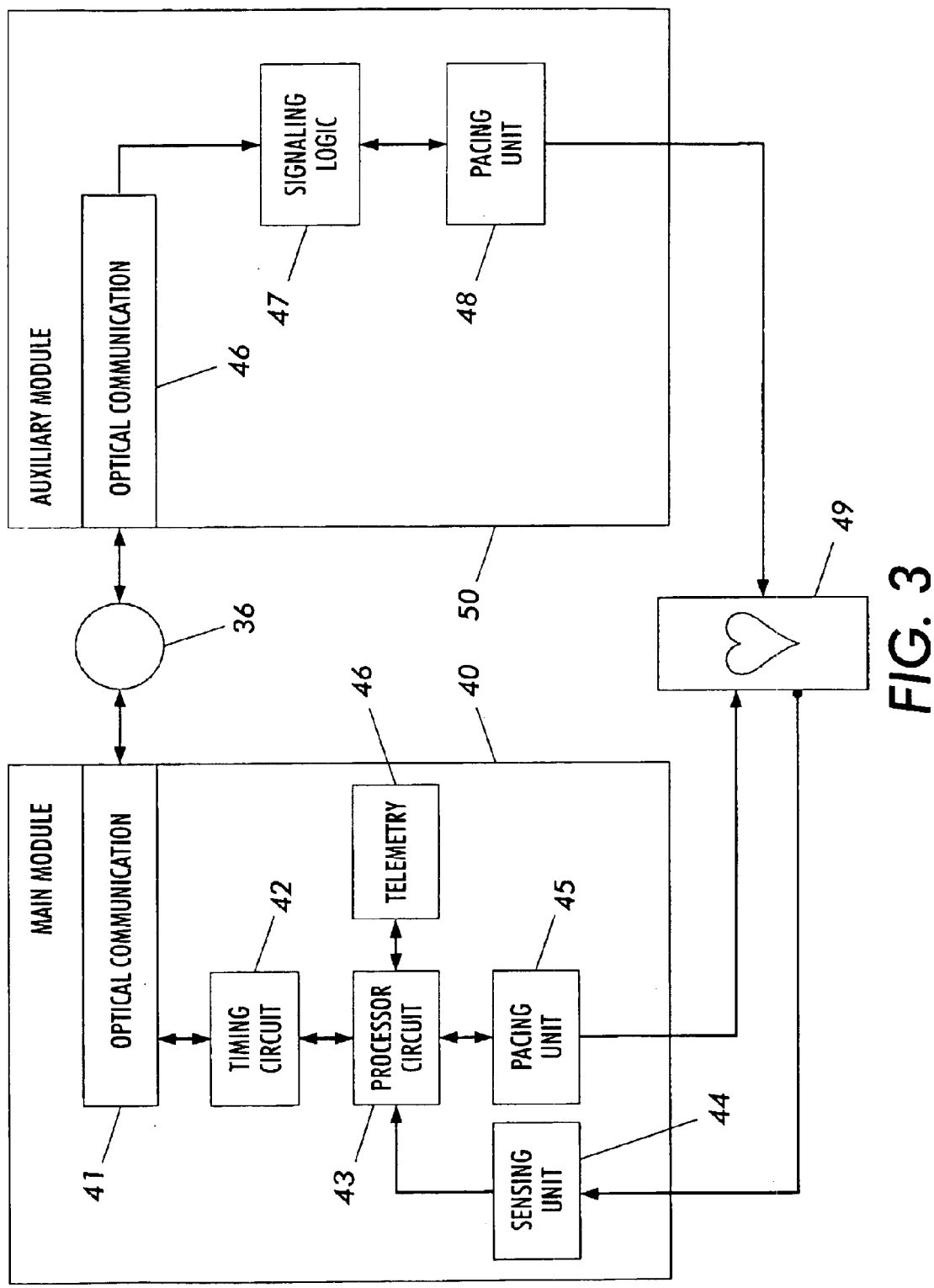
FIG. 3 is a block diagram of one embodiment of a MRI immune cardiac assist system according to some or all of the concepts of the present invention.

As noted above, the present invention is directed to an implantable device that is immune or hardened to electromagnetic insult or interference. FIG. 3 illustrates a cardiac assist system that is immune or hardened electromagnetic insult or interference, namely to magnetic radiation imaging, MRI. As illustrated in FIG. 3, a main module 40 includes a processor circuit 43 that controls the operations of the cardiac assist system. The processor unit 43 provides control signals to a pacing unit 45. The pacing unit 45 produces packets of energy to stimulate the heart 49 to start beating or to beat at a predetermined rate or pace. The processor circuit 43 also receives information about the conditions of the heart 49 from a sensing unit 44. The sensing unit 44, through sensors or electrodes, monitors the conditions of the heart 49 to provide feedback information to the processor circuit 43.

A telemetry unit 46 is also provided in the main module 40 to provide information to the processor circuit 43 received from sources external to the body. Lastly, a timing circuit 42 is provided to communicate with an auxiliary module 50 through an optical communication interface 41 in the main module 40, over optical communication channels 36, such as fiber optics, and through an optical communication interface 46 in the auxiliary module 50. In response to the information received from the optical communication interface 46, a signaling logic circuit 47 will activate or suppress a pacing unit 48. In this embodiment, if there is a failure in the main module 40 due to error or electromagnetic insult or interference, the signaling logic circuit 47 will detect the shutdown of the main module 40 and cause the auxiliary module 50 to take over the pacing of the heart 49 in an asynchronous manner through pacing unit 48.

As described above, the cardiac assist system performs synchronous cardiac assist operations through a main module. A secondary module is provided to perform asynchronous cardiac assist operations. Upon detection of an electromagnetic interference insult upon the cardiac assist system, the control circuit of the main module terminates synchronous cardiac assist operations, and the control circuit of the secondary module initiates asynchronous cardiac assist operations upon detection of the electromagnetic interference insult. The control circuit of the secondary module places the cardiac assist system in the asynchronous mode for a duration of the electromagnetic interference insult and terminates the asynchronous mode of the cardiac assist system upon detection of an absence of an electromagnetic interference insult. The control circuit of the main module terminates the synchronous mode of the cardiac assist system for the duration of the electromagnetic interference insult and re-initiates the synchronous mode of the cardiac assist system upon detection of an absence of an electromagnetic interference insult.

Figure 4:
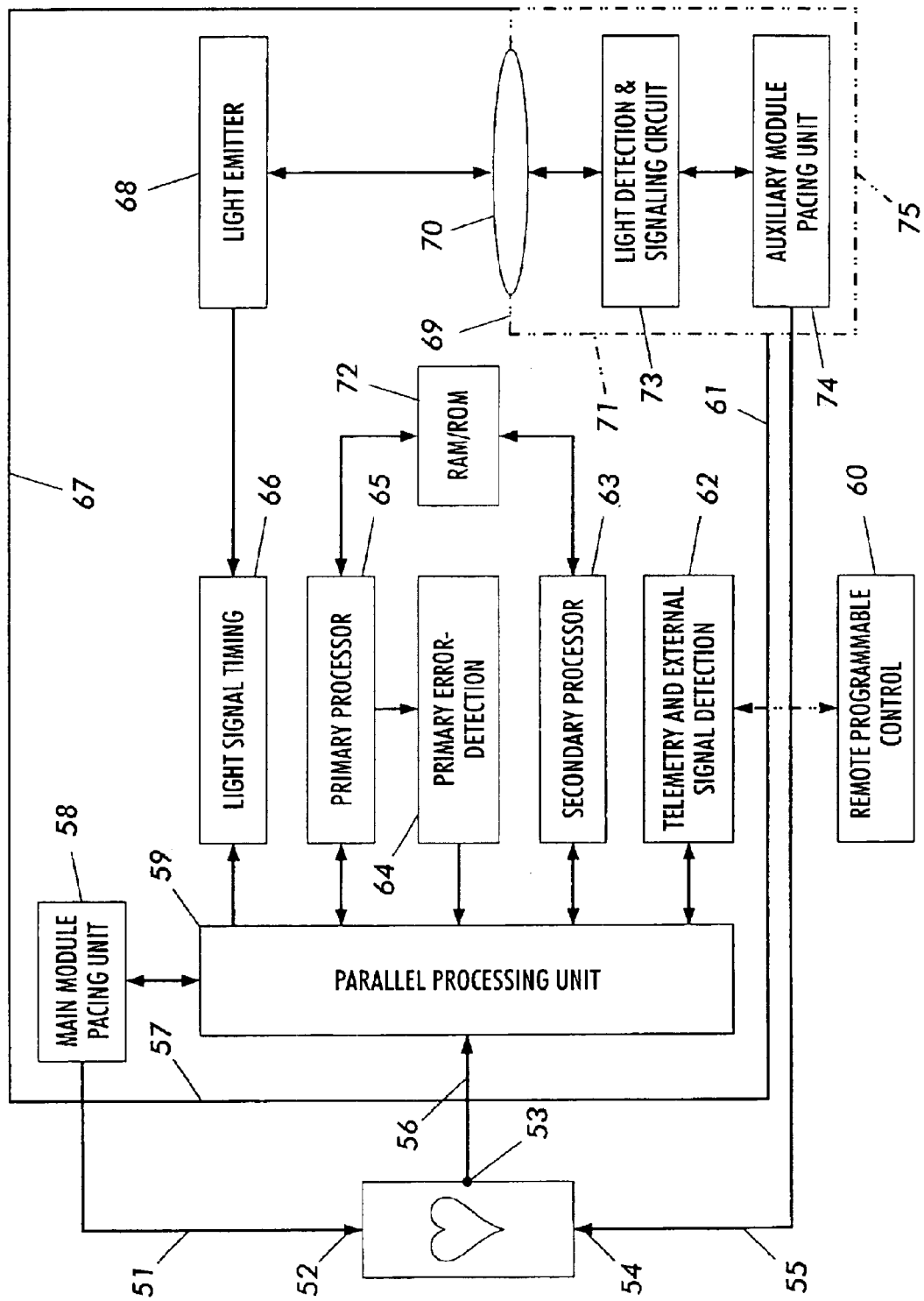
FIG. 4 is a block diagram of another embodiment of a MRI immune cardiac assist system according to some or all of the concepts of the present invention.

FIG. 4 is a more detail schematic of FIG. 3. In FIG. 4, a cardiac assist system is immune or hardened electromagnetic insult or interference, namely to magnetic radiation imaging, MRI. As illustrated in FIG. 4, a main module 67 includes a parallel processing unit 59 and primary and secondary processors 65 and 63 that control the operations of the cardiac assist system. The parallel processing unit 59 provides control signals to a pacing unit 58. The pacing unit 58 produces packets of energy to stimulate the heart to start beating or to beat at a predetermined rate or pace through lead(s) 51 and electrode 52. The parallel processing unit 59 also receives information about the conditions of the heart 49 from a sensor 53 through lead(s) 56. The sensor 53 monitors the conditions of the heart to provide feedback information to the parallel processing unit 59.

A telemetry unit 62 is also provided in the main module 67 to provide information to the parallel processing unit 59 received from sources 60 external to the body. Memory 72 is provided for the processing of the cardiac assist system, and a primary error detection circuit 64 is included to detect any failures in the main module 67. Lastly, a timing circuit 66 is provided to communicate with an auxiliary module 69 through an optical emitter 68 in the main module 67, over optical communication channels 70, such as fiber optics, and through a light detection and signaling circuit 73 in the auxiliary module 69.

In response to the information received from the light detection and signaling circuit 73, a pacing unit 74 will activate or de-activate. In this embodiment, if there is a failure in the main module 67 due to error or electromagnetic insult or interference, the light detection and signaling circuit 73 will detect the shutdown of the main module 67 and cause the auxiliary module 69 to take over the pacing of the heart in an asynchronous manner through pacing unit 74, lead(s) 55, and electrode 54.

As described above, the cardiac assist system performs synchronous cardiac assist operations through a main module. A secondary module is provided to perform asynchronous cardiac assist operations. Upon detection of an electromagnetic interference insult upon the cardiac assist system, the control circuit of the main module terminates synchronous cardiac assist operations, and the control circuit of the secondary module initiates asynchronous cardiac assist operations upon detection of the electromagnetic interference insult. The control circuit of the secondary module places the cardiac assist system in the asynchronous mode for a duration of the electromagnetic interference insult and terminates the asynchronous mode of the cardiac assist system upon detection of an absence of an electromagnetic interference insult. The control circuit of the main module terminates the synchronous mode of the cardiac assist system for the duration of the electromagnetic interference insult and re-initiates the synchronous mode of the cardiac assist system upon detection of an absence of an electromagnetic interference insult.

Figure 30:
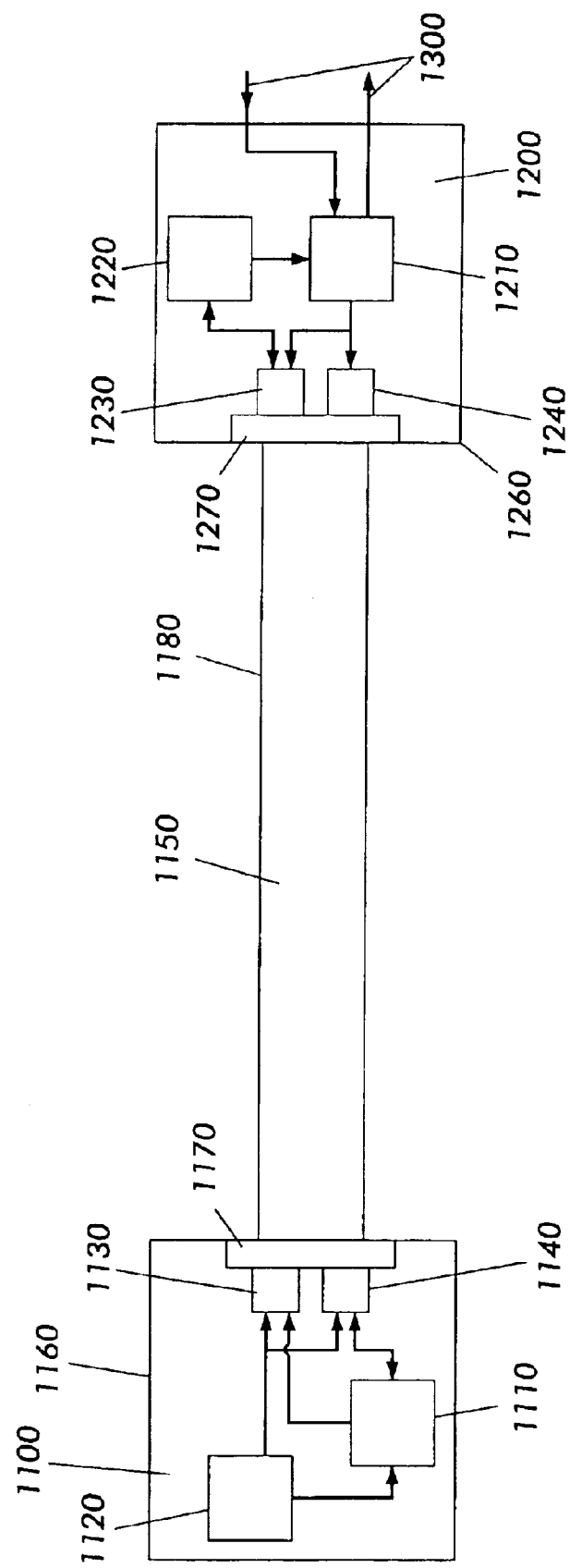
FIG. 30 illustrates a block diagram of a cardiac assist system.

FIG. 30 illustrates a cardiac assist system that includes a primary device housing 1100. The primary device housing 1100 includes a control circuit 1110, such as a microprocessor integrated circuit for controlling the operations of the cardiac assist system. The control circuit 1110 may select a mode of operation for the cardiac assist system based on predetermined sensed parameters. The primary device housing 1100 may also include circuitry (not shown) to detect and isolate cross talk between device pulsing operations and device sensing operations. The control circuit 1110 may isolate physiological signals using a noise filtering circuit or a digital noise filtering.

The primary device housing 1100 is implantable such that the control circuit 1110 can be programmable from a source external of the primary device housing 1100 or the control circuit 1110 can provide physiological diagnostics to a source external of the primary device housing 1100.

The primary device housing 1100 includes a power source 1120. The power source 1120 may be a battery power source in combination with a battery power source measuring circuit. In this embodiment, the control circuit 1110 can automatically adjust a value for determining an elective replacement indication condition of a battery power source such that the value is automatically adjusted by the control circuit 1110 in response to a measured level of a state of the battery power source, the measured level generated by the battery power source measuring circuit connected to the battery power source.

The primary device housing 1100 includes an optical emitter 1130, an optical sensor 1140, and an interface 1170 to put the primary device housing 1100 in operative communication with a lead system 1150.

The primary device housing 1100 may also include a switch (not shown), such as a reed switch or solid state switch, to place the control circuit 1110 into a fixed-rate mode of operation and an acoustic sensor (not shown) or near infrared sensor (not shown) to sense a predetermined acoustic signal. The switch places the control circuit 1110 into a fixed-rate mode of operation when the acoustic sensor or near infrared sensor senses the predetermined acoustic signal or the predetermined infrared signal.

The primary device housing 1100 has formed around it a shield 1160 to shield the primary device housing 1100 and any circuits therein from electromagnetic interference.

The shield 1160 may be a metallic sheath, a carbon composite sheath, or a polymer composite sheath to shield the primary device housing 1100 and any circuits therein from electromagnetic interference. The shield 1160 is further covered with a biocompatible material wherein the biocompatible material may be a non-permeable diffusion resistant biocompatible material. The primary device housing 1100 may also include a detection circuit (not shown) to detect a phase timing of an external electromagnetic field such that the control circuit 1110 alters its operations to avoid interfering with the detected external electromagnetic field.

FIG. 30 further illustrates a lead system 1150 connected to the primary device housing 1100. The lead system 1150 provides a communication path for information to be transported between the primary device housing 1100 and a distal location in the body. The lead system 1150 also may be a conduit of power or energy from the primary device housing 1100 to the distal location in the body.

In the example illustrated in FIG. 30, the lead system 1150 may provide a path for control signals to be transferred to the distal location of the body, such as the heart muscle tissue. These control signals are used to control the operations of a secondary device 1200, such as stimulating the beating of the heart. The lead system 1150 may also provide a path for signals representing sensed biological conditions to be transferred from the distal location of the body to the primary device housing 1100 so that the functionality of the heart muscle tissue can be effectively monitored.

The lead system 1150 may be a fiber optic based communication system wherein the fiber optic communication system contains at least one channel within a multi-fiber optic bundle. The fiber optic based communication system is covered with a biocompatible material wherein the biocompatible material is a non-permeable diffusion resistant biocompatible material.

The lead system 1150 may also be a plurality of electrical leads that have a shield 1180 therearound to prevent the electrical leads from conducting stray electromagnetic interference. This shield 1180 may be a metallic sheath, a carbon composite sheath, or a polymer composite sheath to prevent the electrical leads from conducting stray electromagnetic interference. In addition to the shield 1180 or in lieu of the shield 1180, each electrical lead may include an electrical filter wherein the electrical filter removes stray electromagnetic interference from a signal being received from the electrical lead. The electrical filter may comprise capacitive and inductive filter elements adapted to filter out predetermined frequencies of electromagnetic interference. The shield 1180 is covered with a biocompatible material wherein the biocompatible material is a non-permeable diffusion resistant biocompatible material.

The electrical leads maybe unipolar leads, bipolar leads, or a combination of unipolar and bipolar leads. The lead system 1150 may also be a combination of a fiber optic based communication system and electrical leads.

The lead system 1150 may also include a detection circuit (not shown) to detect a phase timing of an external electromagnetic field such that the control circuit 1110 alters its operations to avoid interfering with the detected external electromagnetic field.

In FIG. 30, the secondary housing 1200 includes a control circuit 1210, such as a microprocessor integrated circuit. The secondary device housing 1200 may also include circuitry (not shown) to detect and isolate cross talk between device pulsing operations and device sensing operations. The control circuit 1210 may isolate physiological signals using a noise filtering circuit or a digital noise filtering.

The secondary device housing 1200 includes a power source 1220. The power source 1220 may be a battery power source or capacitor or other device for storing. The primary device housing 1200 includes an optical emitter 1230, an optical sensor 1240, and an interface 1270 to put the secondary device housing 1200 in operative communication with the lead system 1150.

The secondary device housing 1200 has formed around it a shield 1260 to shield the secondary device housing 1200 and any circuits therein from electromagnetic interference.

The shield 1260 may be a metallic sheath, a carbon composite sheath, or a polymer composite sheath to shield the secondary device housing 1200 and any circuits therein from electromagnetic interference. The shield 1260 is further covered with a biocompatible material wherein the biocompatible material may be a non-permeable diffusion resistant bibcompatible material.

The secondary housing 1200 may also include electrodes 1300 for either stimulating a tissue region or sensing biological characteristics or parameters from the tissue region. More details as to the construction of the secondary device are set forth below in the describing of distal end elements.

As an alternative to electrodes 1300, the secondary device housing 1200 may include a sensing and stimulation system that includes optical pulsing components to deliver a stimulus of a predetermined duration and power to the desired anatomical cardiac tissue region; a sensing and stimulation system that includes optical pulsing components to deliver a stimulus of a predetermined duration and power to the desired anatomical cardiac tissue region and electrical pulsing components to deliver a stimulus of a predetermined duration and power to the desired anatomical cardiac tissue region; a hydrostatic pressure sensing components to detect physiological signals from the desired anatomical cardiac tissue region; or optical sensing components to detect physiological signals from the desired anatomical cardiac tissue region and electrical sensing components to detect physiological signals from the desired anatomical cardiac tissue region.

The secondary device housing 1200 may also include a detection circuit (not shown) to detect a phase timing of an external electromagnetic field such that the control circuit 1110 alters its operations to avoid interfering with the detected external electromagnetic field.

The secondary device housing 1200 may include sensors to detect a heart signal and to produce a sensor signal therefrom and a modulator to modulate the sensor signal to differentiate the sensor signal from electromagnetic interference. In the alternative, the secondary device housing 1200 may include sensors to detect a heart signal and to produce a sensor signal therefrom, and the primary device housing 1100 may include a sampling circuit to sample the sensor signal multiple times to differentiate the sensor signal from electromagnetic interference, undesirable acoustic signals, large muscle contractions, or extraneous infrared light.

The cardiac assist system illustrated in FIG. 30 may detect an electromagnetic interference insult upon the cardiac assist system, and upon detection, the control circuit 1110 places the cardiac assist system in an asynchronous mode. The control circuit 1110 places the cardiac assist system in the asynchronous mode for a duration of the electromagnetic interference insult and places the cardiac assist system in a synchronous mode upon detection of an absence of an electromagnetic interference insult. The electromagnetic interference insult may be detected a thermistor or other heat detector, a high frequency interference detector, a high voltage detector, or an excess current detector.

The cardiac assist system illustrated in FIG. 30 may also provide atrial monitoring and diagnostic functions to help physicians make more precise patient management decisions. The cardiac assist system illustrated in FIG. 30 can provide bradyarrhythmia therapies that treat patients with chronic heart problems in which the heart beats too slowly to adequately support the body's circulatory needs, in addition to the monitoring of the atria (upper chambers) and ventricles (lower chambers) to enable physicians to assess atrial rhythm control and ventricular rate control.

The cardiac assist system illustrated in FIG. 30 can also be used to provide daily atrial fibrillation measurements to assess atrial rhythm control. This information can improve a physician's ability to track disease progression, as well as the effectiveness of current device and drug therapies. The cardiac assist system illustrated in FIG. 30 can also be used to monitor of the ventricular rate during an atrial arrhythmia that helps assess ventricular rate control. This information can be viewed in a graphical snapshot format or by viewing the specific episode EGM information. The cardiac assist system illustrated in FIG. 30 can also be used to provide specific information on the frequency and duration of arrhythmias that help with risk assessment of symptoms and in determining whether a change in anticoagulation medicines is warranted.

Figure 27:
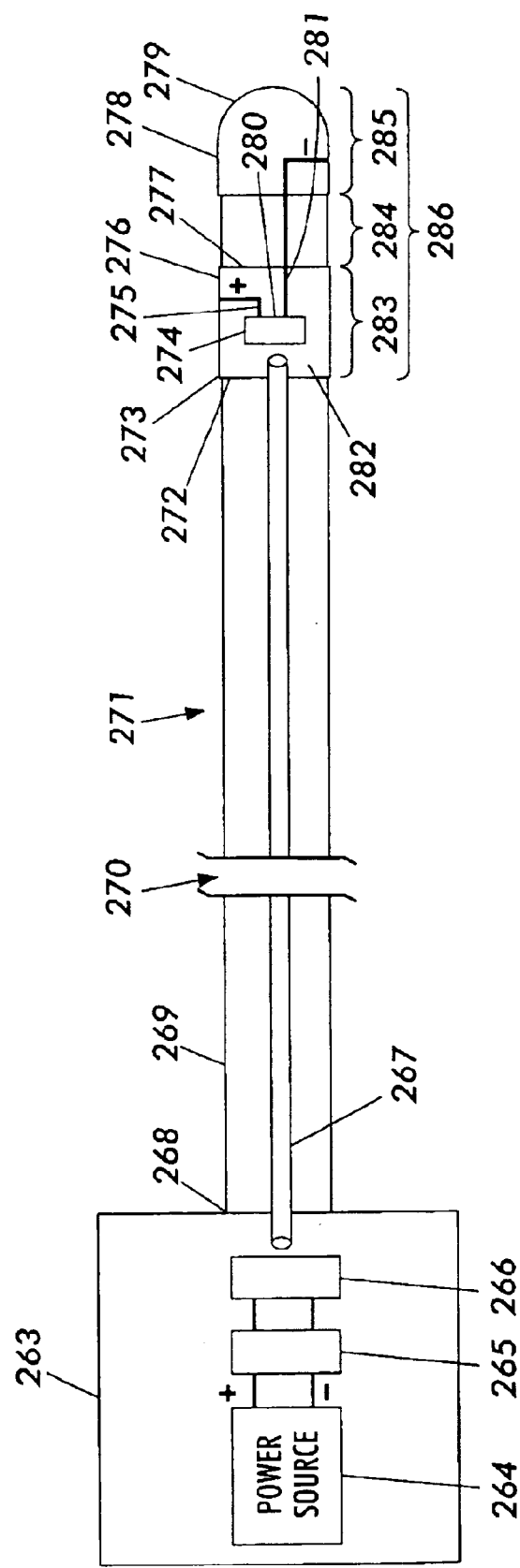
FIG. 27 is a partial view of a cardiac assist device according to some or all of the concepts of the present invention with an intermediate portion of the photonic catheter thereof removed for illustrative clarity.

FIG. 27 illustrates an MRI-compatible cardiac pacemaker according to another embodiment of the present invention. The pacemaker may be wearable and is readily implemented to operate in a fixed-rate (VOO) mode. The pacemaker includes a first (main) enclosure 263 that is designed to be located outside the body and connected to a proximal end 268 of a photonic catheter. A distal end 273 of a photonic catheter 271 mounts a bipolar endocardial (or pericardial) electrode pair 286 that includes a second enclosure 283 and a third enclosure 285 separated by a short insulative spacer 284. Other electrode configurations could also be used.

The main enclosure 263 houses a self-contained electrical power source 264, a pulse generator 265, and an electro-optical transducer 266. The power source 264, which may include one or more batteries, serves to deliver low energy continuous electrical power to the pulse generator. The pulse generator 265 stores the electrical energy provided by the power source 264 in one or more storage devices such as capacitors, batteries, etc., and periodically releases that energy to deliver electrical pulses to the electro-optical transducer 266. The electro-optical transducer 266 converts the electrical pulses into light energy and directs that energy into the proximal end 268 of the photonic catheter 271.

The main enclosure 263 is preferably formed as a sealed casing, external to the body, made from a non-magnetic metal. Note that a rate control selector and a pulse duration selector can be provided on the main enclosure 263 to allow a medical practitioner to controllably stress a patient's heart by varying the rate and duration of the stimulating pulses. Note further that if the power source 264 comprises multiple batteries, these may be separately wired for independent operation and a selector switch can be provided on the enclosure 263 to selectively activate each battery for use. A pair of illuminated push buttons may also be provided for testing each battery.

The photonic catheter 271 includes an optical conduction pathway 267 surrounded by a protective outer covering 269. The optical conduction pathway 267 may be constructed with one or more fiber optic transmission elements that are conventionally made from glass or plastic fiber material, e.g., a fiber optic bundle. To avoid body fluid incompatibility problems, the protective outer covering 269 should be made from a biocompatible material, such as silicone rubber, polyurethane, polyethylene, or other biocompatible polymer having the required mechanical and physiological properties. The protective outer covering 269 is thus a biocompatible covering. Insofar as the photonic catheter 271 must be adapted for insertion into the body, the biocompatible covering 269 is preferably a very thin-walled elongated sleeve or jacket having an outside diameter on the order of about 5 millimeters and preferably as small as one millimeter or even smaller. This will render the photonic catheter 271 sufficiently slender to facilitate insertion thereof through a large vein, such as the external jugular vein.

The proximal end 268 of the photonic catheter 271 is mounted to the main enclosure 263 using an appropriate connection. The optical conduction pathway 267 may extend into the enclosure 263 for a short distance, where it terminates in adjacent relationship with the electro-optical transducer 266 in order to receive light energy therefrom.

Light emitted by the electro-optical transducer 266 is directed into the proximal end 268 of the photonic catheter 271, and transmitted through the optical conduction pathway 267 to the second enclosure 283. Since the photonic catheter 271 is designed for optical transmission, it cannot develop magnetically induced or RF-induced electrical currents, as is the case with the metallic leads of conventional pacemaker catheters.

The second enclosure 283 houses an opto-electrical transducer 274, which converts light energy received from the distal end of the photonic catheter 271 into electrical energy. The electrical output side 280 of the opto-electrical transducer 274 delivers electrical pulses that drive the pacemaker's electrode pair 286.

The second enclosure 283 is a hermetically sealed casing made from a non-magnetic metal, such as titanium, a titanium-containing alloy, platinum, a platinum-containing alloy, or any other suitable metal, including copper plated with a protective and compatible coating of the foregoing materials. Plated copper is especially suitable for the second enclosure 283 because it has a magnetic susceptibility approaching that of the human body, and will therefore minimize MRI image degradation. Note that the magnetic susceptibility of human body tissue is very low, and is sometimes diamagnetic and sometimes paramagnetic. As an alternative to using non-magnetic metals, the second enclosure 283 can be formed from an electrically conductive non-metal that preferably also has a very low magnetic susceptibility akin to that of the human body. Non-metals that best approach this condition include conductive composite carbon and conductive polymers comprising silicone, polyethylene, or polyurethane.

Unlike the main enclosure 263, the second enclosure 283 is adapted to be implanted via insertion in close proximity to the heart, and in electrical contact therewith. As such, the second enclosure 283 preferably has a miniaturized tubular profile that is substantially co-equal in diameter with the photonic catheter 271.

Figure 28:
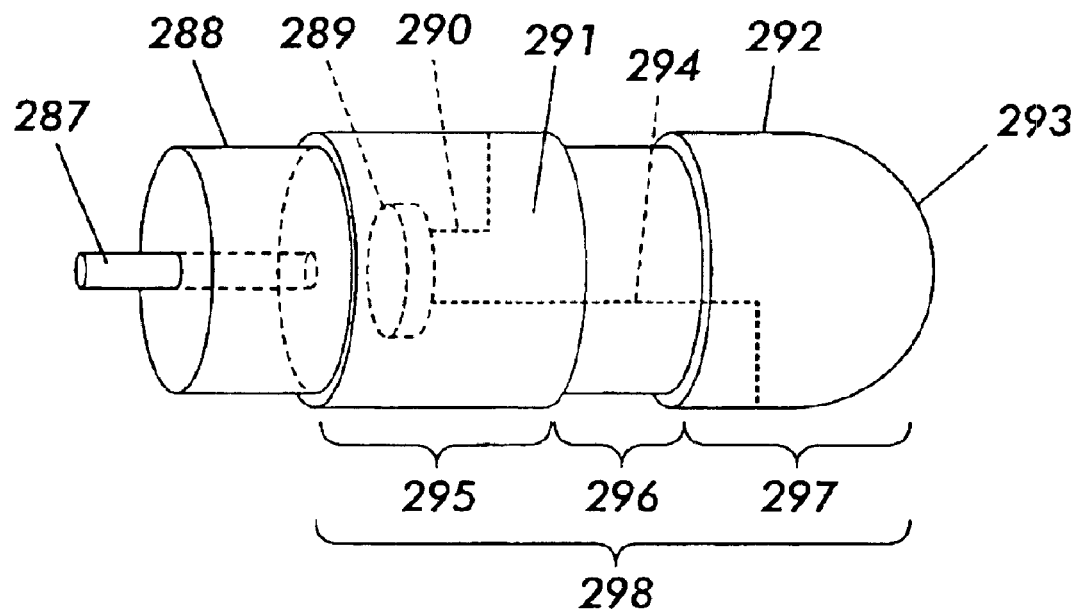
FIG. 28 is an enlarged partial perspective view of components located at the distal end of the photonic catheter FIG. 27.

As seen In FIGS. 27 and 28, the second enclosure (283, 295) includes a cylindrical outer wall 276 and a pair of disk-shaped end walls 272 and 277. The end wall 272 is mounted to the distal end 273 of the photonic catheter 271 using an appropriate sealed connection that prevents patient body fluids from contacting the optical conduction pathway 267 and from entering the second enclosure (283, 295). Although the photonic catheter 271 may feed directly from the main enclosure 263 to the second enclosure (283, 295), another arrangement would be to provide an optical coupling 270 at an intermediate location on the photonic catheter 271. The coupling 270 could be located so that a distal portion of the photonic catheter 271 that connects to the second enclosure 283 protrudes a few inches outside the patient's body. A proximal portion of the photonic catheter 271 that connects to the main enclosure 263 would then be connected when MRI scanning is to be performed. Note that the main enclosure 263 could thus be located a considerable distance from the patient so as to be well outside the area of the MRI equipment, as opposed to being mounted on the patient or the patient's clothing.

In an alternative arrangement, the coupling 270 could be located at the main enclosure 263. The optical conduction pathway 267 may extend into the enclosure (283, 295) for a short distance, where it terminates in adjacent relationship with the opto-electrical transducer (274, 289) in order to deliver light energy thereto. Light received by the opto-electrical transducer (274, 289) will thus be converted to electrical energy and delivered to the output side 280 of the opto-electrical transducer (274, 289).

Due to the miniature size of the second enclosure (283, 295), the opto-electrical transducer (274, 289) needs to be implemented as a miniaturized circuit. However, such components are conventionally available from commercial electronic component manufacturers. Note that the opto-electrical transducer (274, 289) also needs to be adequately supported within the second enclosure (283, 295).

To that end, the second enclosure (283, 295) can be filled with a support matrix material 291 that may be the same material used to form the photonic catheter's biocompatible covering 269 (e.g., silicone rubber, polyurethane, polyethylene, or any biocompatible polymer with the required mechanical and physiological properties).

As stated above, the second enclosure (283, 295) represents part of an electrode pair (286, 298) that delivers the electrical output of the pacemaker to a patient's heart. In particular, the electrode pair (286, 298) is a tip/ring system and the second enclosure (283, 295) is used as an endocardial (or pericardial) ring electrode thereof. A positive output lead (275, 290) extending from the electrical output side 280 of the opto-electrical transducer (274, 289) is electrically connected to the cylindrical wall 276 of the second enclosure (283, 295), as by soldering, welding or the like. A negative output lead (281, 294) extending from the electrical output side 280 of the opto-electrical transducer (274, 289) is fed out of the second enclosure (283, 295) and connected to a third enclosure (285, 297), which functions as an endocardial tip electrode of the electrode pair (286, 298).

The third enclosure (285, 297) can be constructed from the same non-magnetic metallic material, or non-metal material, used to form the second enclosure (283, 295). Since it is adapted to be inserted in a patient's heart as an endocardial tip electrode, the third enclosure (285, 297) has a generally bullet shaped tip (279, 293) extending from a tubular base end (278, 292). The base end (278, 292) preferably has an outside diameter that substantially matches the diameter of the second enclosure (283, 295) and the photonic catheter 271. Note that the base end (278, 292) of the third enclosure (285, 297) is open insofar as the third enclosure (285, 297) does not house any critical electrical components. Indeed, it mounts only the negative lead (281, 294) that is electrically connected to the third enclosure's base end (278, 292), as by soldering, welding, or the like.

The material used to form the spacer (284, 296) preferably fills the interior of the second enclosure (283, 295) so that there are no voids and so that the negative lead (281, 294) is fully captured therein.

Figure 29:
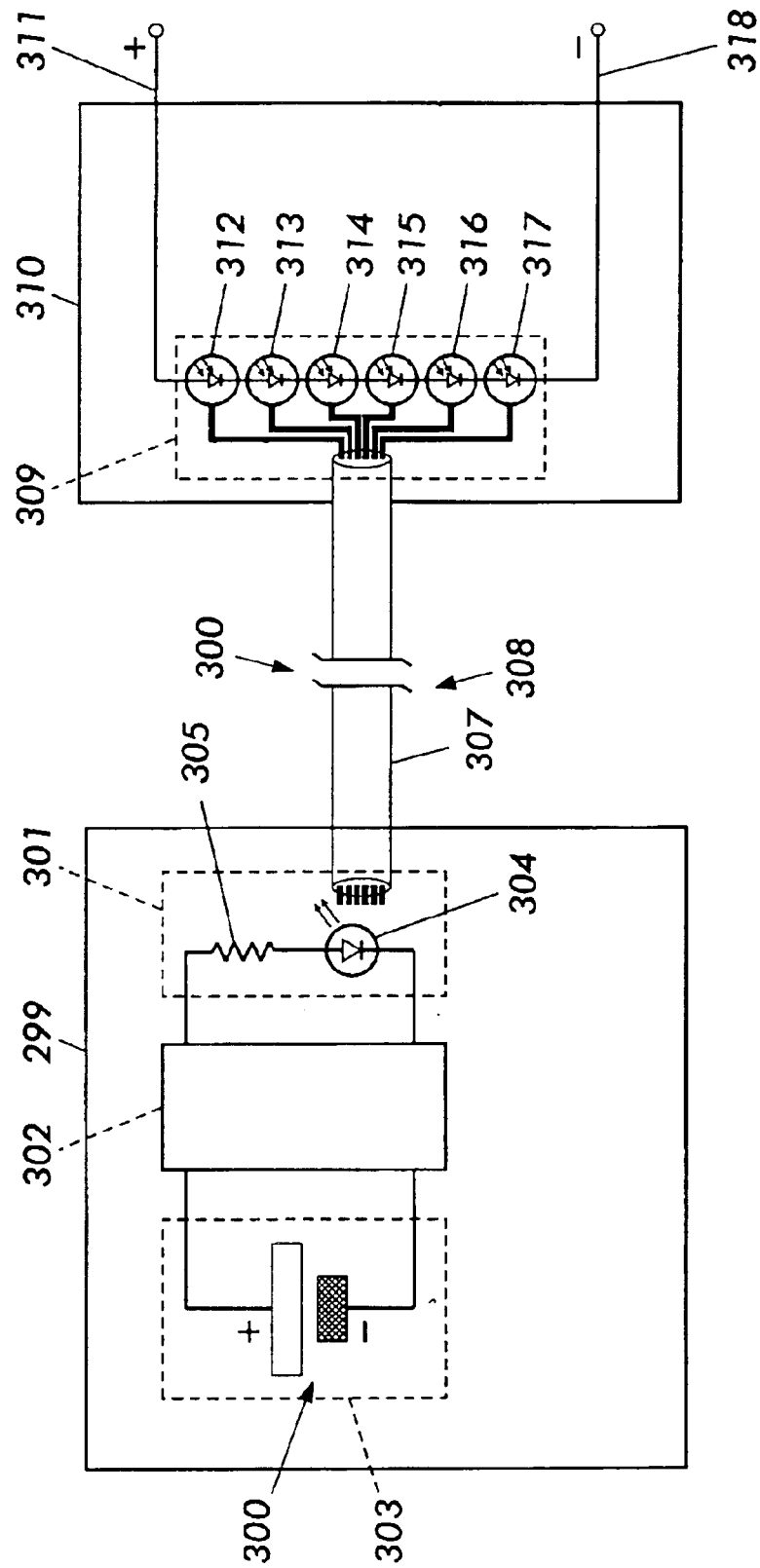
FIG. 29 is a detailed partial schematic view showing one construction of an electro-optical transducer according to some or all of the concepts of the present invention.

In FIG. 29, electrical power source 303 is implemented using a pair of conventional pacemaker lithium batteries 300 providing a steady state DC output of about 3 to 9 volts. Electro-optical transducer 301 is implemented with light emitting or laser diodes 304 and current limiting resistors 305. The diodes 304 are conventional in nature and thus have a forward voltage drop of about 2 volts and a maximum allowable current rating of about 50–100 milliamperes, or more. If additional supply voltage is available from the power source 20 (e.g., 4 volts or higher), more than one diode can be used in the electro-optical transducer for additional light energy output. The value of each resistor 305 is selected accordingly.

By way of example, if the batteries 300 produce 3 volts and the desired current through a single diode is 0.5 milliamperes, the value of the resistor should be about 2000 ohms. This would be suitable if the diode is a light emitting diode. If the diode were a laser diode, other values and components would be used. For example, a current level on the order of 100 milliamps may be required to produce coherent light output from the diode if it is a laser. The optical conduction pathway 300 can be implemented as fiber optic bundles 307, or as single fibers, driving respective arrays of photo diodes. The opto-electrical transducer 28 may be implemented with six photodiodes 312–317 that are wired for photovoltaic operation.

The opto-electrical transducer 309 may be implemented with a single photodiode that is wired for photovoltaic operation. The photodiodes are suitably arranged so that each respectively receives the light output of one or more fibers of the fiber optic bundles and is forward biased into electrical conduction thereby.

Each photodiode is conventional in nature and thus produces a voltage drop of about 0.6 volts. Cumulatively, the photodiodes develop a voltage drop of about 3.3 volts across the respective positive and negative inputs a power amplifier (not shown). The photodiode develops about 0.6 volts across the respective positive and negative inputs of the power amplifier.

Figure 40:
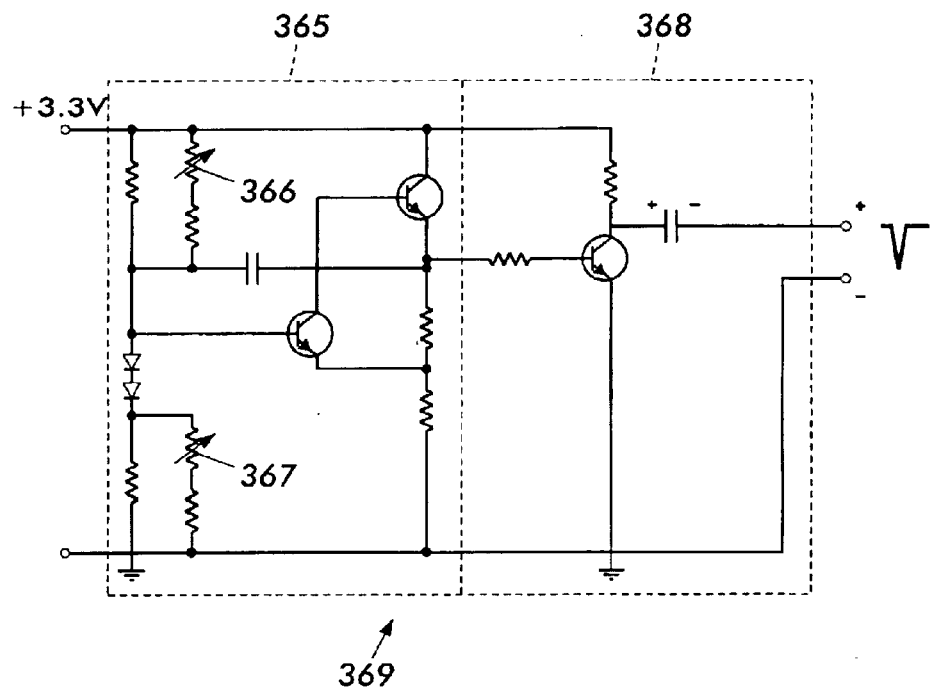
FIGS. 40 through 42 are schematic circuit diagrams of a pulse generator according to some or all of the concepts of the present invention.
Figure 41:
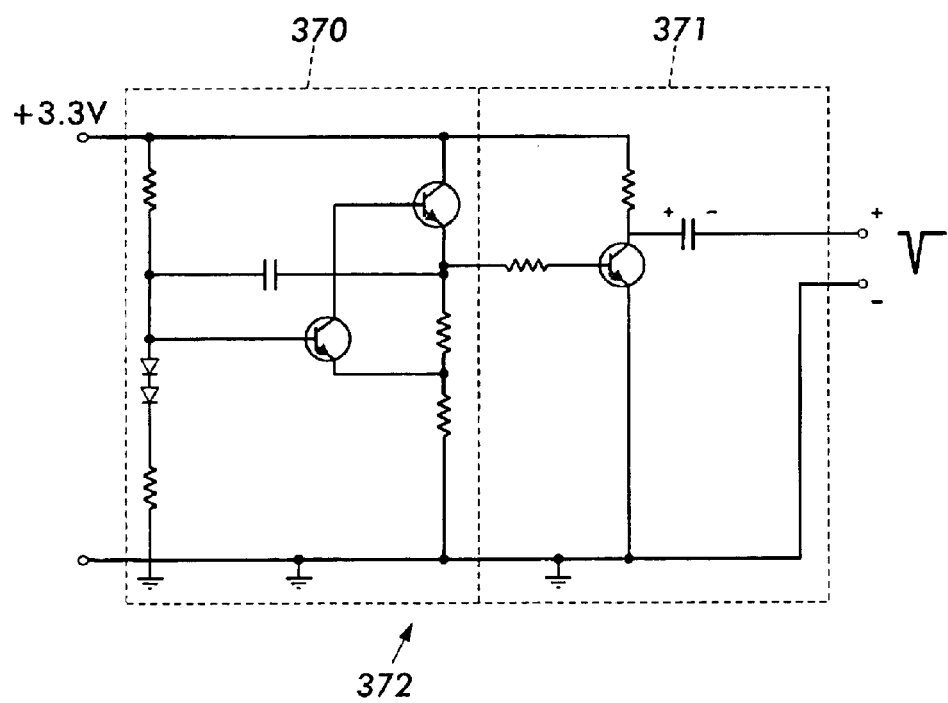
Figure 42:
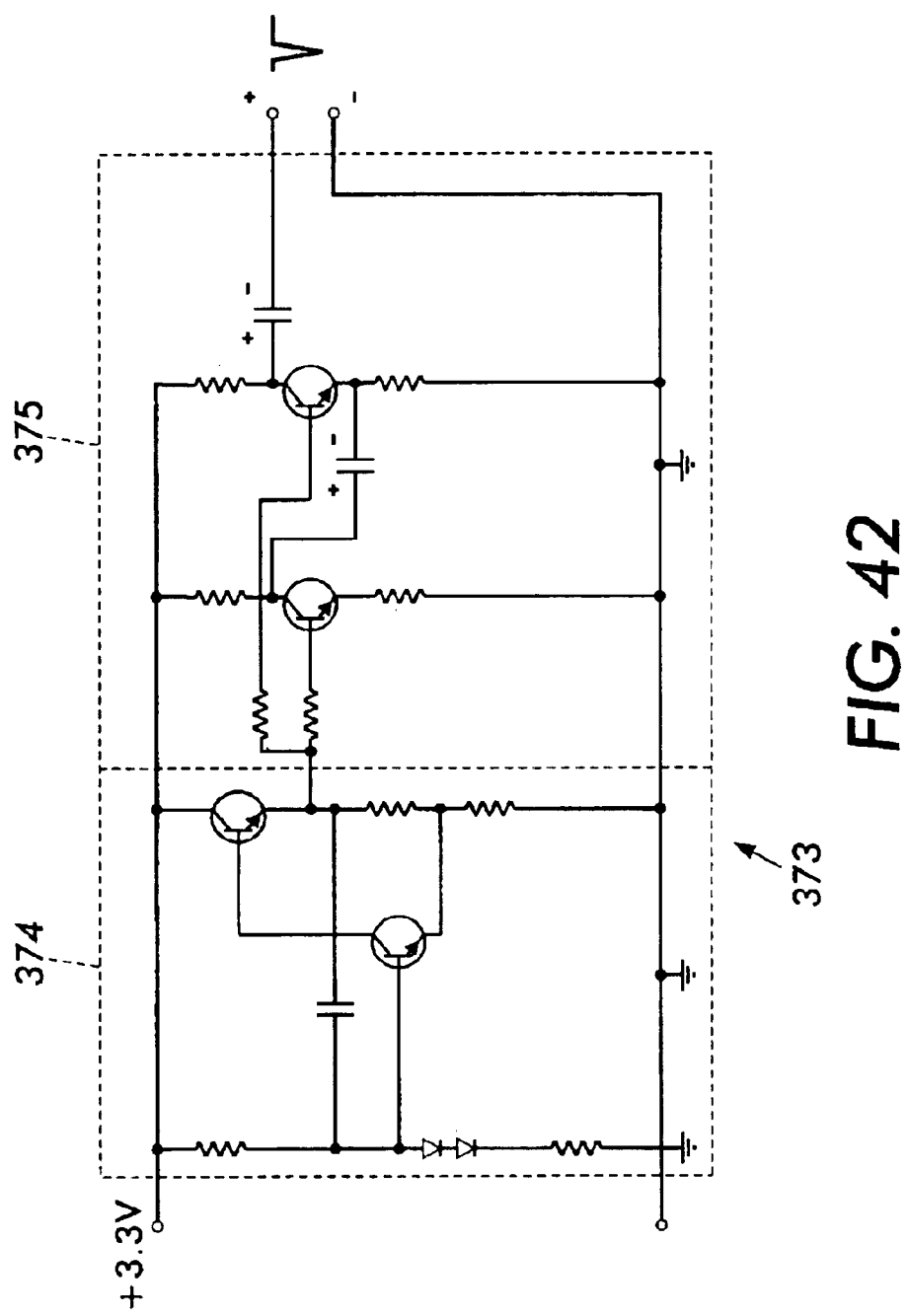

FIGS. 40–42 and 49 shows an alternative circuit configuration that may be used to implement the oscillator (369, 372, 373, 439) and the power amplifier. The alternative circuit configurations are conventional in nature and do not constitute part of the present invention per se. The alternative circuit configurations are presented herein as examples of pulsing circuits that have been shown to function well in a pacemaker environment. In FIGS. 40–42, the oscillator (369, 372, 373, 439) is a semiconductor pulsing circuit (365, 370, 374, 441) of the type disclosed in U.S. Pat. No. 3,508,167. As described in U.S. Pat. No. 3,508,167, the contents of which are incorporated herein by reference, the pulsing circuit (365, 370, 374, 441) forming the oscillator (369, 372, 373, 439) provides a pulsewidth and pulse period that are relatively independent of load and supply voltage. The semiconductor elements are relegated to switching functions so that timing is substantially independent of transistor gain characteristics. In particular, a shunt circuit including a pair of diodes is connected so that timing capacitor charge and discharge currents flow through circuits that do not include the base-emitter junction of a timing transistor.

Figure 46:
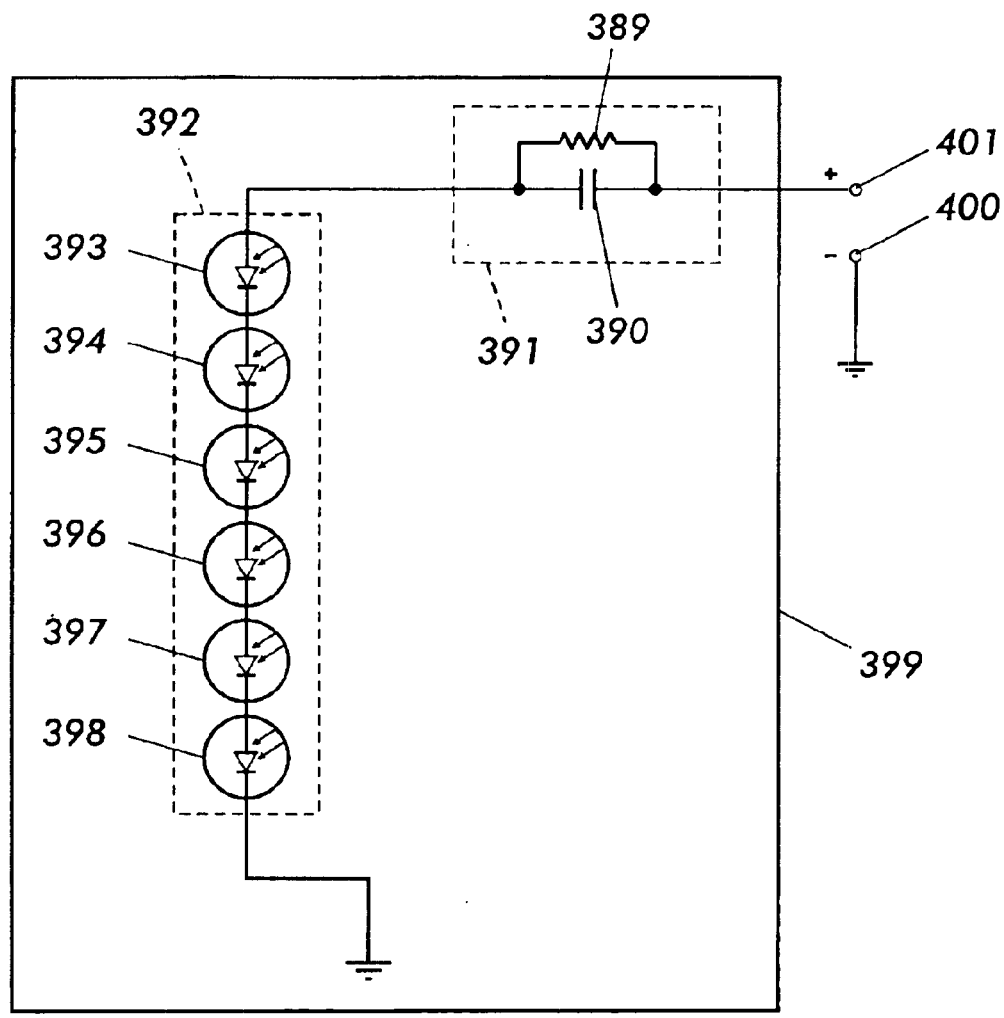
FIG. 46 is a schematic circuit diagram showing a second embodiment of an opto-electric coupling device in accordance with the invention.

In FIG. 46, an opto-electrical coupling device 399 is shown. The opto-electrical coupling device includes opto-electrical transducer 392. A high quality capacitor 390 delivers pulses from the opto-electrical transducers photo-diode array (393–398) to a tip electrode 401. A return path is provided from a ring electrode 400. The capacitor 390 forms part of a DC current discharge system 391 that also includes a resistor 389. The resistor 389 is connected across the capacitor 390 to discharge it between pulses.

Exemplary values for the capacitor 390 and the resistor 389 are 10 microfarads and 20 K ohms, respectively.

Figure 47:
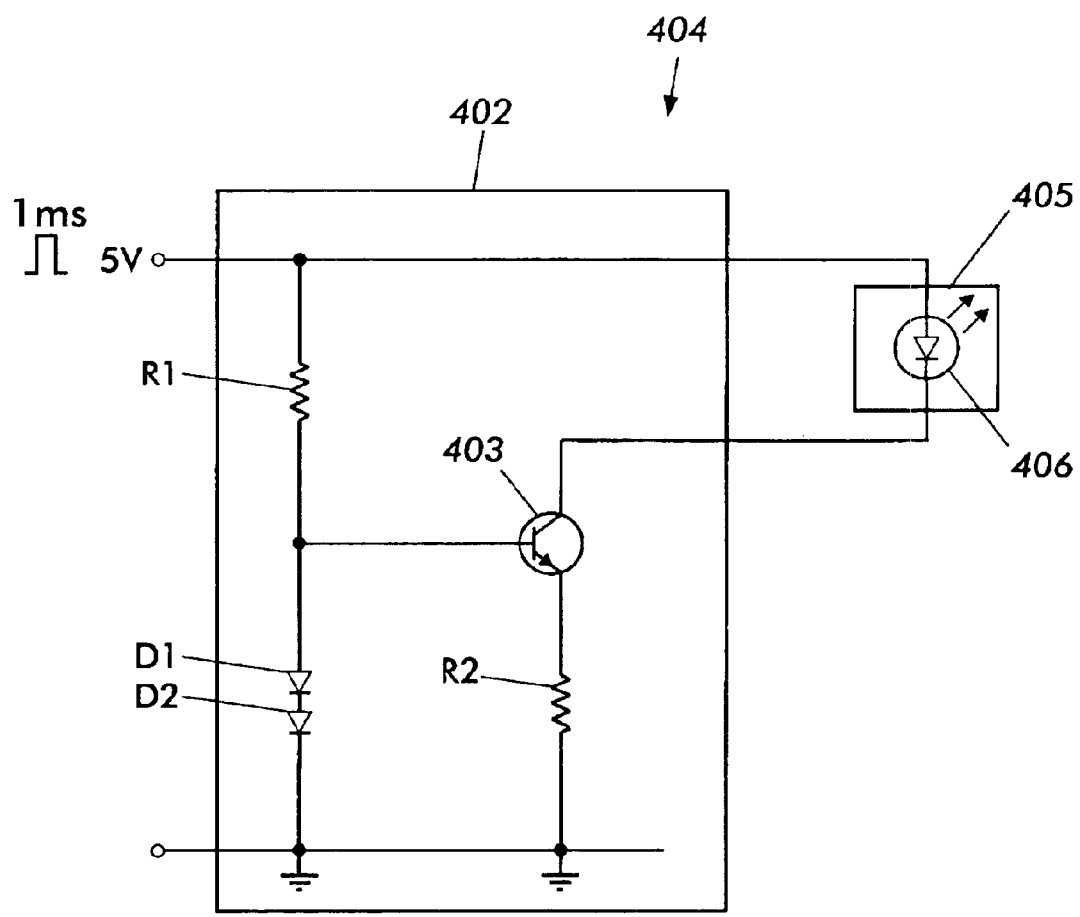
FIG. 47 is a schematic circuit diagram showing a constant current regulator for a laser light generator according to some or all of the concepts of the present invention.

In FIG. 47, a constant current regulator 402 is shown. The purpose of the constant current regulator 402 is to controllably drive the electro-optical transducer 405 using the electrical pulse output of a pulse generator. Collectively, the constant current regulator 402 and the electro-optical transducer 405 provide a constant current regulated laser light generator 404. The current regulator 402 uses an NPN transistor 403 arranged in a common emitter configuration to drive the laser diode 404. A suitable NPN transistor that may be used to implement the transistor 403 is a switching transistor.

The laser diode 404 can be implemented as a standard 150 milliwatt gallium arsenide laser diode. The recommended power level for driving such a device is about 100 milliwatts. The required input voltage is about 2 volts. Assuming there is a conventional diode voltage drop of about 0.7 volts across the laser diode 404, a driving current of about 140 milliamps should be sufficient to achieve operation at the desired 100 milliwatt level. However, the current through the laser diode 404 must be relatively constant to maintain the desired power output. The constant current regulator 402 achieves this goal.

In particular, the base side of the transistor 403 is biased through a resister R1 and a pair of diodes D1 and D2. The diodes D1 and D2 are connected between the base of the transistor 403 and ground. Each has a conventional diode voltage drop of about 0.7 volts, such that the total voltage drop across the diodes D1 and D2 is about 1.5 volts and is substantially independent of the current through the diodes (at operational current levels). This means that the base of the transistor 403 will be maintained at a relatively constant level of about 1.5 volts notwithstanding changes in the input voltage supplied from the pulse generator. The value of the resistor R1 is selected to be relatively high to reduce the current draw through the base of the transistor 403. By way of example, a value of 2500 ohms may be used for R1. Assuming a supply voltage of about 5 volts, as represented by the input pulse waveform, the current through the resistor R1 will be a negligible 1.4 milliamps.

Importantly, the emitter side of the transistor 403 will remain at a relatively constant level of about 1 volt (assuming a base-emitter voltage drop across the transistor 403 of about 0.5 volts). A resistor R2 is placed between the emitter of the transistor 403 and ground in order to establish a desired current level through the collector-emitter circuit of the transistor 403. Note that this also represents the driving current through the laser diode 404 insofar as the laser diode is connected in series between the current regulator's supply voltage (the output of pulse generator) and the collector of the transistor 406. Since the voltage potential at the transistor emitter is about 1 volt, if R2 is selected to be a 7 ohm resistor, the resultant current level will be about 140 milliamps. This corresponds to the current level required to drive the laser diode 404 at the desired operational power level.

Figure 48:
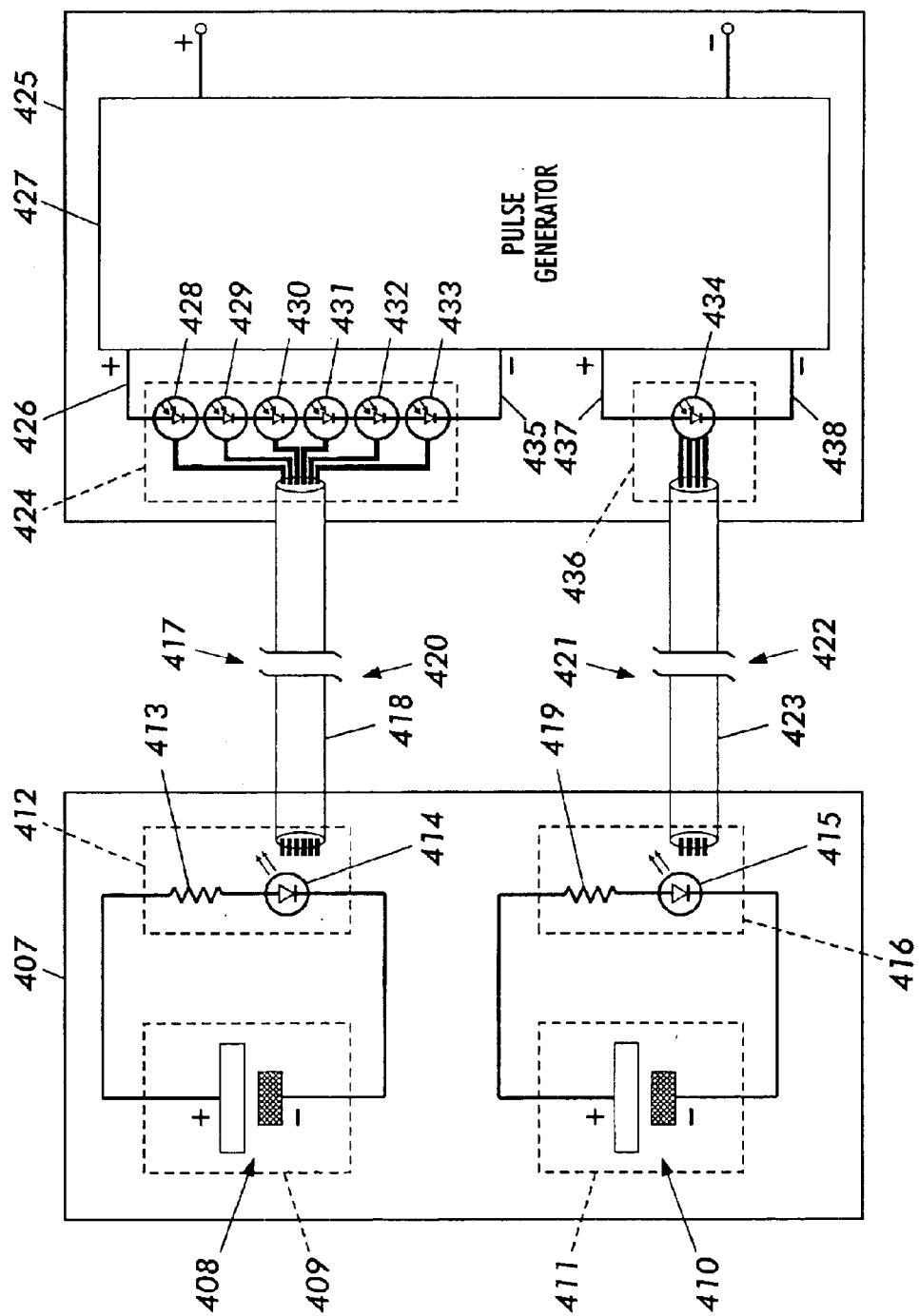
FIG. 48 is a detailed partial schematic view showing one construction of an electro-optical transducer according to some or all of the concepts of the present invention.
Figure 49:
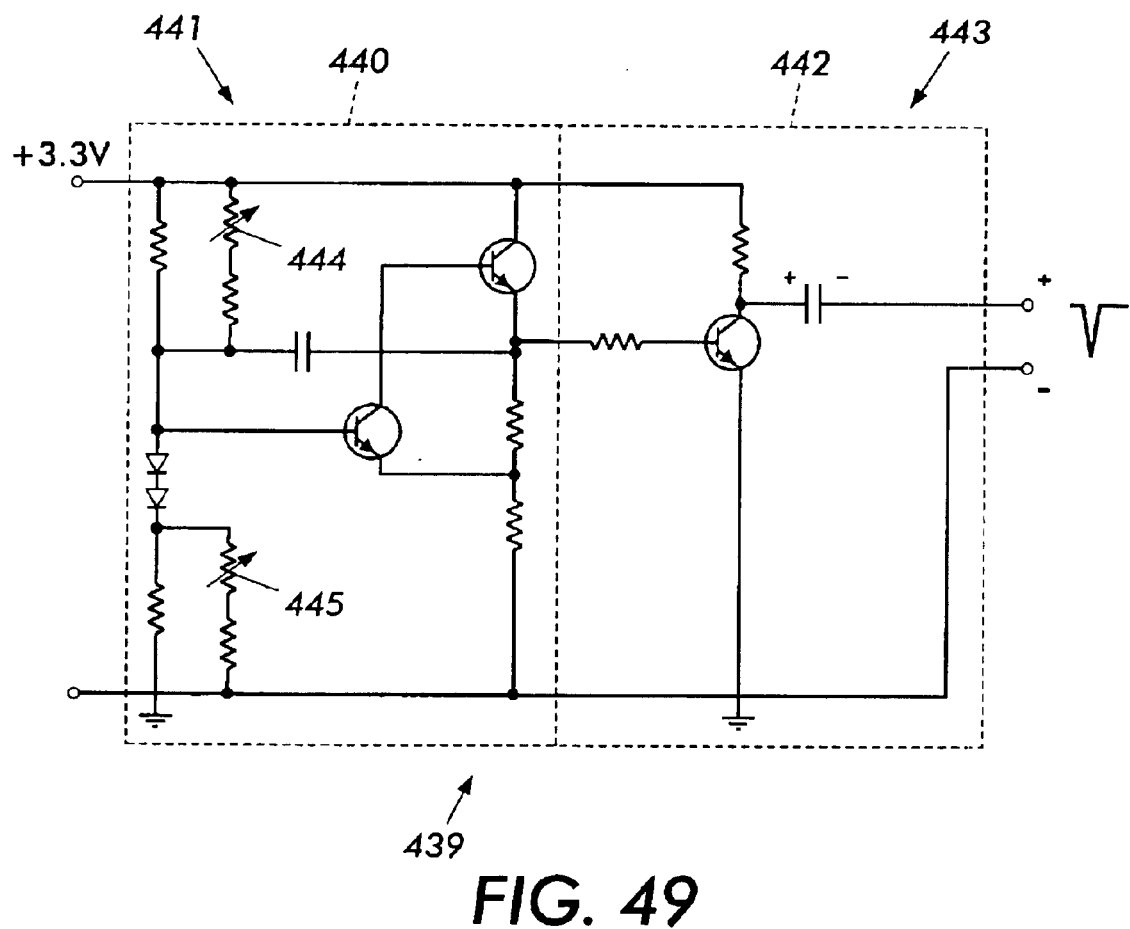
FIG. 49 is a schematic circuit diagram of a pulse generator according to some or all of the concepts of the present invention.

In FIG. 48, an electrical power source (409, 411) is implemented using a pair of conventional pacemaker lithium batteries (408, 410) providing a steady state DC output of about 3 to 9 volts. The electro-optical transducers 412 and 416 are implemented with light emitting or laser diodes (414, 415) and current limiting resistors (413, 419). The diodes are conventional in nature and thus have a forward voltage drop of about 2 volts and a maximum allowable current rating of about 50–100 milliamps, or more. If additional supply voltage is available from the power source (409, 411) (e.g., 4 volts or higher), more than one diode can be used in each electro-optical transducer 412 and 416 for additional light energy output. The value of each resistor is selected accordingly.

By way of example, if the batteries produce 3 volts and the desired current through a single diode is 0.5 milliamps, the value of the resistor should be about 2000 ohms. This would be suitable if the diode is a light emitting diode. If the diode were a laser diode, other values and components would be used. For example, a current level on the order of 100 milliamps may be required to produce coherent light output from the diode if it is a laser. The optical conduction pathways 417 and 421 can be implemented as fiber optic bundles 418 and 423, or as single fibers, driving respective arrays of photodiodes.

The opto-electrical transducer 424 may be implemented with six photodiodes 428–433 that are wired for photovoltaic operation. The opto-electrical transducer 424 may be implemented with a single photodiode 434 that is wired for photovoltaic operation. The photodiodes are suitably arranged so that each respectively receives the light output of one or more fibers of the fiber optic bundles 418 and 423 and is forward biased into electrical conduction thereby.

Each photodiode is conventional in nature and thus produces a voltage drop of about 0.6 volts. Cumulatively, the photodiodes 428–433 develop a voltage drop of about 3.3 volts across the respective positive and negative inputs 426 and 435 of the power amplifier 427. The photodiode 434 develops about 0.6 volts across the respective positive and negative inputs 437 and 438 of the power amplifier 427.

Figure 43:
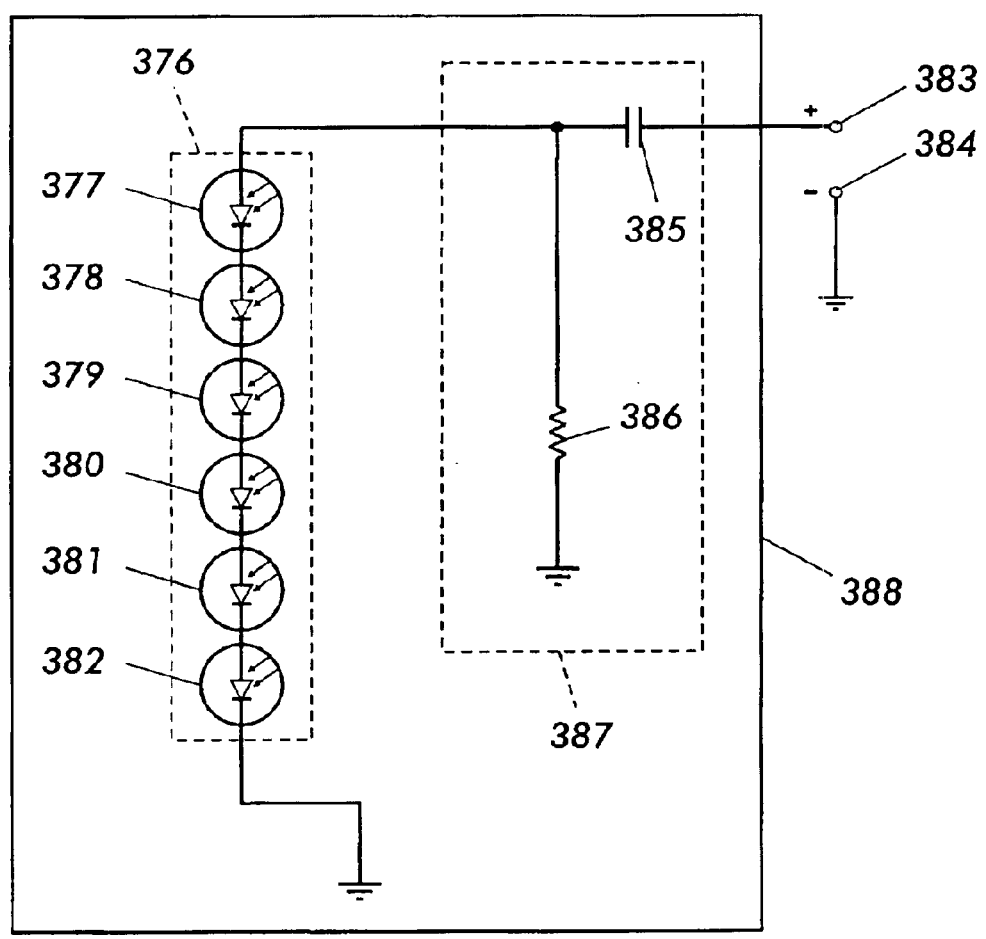
FIG. 43 is a schematic circuit diagram showing one embodiment of an opto-electric coupling device according to some or all of the concepts of the present invention.

In FIG. 43, a circuit diagram of an opto-electric coupling device 388 is shown. The opto-electric coupling device 388 includes the opto-electrical transducer 376, which is assumed to be illuminated by a photonic catheter for about 1 millisecond, and left dark for about 1000 milliseconds. When illuminated, opto-electrical transducer photodiode array 377–382 will produce pulses of about 3 to 4 volts across its outputs. The positive side of the photodiode array is connected via a high quality capacitor 385 to an implantable tip electrode 383 that is adapted to be implanted in the endocardium of a patient. The negative side of the photodiode array is connected to an implantable ring electrode 384 that is adapted to be immersed in the blood of the patient's right ventricle. A DC current discharge system 387 comprising the capacitor 385 and a resistor 386 is used to attenuate DC current in the tissue implanted with the electrodes 383 and 384.

The resistor 386 is connected across the outputs of the photodiode array. The resistor 386 thus grounds one side of the capacitor 385 between pulses. The return path from the implanted tissue is the through the ring electrode 384.

The values of the capacitor and the resistor are selected so that the opto-electric coupling device conveys a suitable stimulating signal to the electrodes, but in such a manner as to prevent any net DC current from flowing into the implanted tissue. A long RC time constant is desired so that the square waveform of the photodiode array output is delivered in substantially the same form to the implanted tissue. For a 1 millisecond pulse, the desired RC time constant should be substantially larger than 1 millisecond. By way of example, if the capacitor has a capacitance of 10 microfarads and the resistor has a resistance of 20 K ohms, the RC time constant will be 200 milliseconds. This is substantially larger than the 1 millisecond pulse length produced by the photodiode array.

On the other hand, the RC time constant should not be so large as to prevent adequate DC current flow from the implanted body tissue into the capacitor between pulses. According to design convention for RC circuits, a period of five time constants is required in order for an RC circuit capacitor to become filly charged. Note that the selected RC time constant of 200 milliseconds satisfies this requirement if the photodiode array is pulsed at 1000 millisecond intervals, which is typical for pacemakers. Thus, there will be approximately five 200 millisecond time constants between every pulse. Stated another way, the RC time constant will be approximately one-fifth of the time interval between successive pulses.

Figure 44:
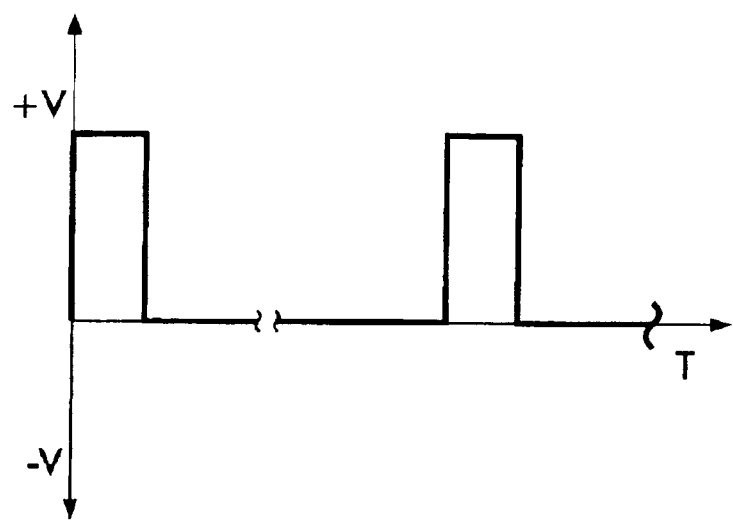
FIGS. 44 and 45 are graphical illustrations of pulse waveforms that may be, respectively, input to and output from the opto-electric coupling device according to some or all of the concepts of the present invention.
Figure 45:
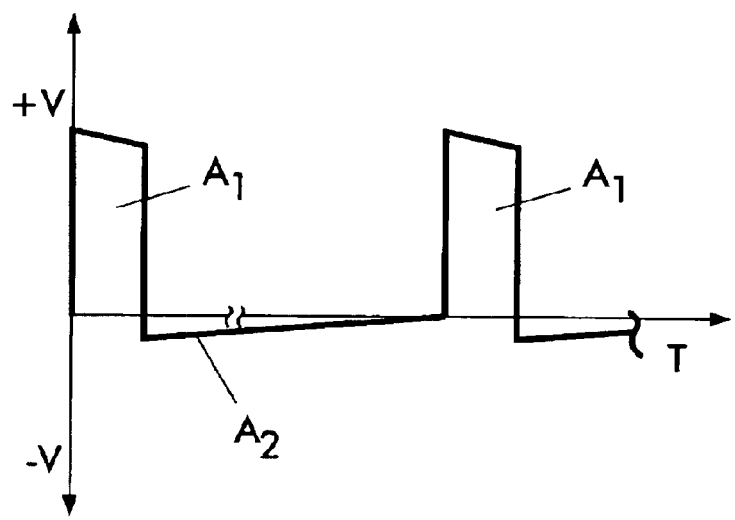

FIG. 44 shows the square wave electrical pulses generated by the photodiode array. FIG. 45 shows the actual electrical pulses delivered at the electrodes due to the presence of the RC circuit provided by the capacitor and the resistor. Note that the pulses of FIG. 45 are substantially square is shape due to the RC circuit's time constant being substantially larger than the input pulse width. FIG. 45 further shows that there is a small reverse potential between pulses that counteracts DC current build up in the stimulated tissue.

Ideally, the area $A_1$ underneath each positive pulse of FIG. 45 will be equal to the area $A_2$ of negative potential that follows the positive pulse.

Another embodiment of the present invention is the use of a photonic catheter in a MRI environment to sense the biological conditions of particular tissue regions of a patient or to stimulate particular tissue regions of the patient. Examples of photonic catheters are illustrated in FIGS. 5 through 20.

Figure 5:
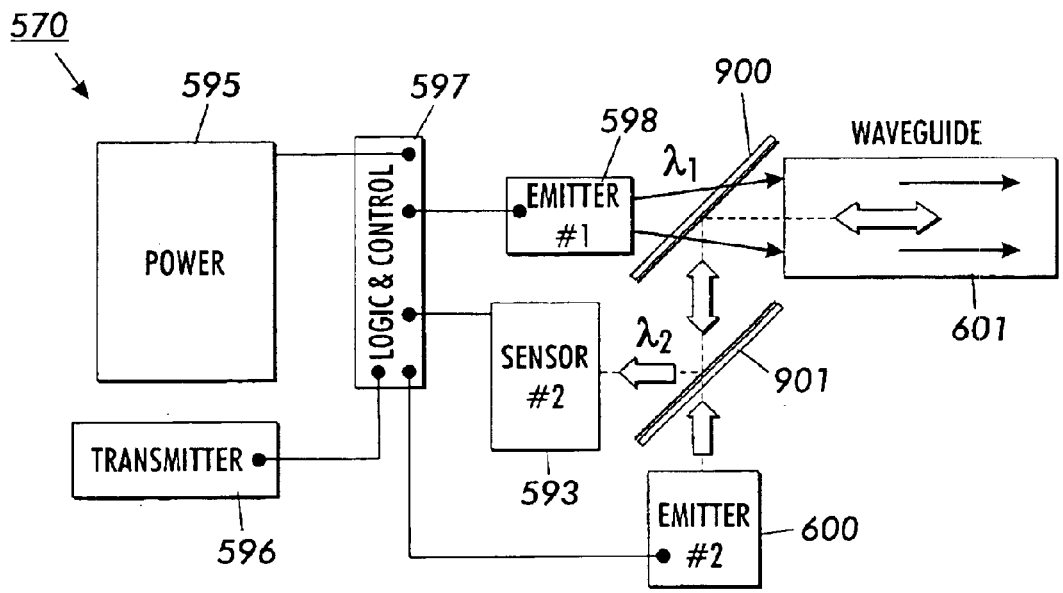
FIGS. 5 through 20 are schematics of various optical sensing devices according to some or all of the concepts of the present invention.
Figure 6:
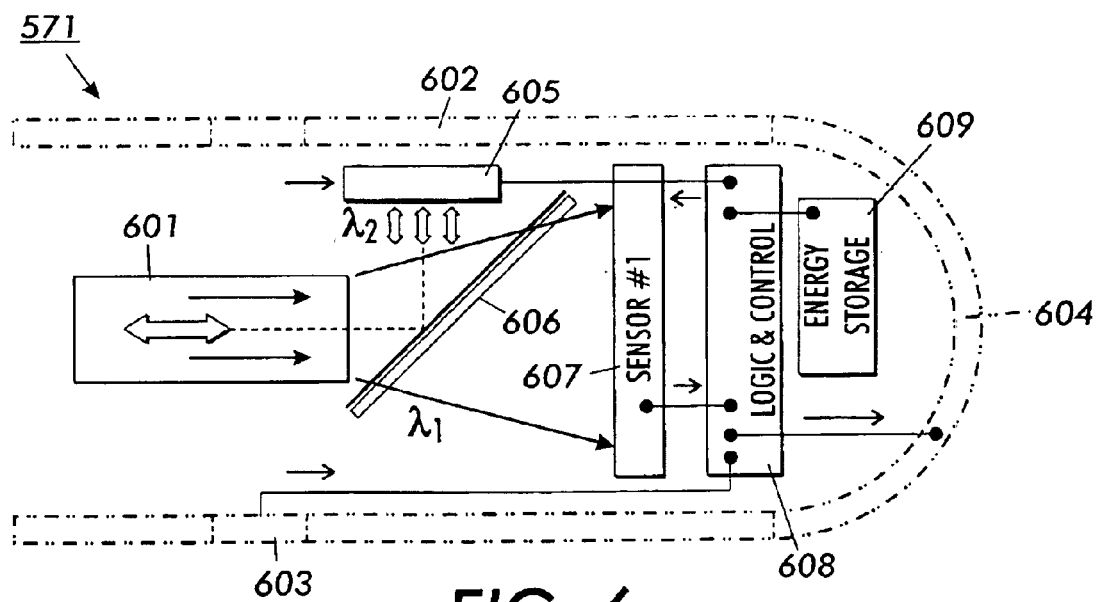

In FIGS. 5 and 6, power supply 595 and logic and control unit 597 enable emitter 598 to transmit radiation, preferably optical radiation at wavelength $\lambda_1$ through beam splitter 900 into wave-guide 601. This radiation exits the wave-guide 601 and passes through beam splitter 606 to sensor 607 that converts the radiation to electrical energy. The electrical energy is used to directly power functions at the distal end of lead 602, such as stimulation of internal body tissues and organs (e.g. pacing of cardiac tissues) through electrodes 604 and 603. The electrical energy is also used to power logic and control unit 608 or is stored in energy storage device 609 (e.g. a capacitor) for later use. Proximally located elements are electrically connected through conductors. Distally located sensor 607, logic and control unit 608, energy storage device 609, and electrodes (604, 603) are electrically connected through conductive elements.

A second emitter 600 transmits radiation at wavelength $\lambda_2$ ($\lambda_2 \neq \lambda_1$) through beam splitter 901, off beam splitter 900, into wave-guide 601, to beam splitter 606 and optical attenuator 605 that is mounted on a mirror. The optical attenuator 605 is preferably made from materials such as liquid crystals whose optical transmission density is modulated by applied electrical voltage. The distally located logic and control unit 608 and optical attenuator 605 are powered either directly by excitation radiation or from energy stored in energy storage element 609.

This photonic catheter can also be used with electrodes 603 and 604 to capture electrical signals from the patient and direct the captured electrical signals to logical and control unit 608 which uses electrical energy to modulate the optical transmission density of optical attenuator 605. Attenuated optical signals, originally emanating from emitter 600, are encoded with the electrical signals received by electrodes 603 and 604 by passing through the optical attenuator 605, reflect off mirror, travel back through the optical attenuator 605, reflect off beam splitter 606 and into wave-guide 601 to beam splitters 900 and 901 to sensor 599 that converts the encoded optical signal to an encoded electrical signal. Output from sensor 599 is sent to logic and control unit 597. This output is either utilized by logic and control unit 597 to control the radiation from emitter 598, which is typically at a high energy level and is used to stimulate distally located tissues and organs, or is relayed to transmitter 596 which relays this sensory information to external sources.

Figure 7:
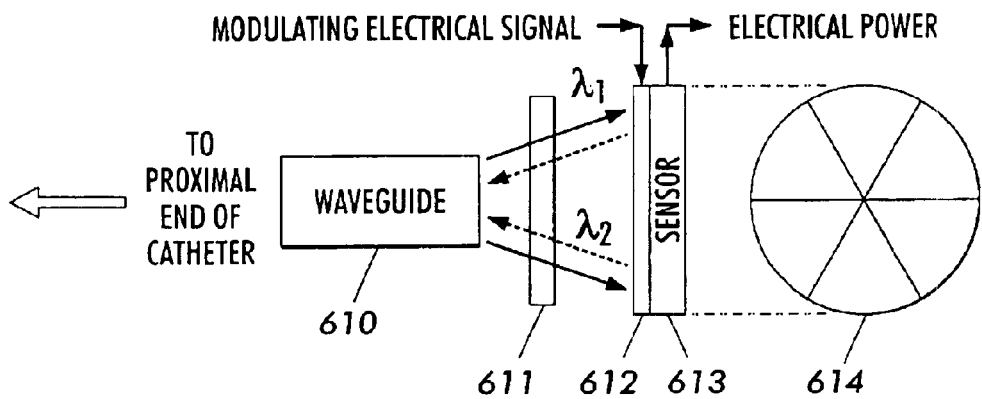

The embodiment illustrated in FIG. 7 is similar to the embodiment illustrated in FIGS. 5 and 6, with the exception that the optical attenuator 612 is mounted over the surface of the distally located sensor 613 to take advantage of the first surface reflectance of this sensor. Radiation emitted by wave-guide 610 passes through optical attenuator 612 to sensor 613 that converts the radiation to electrical energy as previously described. Radiation emitted by wave-guide 610 passes through optical attenuator 612 and reflects off the front surface of sensor 613. This reflected energy is collected by coupling lens 611 that directs the energy into wave-guide 610 to a sensor at the proximal end (not shown).

Figure 8:
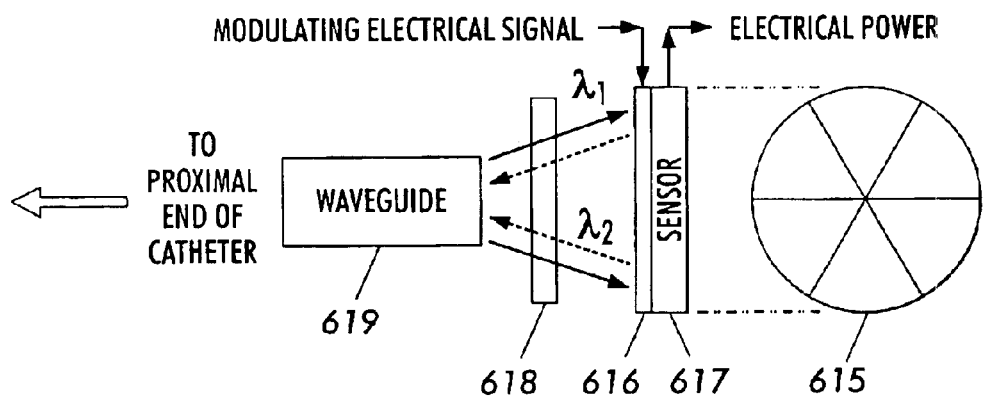

The embodiment illustrated in FIG. 8 is similar to the embodiment illustrated in FIGS. 5 and 6, with the exception that a variable reflectance optical reflector 616 is mounted over the surface of the distally located sensor 617. Radiation emitted by wave-guide 619 passes through optical reflector 616 to sensor 617 that converts the radiation to electrical energy as previously described. Radiation emitted by wave-guide 619 is reflected off optical reflector 616 and is collected by coupling lens 618 that directs the energy into wave-guide 619. Preferably, the variable reflectance optical reflector 616 would be transparent to excitation radiation.

Figure 9:
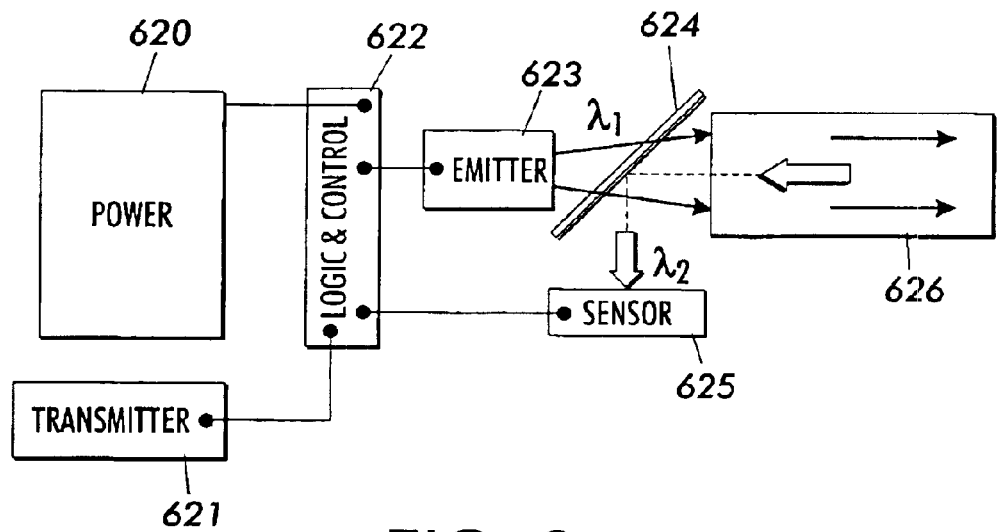
Figure 10:
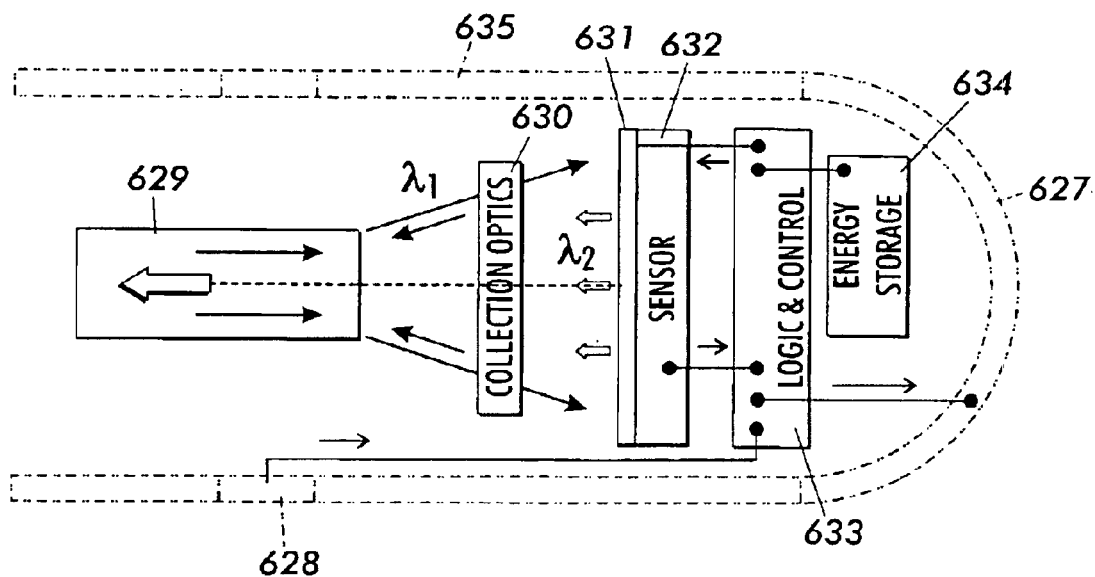

With respect to FIGS. 9 and 10, power supply 620 and logic and control unit 622 enable emitter 623 to transmit radiation, preferably optical $\lambda_1$ radiation at wavelength XI through beam splitter 624 into wave-guide 626. This radiation exits the wave-guide and passes through an on-axis variable intensity optical emitter 631 to sensor 632 that converts the radiation to electrical energy. The electrical energy is used to directly power functions at the distal end of lead 635, such as stimulation of internal body tissues and organs (e.g. pacing of cardiac tissues) through electrodes 627 and 628; to power logic and control unit 633; or to store in energy storage device 634 (e.g. a capacitor) for later use. Proximally located elements are electrically connected through conductors. Distally located sensor, logic and control unit, energy storage device, and electrodes are electrically connected through conductive elements.

Logic and control unit 633 receives sensor input from electrodes 627 and 628 and delivers an electrical potential to variable intensity optical emitter 631 causing it to emit optical radiation at wavelength $\lambda_2$ ($\lambda_2 \neq \lambda_1$) which is collected by coupling lens 630 and directed into wave-guide 629, to beam splitter 624 and sensor 625. The distally located logic and control unit 633 and optical attenuator 631 are powered either directly by excitation radiation or from energy stored in energy storage element 634.

This photonic catheter can also be used with electrodes 627 and 628 to capture electrical signals from the patient and direct the captured electrical signals to logical and control unit 633 that uses electrical energy to modulate the variable intensity optical emitter 631. Optical signals, emanating from variable intensity optical emitter 631, are encoded with the electrical signals received by electrodes 627 and 628 and travel into wave-guide 629 to beam splitter 624 to sensor 625 that converts the encoded optical signal to an encoded electrical signal. Output from sensor 625 is sent to logic and control unit 622. This output is either utilized by logic and control unit 622 to control the radiation from emitter 623, which is typically at a high energy level and is used to stimulate distally located tissues and organs, or is relayed to transmitter 621 which relays this sensory information to external sources.

Figure 11:
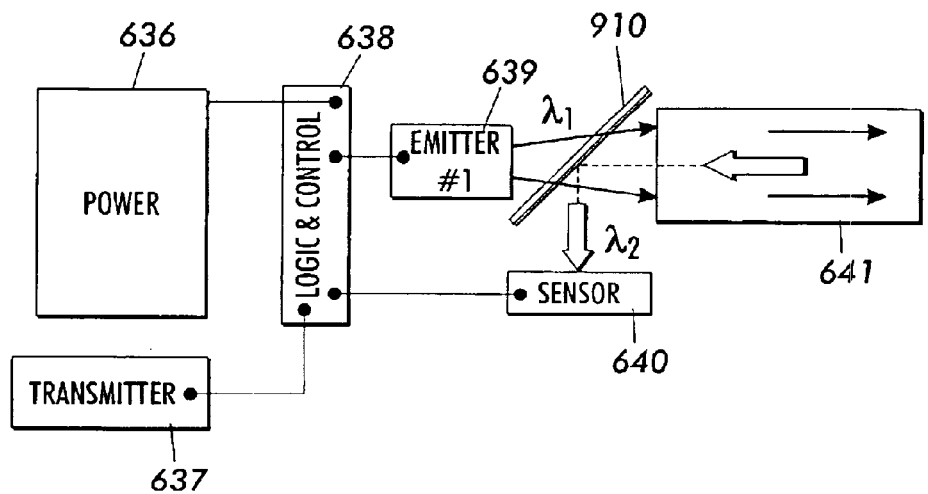
Figure 12:
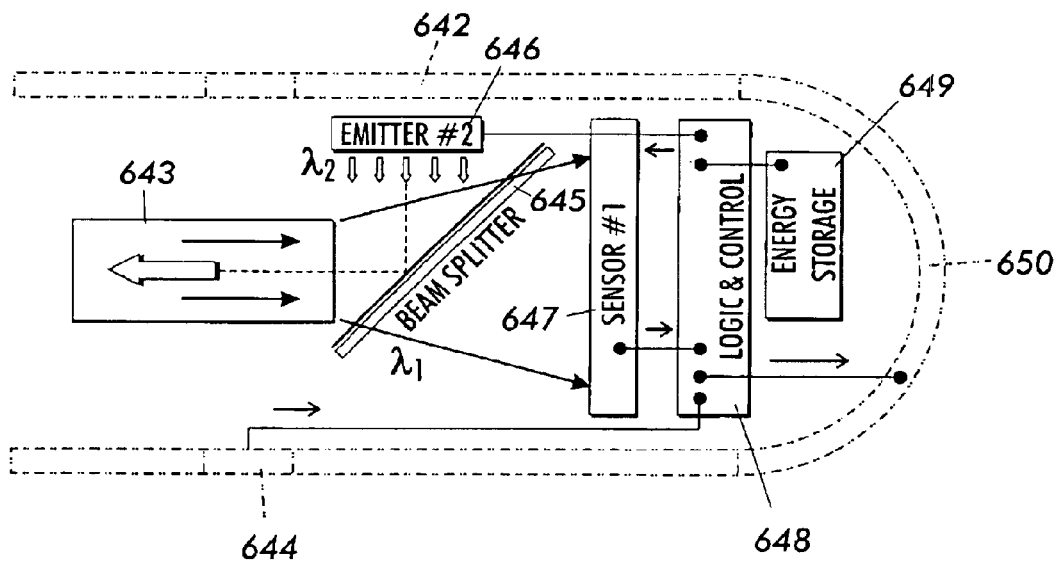

The embodiment illustrated in FIGS. 11 and 12 is similar to the embodiment illustrated in FIGS. 9 and 10, with the exception that the variable intensity optical emitter 646 is located off-axis. Power supply 636 and logic and control unit 638 enable emitter 639 to transmit radiation, preferably optical radiation at wavelength $\lambda_1$ through beam splitter 910 into wave-guide 641. This radiation exits the wave-guide 643 and passes through beam splitter 645 to sensor 647 that converts the radiation to electrical energy. The electrical energy is used to directly power functions at the distal end of lead 642, such as stimulation of internal body tissues and organs (e.g. pacing of cardiac tissues) through electrodes 650 and 644; power logic and control unit 648; or to be stored in energy storage device 649 (e.g. a capacitor) for later use.

Proximally located elements are electrically connected through conductors. Distally located sensor 647, logic and control unit 648, energy storage device 649, and electrodes 650 and 644 are electrically connected through conductive elements. Variable intensity emitter 646 transmits radiation at wavelength $\lambda_2$ ($\lambda X_2 \neq \lambda_1$) off beam splitter 645 into wave-guide 643 and off beam splitter 910 to sensor 640. Preferably, the variable intensity emitter 646 emits optical radiation when excited by an electrical potential, and is mounted upon a mirror to direct a greater percentage of emissions into wave-guide 643.

A preferred application of the embodiment illustrated in FIGS. 11 and 12 uses electrodes 650 and 644 to capture electrical signals and direct them to logical and control unit 648 which delivers electrical energy to emitter 646 to emit optical radiation that is encoded with the electrical signals received by electrodes 650 and 644. The encoded optical signals are directed to beam splitter 645 and into wave-guide 643 to sensor 640 that converts the encoded optical signal to an encoded electrical signal. Output from sensor 640 is sent to logic and control unit 638. This output is either utilized by logic and control unit 638 to control the radiation from emitter 639, which is typically at a high energy level (typically higher than radiation from emitter 646) and is used to stimulate distally located tissues and organs, or is relayed to transmitter 637 that relays this sensory information to external sources.

Figure 13:
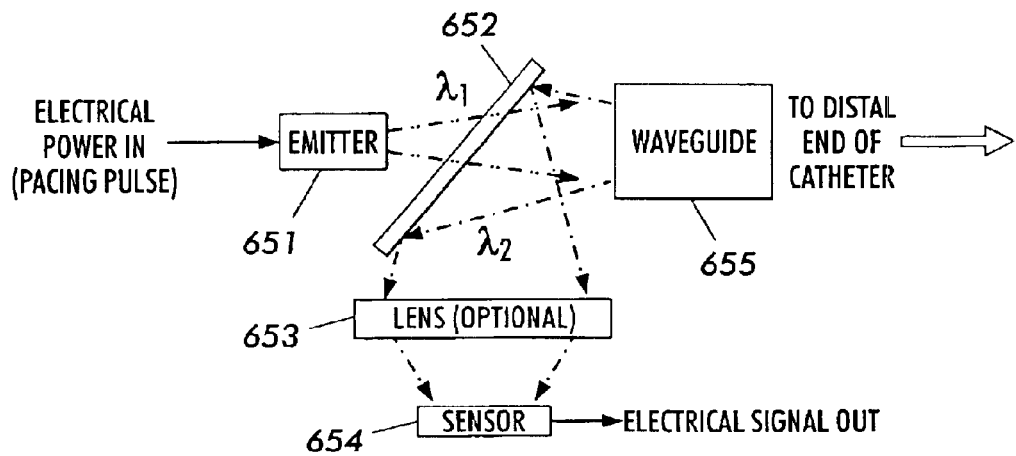
Figure 14:
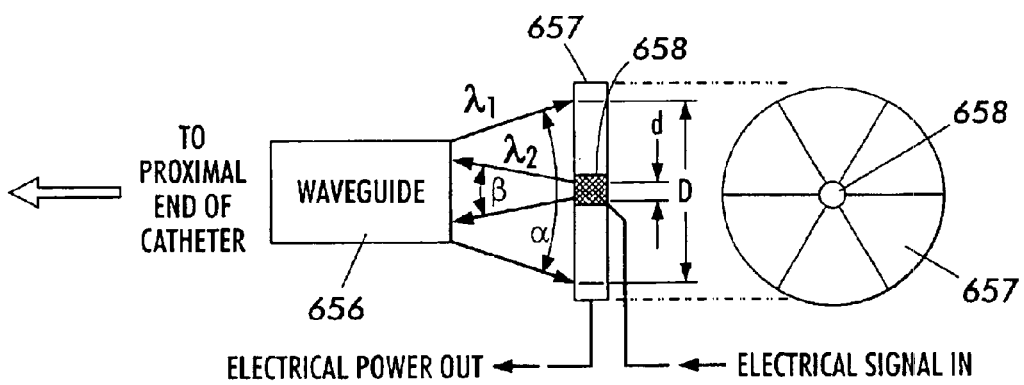

In FIGS. 13 and 14, radiation emitter 651 transmits radiation, preferably optical radiation at wavelength $\lambda_1$ through beam splitter 652 into wave-guide 655. This radiation exits wave-guide 656 at exit angle α and impinges upon sensor 657 that converts the radiation to electrical energy. The electrical energy is used as previously described. Proximally and distally located elements are electrically connected through conductors.

A second emitter 658 located on or within sensor 657 transmits radiation at wavelength $\lambda_2$ ($\lambda_2 \neq \lambda_1$) at cone angle β into wave-guide 656 to beam splitter 652. The small size 'd' of emitter 658 relative to the larger size 'D' of sensor 658 and narrow radiation exit angle α and emission angle β enable effective coupling of radiation from emitter 651 into sensor 657 and radiation from emitter 658 into wave-guide 656. Optional coupling lens 653 collects and directs radiation to sensor 654. The distally located light source may be a solid-state laser or light emitting diode.

Figure 15:
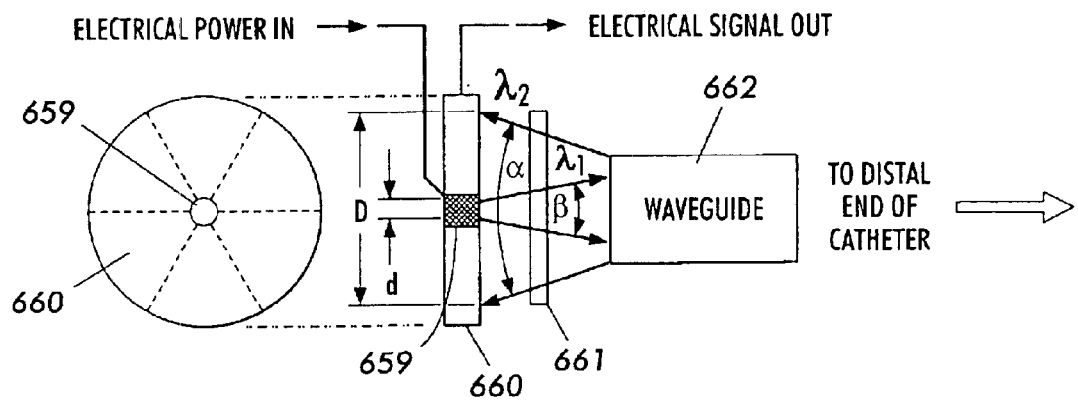
Figure 16:
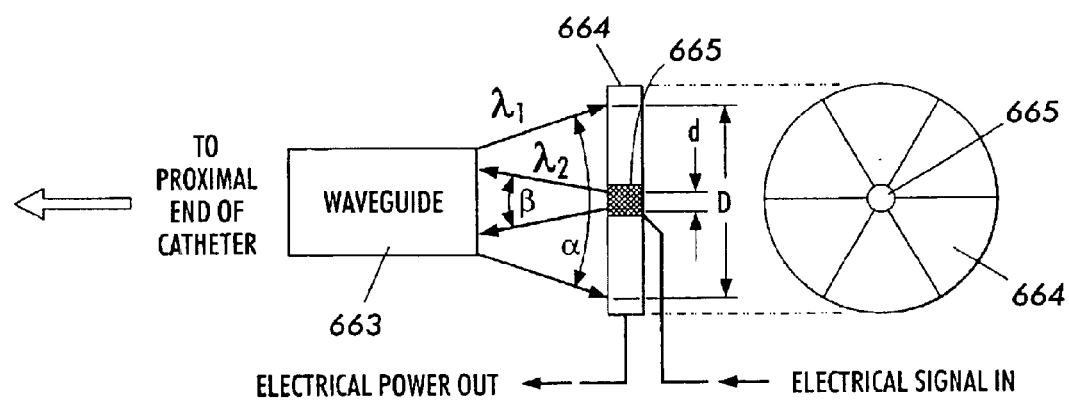

In FIGS. 15 and 16, radiation emitter 659 transmits radiation, preferably optical radiation at wavelength $\lambda_1$ and exit angle $\beta_1$ through optional coupling lens 661 into wave-guide 662. This radiation exits wave-guide 663 at exit angle $\alpha_1$ and impinges upon sensor 664 that converts the radiation into electrical energy. The electrical energy is used as previously described.

A second emitter 665 located on or within sensor 664 transmits radiation at wavelength $\lambda_2$ at cone angle $\beta_2$ into wave-guide 663. This radiation exits wave-guide 662 at exit angle $\alpha_2$ onto sensor 660. Ideally, wavelength $\lambda_2 \neq \lambda_1$ so that optical reflections from coupling lens 661 or wave-guide 662 do not interfere with radiation incident upon detector 660. The small sizes 'd' of emitters 659 and 665 relative to the larger sizes 'D' of sensors 660 and 664, combined with narrow radiation exit angles $\alpha_1$ and $\alpha_2$, and $\beta_1$ and $\beta_2$, enable effective coupling of radiation into wave-guide (662, 663), and sensors 660 and 664.

Figure 17:
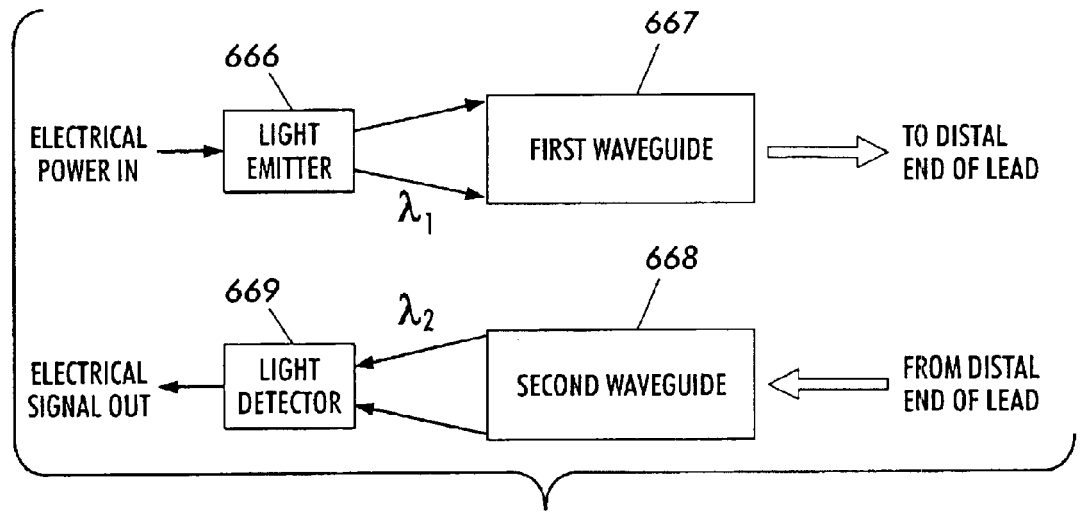
Figure 18:
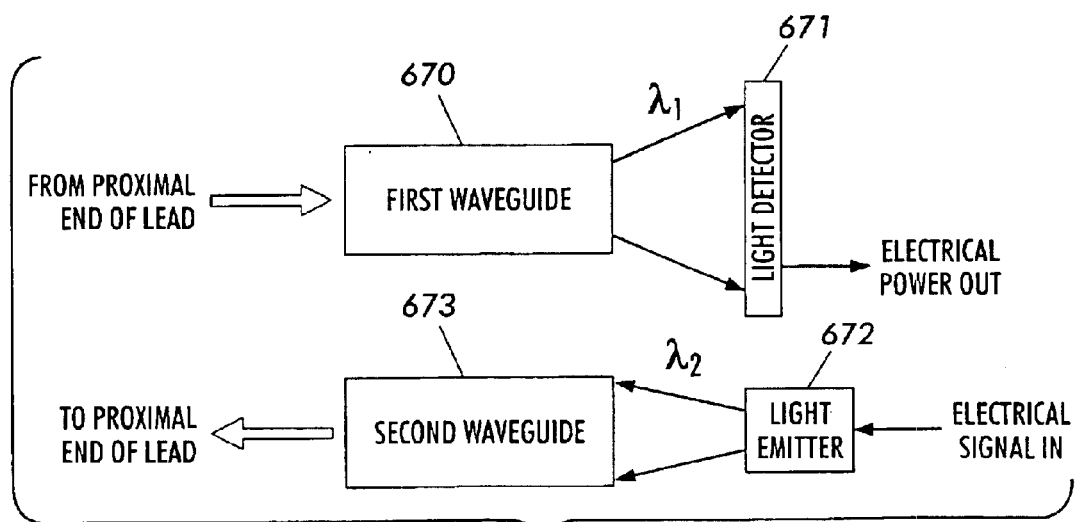

In FIGS. 17 and 18, radiation emitter 666 transmits radiation, preferably optical radiation at wavelength $\lambda_1$ into wave-guide 667. This radiation exits wave-guide 670 and impinges upon sensor 671 that converts the radiation into electrical energy. The electrical energy is used as previously described.

A second distally located emitter 672 transmits radiation at wavelength $\lambda_2$ into wave-guide 673. This radiation exits wave-guide 668 onto proximally located sensor 669. Wavelength $\lambda_2$ may or may not be equal to wavelength $\lambda_1$. Light sources 666 and 672 include a solid-state laser or light emitting diode. Wave-guides (667, 670) and (668, 673) are preferably included in the same lead assembly.

Figure 19:
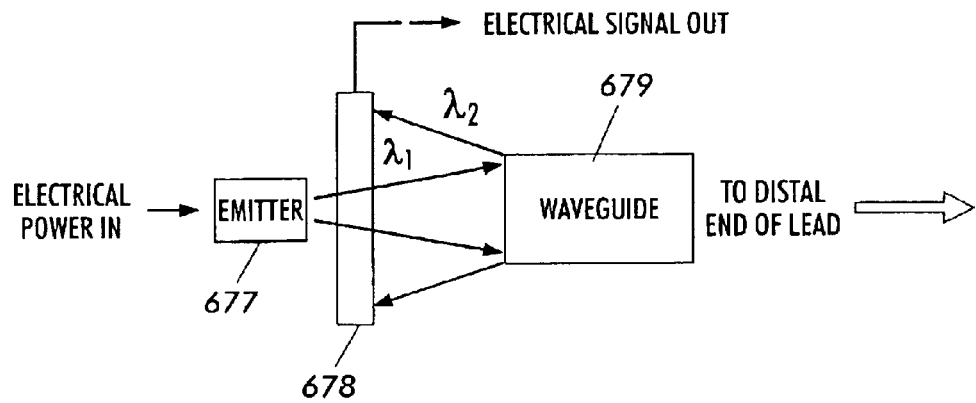
Figure 20:
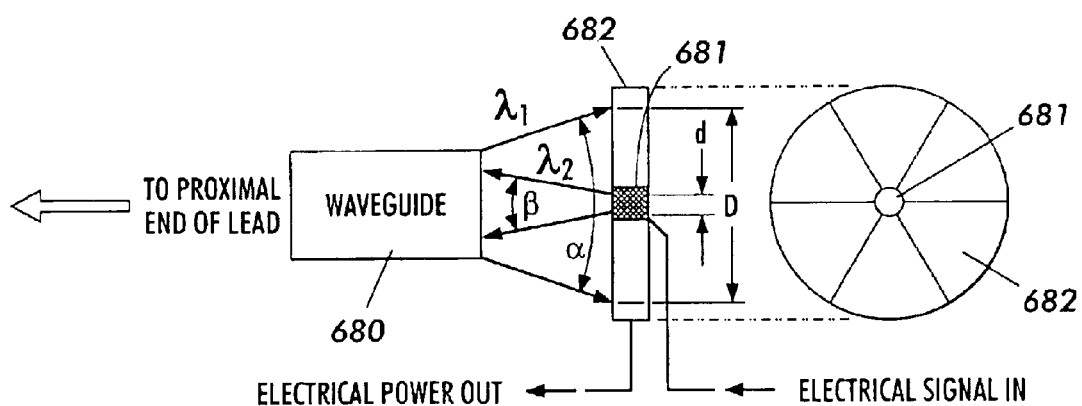

In FIGS. 19 and 20, a sensor 678 transparent to certain wavelengths of optical radiation is used. Radiation emitter 677 transmits radiation, preferably optical radiation at wavelength $\lambda_1$ through sensor 678 that is transparent to wavelength $\lambda_1$ into wave-guide 679 and exiting at exit angle α to sensor 682 that converts the radiation to electrical energy. The electrical energy is used as previously described.

A second emitter 681 located on or within sensor 682 transmits radiation at wavelength $\lambda_2$ ($\lambda_2 \neq \lambda_1$) at cone angle β into wave-guide 680 to proximally located sensor 678 where it is absorbed and converted into electrical energy. As before, the small size 'd' of emitter 681 relative to the larger size 'D' of sensor 682 and narrow radiation exit angle α and emission angle β enable effective coupling of radiation from emitter 677 into sensor 682 and radiation from emitter 681 into wave-guide 680.

Figure 50:
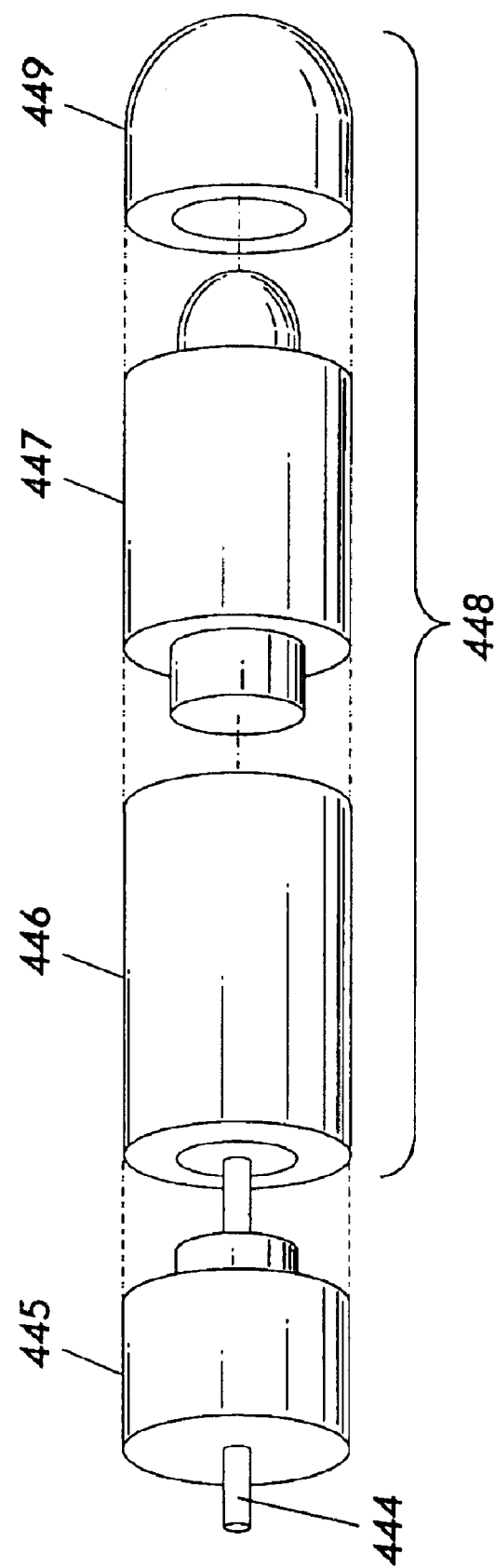
FIG. 50 is an exploded perspective view of a hermetic component housing according to some or all of the concepts of the present invention.

FIG. 50 illustrates another embodiment of the present invention in which a hermetic housing is constructed to provide part of an electrode termination pair 448. The electrode termination pair 448 includes a cup-shaped structure (tip) 449 acting as a tip electrode and the hermetic housing 446 (ring) acting as a ring electrode. The tip 449 and the ring 446 are both substantially cylindrical in shape, and preferably have the same wall thickness. Note that the tip 449 has a rounded nose portion and a base portion that is planar in cross-section. The ring 446 has proximal and distal end portions that are both preferably planar in cross section.

Figure 51:
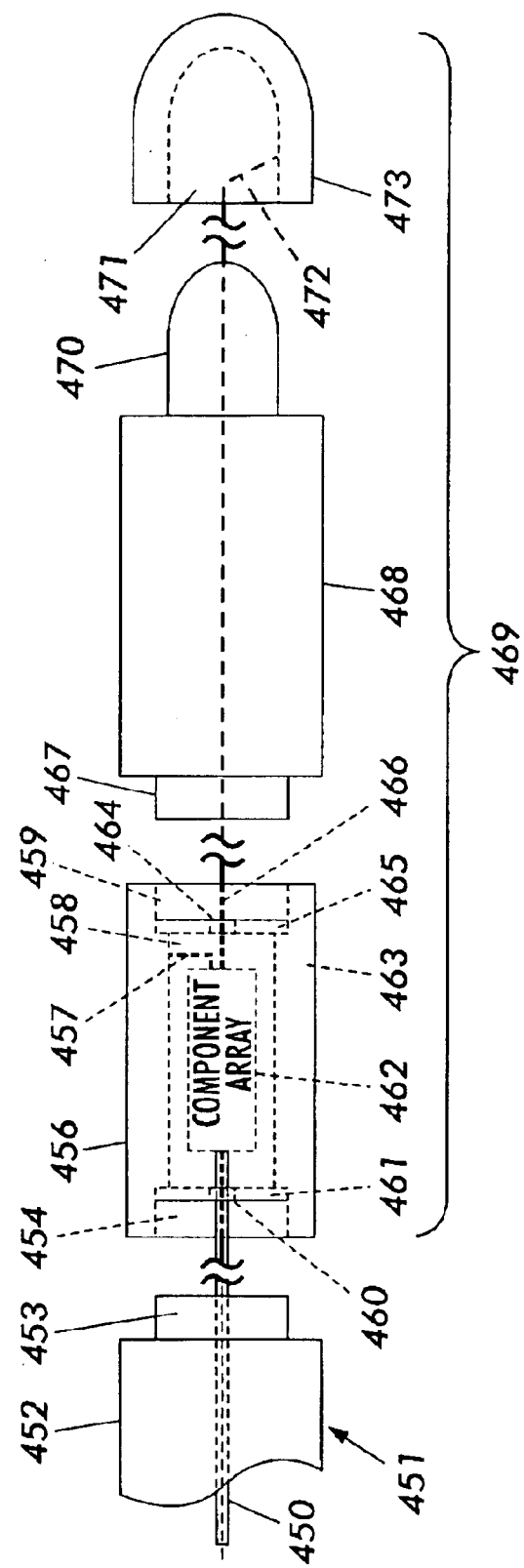
FIGS. 51 through 53 are sectional axial centerline views showing alternative ways in which the component housing of FIG. 50 can be configured.
Figure 52:
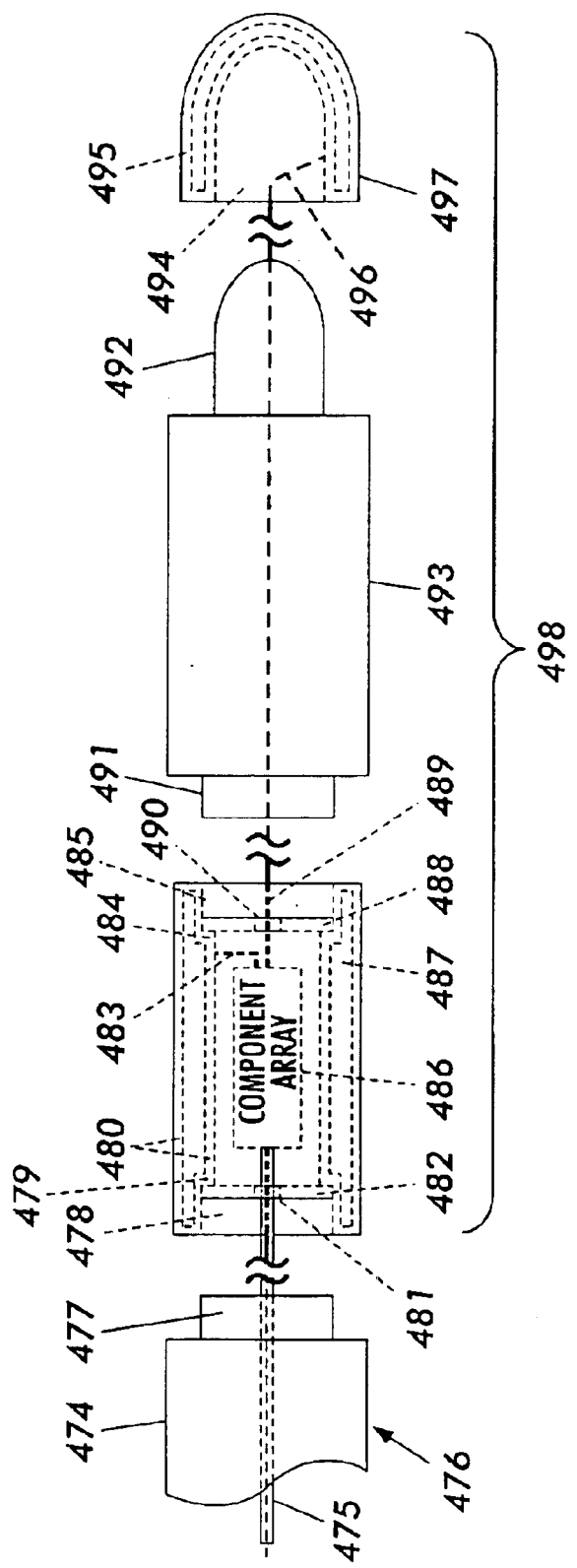
Figure 53:
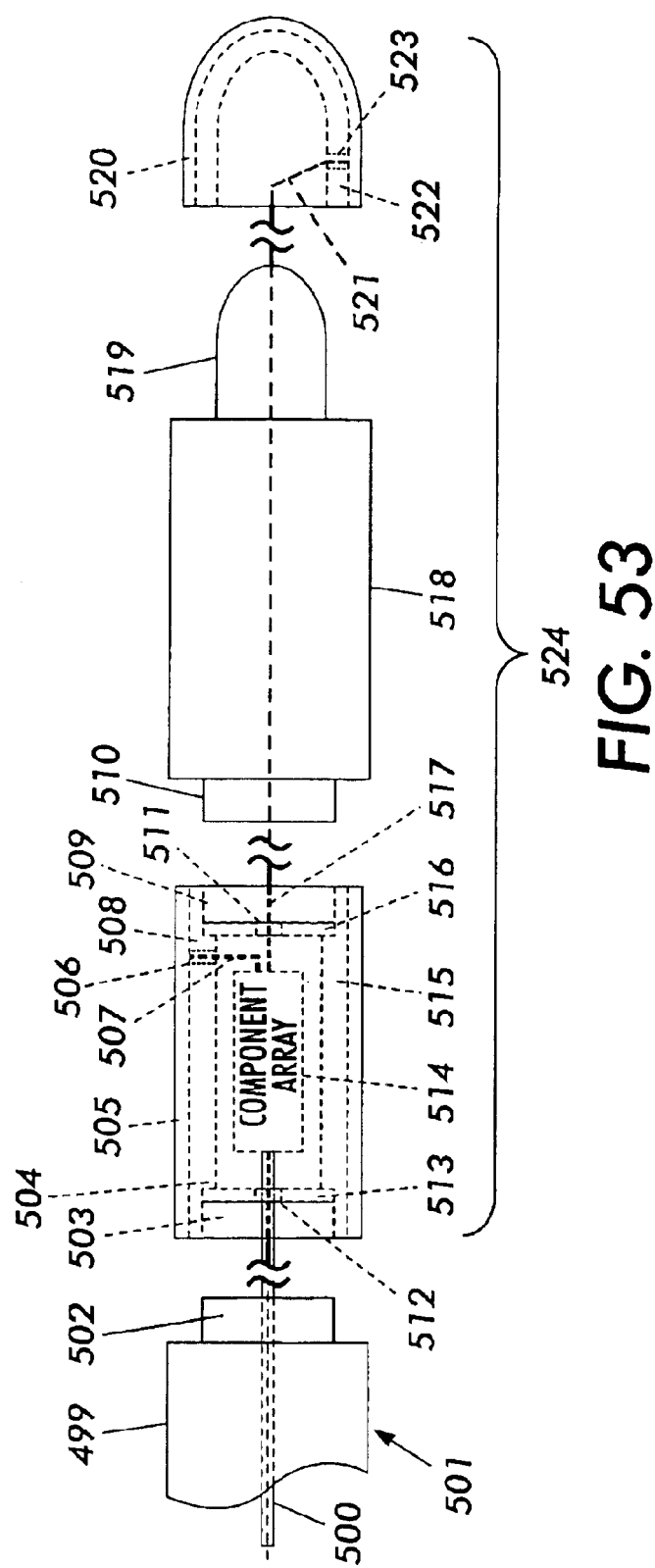

As shown in FIG. 51, the tip 473 and the ring 463 can be made from a body-compatible, non-ferromagnetic metal such platinum, titanium or alloy of platinum or titanium. As shown FIGS. 52 and 53, the tip (497, 522) and the ring (487, 515) can be made of a non-metallic material, such as ceramic, and covered with electrically conductive coatings (495, 520) and (480, 505), respectively. The difference between FIGS. 52 and 53 is that all exposed surfaces of the tip 497 and the ring 487 are coated in FIG. 52, whereas only the outer surface of the tip 522 and the ring 515 are coated in FIG. 53.

If a ceramic is used to form the tip and the ring, the material used is preferably a suitable biocompatible ceramic material such a ceramic of the type commonly used for joint prostheses. By way of example only, such material is available from Ceramic Components Inc. of Latrobe, Pa. To form a ceramic tip and ring, ceramic slurry can be formed into the desired shapes and fired to bake the ceramic material.

The electrically conductive coatings (495, 520) and (480, 505) are preferably formed by very thinly coating the tip and the ring, as by electroplating, sputtering or other deposition technique, etc., with a suitable metal. To facilitate. MRI compatibility, the metal preferably has low magnetic susceptibility, such as titanium, platinum, an alloy of titanium or platinum, or the like. Preferably, the coatings (495, 520) and (480, 505) are applied as thin as possible to achieve the twin goals of efficient electrical interaction with implanted tissue while minimizing interaction with MRI induced electromagnetic fields. By way of example, the thickness of the coatings (495, 520) and (480, 505) may range from mono-molecular thickness to sub-micron or micron level thickness.

FIGS. 50 through 53 show the electrode termination pair (448, 469, 498, 524) being mounted to the distal end of a photonic catheter (451, 476, 501). The tip and the ring are also interconnected by a short insulative stub (447, 468, 493, 518) that is solid, generally cylindrical in shape, and made from silicone, polyurethane, polyethylene, or any other suitable biocompatible electrically insulating material. The outside diameter of the stub preferably equals the outside diameter of the tip and the ring, to facilitate efficient implantation and removal in a patient. The ends of the stub can be bonded to the tip and the ring using a suitable medical adhesive. To provide additional connection integrity, the stub can be formed with end portions (470, 492, 519) of reduced diameter. One end portion of the stub is received into an opening (471, 494) in the base portion of the tip and bonded therein. The other end portion of the stub is received into an opening (459, 485, 509) in the distal end of the ring and bonded therein.

The completed tip/ring assembly can be mounted to the distal end of the photonic catheter in similar fashion. In particular, the photonic catheter will be a generally cylindrical element whose exterior sheath (451, 474, 459) is made from silicone, polyurethane, polyethylene, or any other suitable biocompatible electrically insulating material. Note that the sheath could be tubular in shape, with a small center bore carrying one or more optical conductors therein. Alternatively, the sheath could be formed around the optical conductors such that the conductors are embedded, in the material of the sheath In either case, the outside diameter of the sheath will preferably be the same as that of the ring and can be bonded thereto using a suitable medical adhesive. To provide additional connection integrity, the sheath may be formed with a small end portion (453, 477, 502) of reduced diameter that is snugly received within an opening (454, 478, 503) in the proximal end the ring and bonded therein.

Since the ring functions as a hermetically sealed component housing, it must be provided with hermetically sealed closures at or near the ends thereof These closures may be provided by a pair of closure walls (465, 488, 516) and (461, 482, 513) that are secured within the interior of the ring. The closure walls can be formed from any suitable biocompatible material capable of sealing the ring interior, including metals, polymers, and potentially other materials. To facilitate the secure hermetic attachment of the closure walls, the inside of the ring can be formed with a pair of recessed annular shoulders (456, 479, 504).

There may be disposed within the ring any number of components for delivering electrical signals to, or sensing biological activity in, a body. Such components are collectively shown as a component array by reference numeral (462, 486, 514), and may include opto-electrical transducers, electro-optical transducers, signal processors and amplifiers, digital microprocessors, temperature sensors, R-wave sensors, partial oxygen sensors, and any number of other components. To provide electrical interaction with surrounding body tissue, a positive terminal of the component array is connected to a short metallic lead (457, 483, 507) made from copper or other suitable material of low magnetic susceptance.

In FIG. 51, the lead 457 is electrically connected to the ring by attaching it, as by soldering or the like, directly to the ring itself. In FIG. 52, the metallic lead 483 is electrically connected to the ring by attaching it, as by soldering or the like, to an interior portion of the metallic coating 480. In FIG. 53, the metallic lead 507 is fed through a small hole 506 in the wall of the ring so that it may be attached to the exterior metallic coating 505, as by soldering or the like.

A negative terminal of the component array connects to a longer metallic lead (466, 489, 517) that is also made from copper or other suitable material of low magnetic susceptance. This metallic lead feeds through a hermetic seal terminal (464, 490, 511) mounted on the closure wall. This metallic lead then extends through the material of the stub (which can be molded around the lead) and into the tip.

In FIG. 51, the metallic lead is electrically attached, as by soldering or the like, directly to the tip itself. In FIG. 52, the metallic lead is electrically attached, as by soldering or the like, to an interior portion of the metallic coating. In FIG. 53, the metallic lead is fed through a small hole 523 in the ceramic wall of the tip so that it may be attached to the metallic coating, as by soldering or the like.

When the tip and the ring are implanted in a patient's heart, the tip will typically be embedded in the endocardial tissue, while the ring is situated in the right ventricle, in electrical contact with the endocardium via the ventricular blood. If the photonic catheter is connected to a pacemaker, an optical pulse emanating from a photonic pacemaker pulsing unit (not shown) is sent down a fiber optic element or bundle of the photonic catheter. The fiber optic element or bundle passes into the hermetically sealed interior of the ring via a hermetic seal terminal (460, 481, 512). There, the fiber optic element or bundle delivers the optical pulse to the component array, which preferably includes a photodiode array. The photodiode array produces an electrical impulse that negatively drive the tip with respect to the ring at a potential of about 3–4 volts and a current level of about 3 milliamps for a total power output of about 10 milliwatts. Note that a sensing function could be added by incorporating an electro-optical transducer into the component array. Electrical sense signals would then be converted to optical signals and placed on the fiber optic element or bundle for delivery to a sensing unit (not shown).

Figure 54:
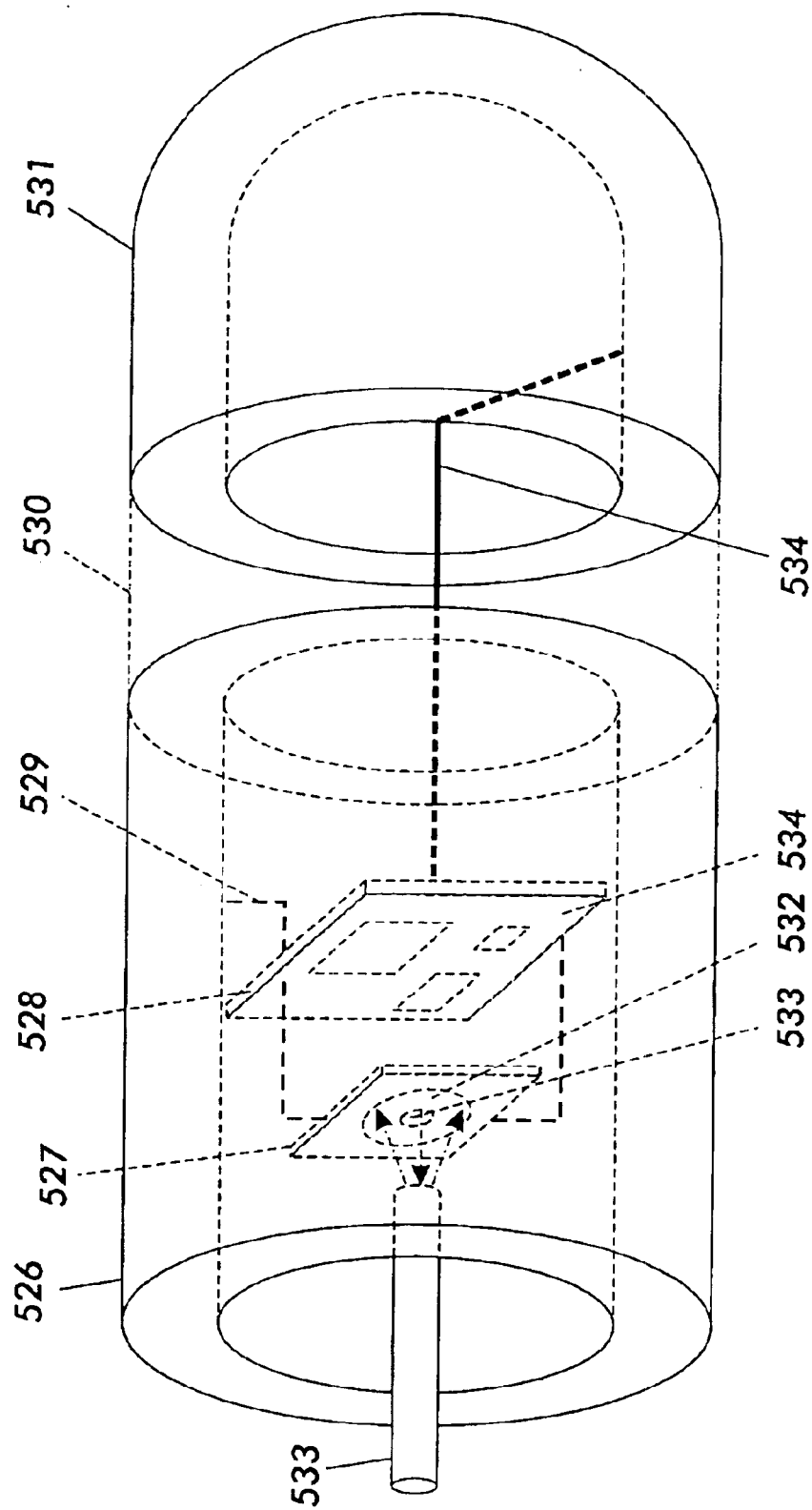
FIG. 54 is a perspective view of the component housing of FIG. 50 showing details of exemplary components that may be housed therein.

FIG. 54 illustrates an exemplary construction of the component array in which the array comprises a photodiode array 532 for receiving optical pacing signals from the fiber optic element or bundle 525 and a light emitting diode 533 for delivering optical sensing signals to the fiber optic element or bundle. The components 532 and 533 are mounted on a circuit substrate 527 that is electrically connected to an electrical circuit unit 534 that may include transducers, amplifiers, oscillators, a microprocessor, and other devices that can assist electrical pulse delivery and biological sensing functions.

Figure 55:
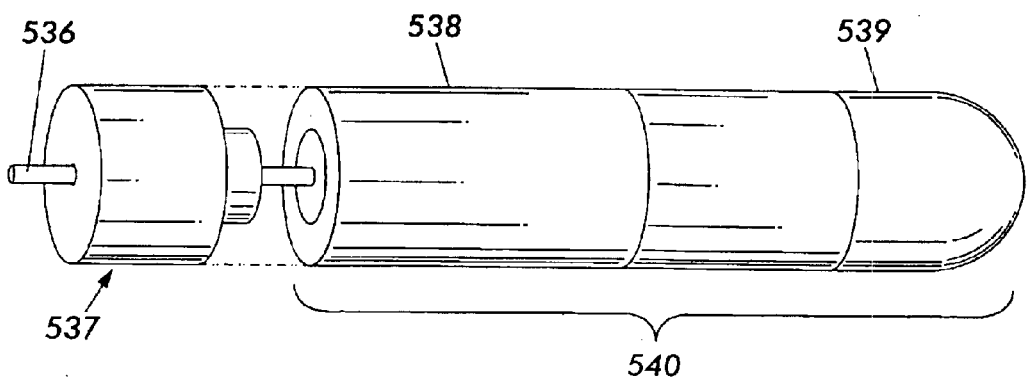
FIG. 55 is a partial exploded perspective view of a hermetic component housing according to some or all of the concepts of the present invention.
Figure 56:
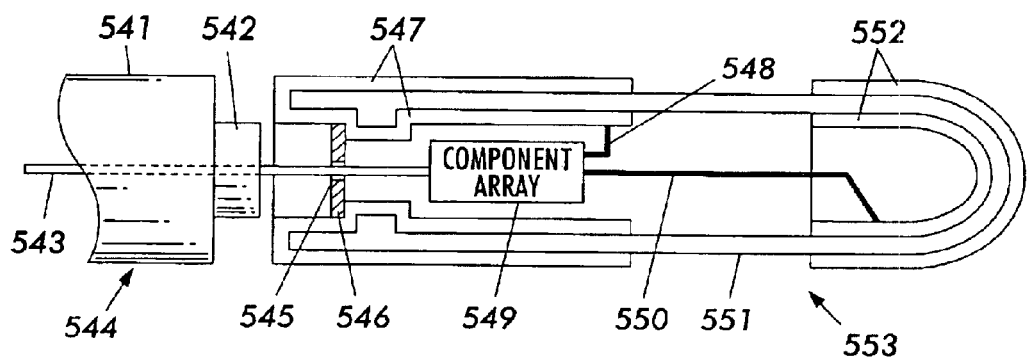
FIGS. 56 and 57 are sectional axial centerline views showing alternative ways in which the component housing of FIG. 55 can be configured.
Figure 57:
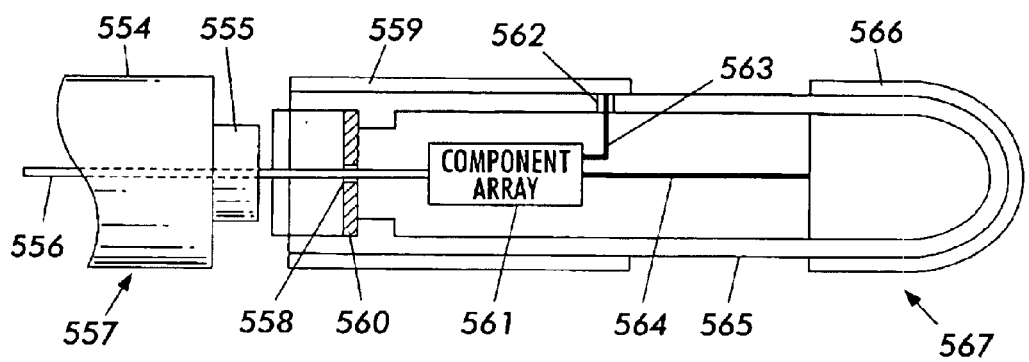

FIGS. 55 through 57 include a modified hermetic housing to provide a unitary or integral electrode termination pair 540. The electrode termination pair 540 includes a tip 539 and a ring 538 that are constructed as metallic coatings formed on the hermetic housing (551, 565).

An electrically conductive coating (552, 566) formed at the distal end of the housing provides the tip. An electrically conductive coating (547, 559) formed at the proximal end of the housing provides the ring.

FIGS. 56 and 57 also show that the component array can be hermetically sealed within the housing via the hermetic seal. The proximal end of the housing may then be secured to the distal end of the photonic catheter, and the fiber optic element or array can be connected to the component array via the hermetic terminal. The component array is electrically connected to the tip and the ring via electrical leads.

Figure 58:
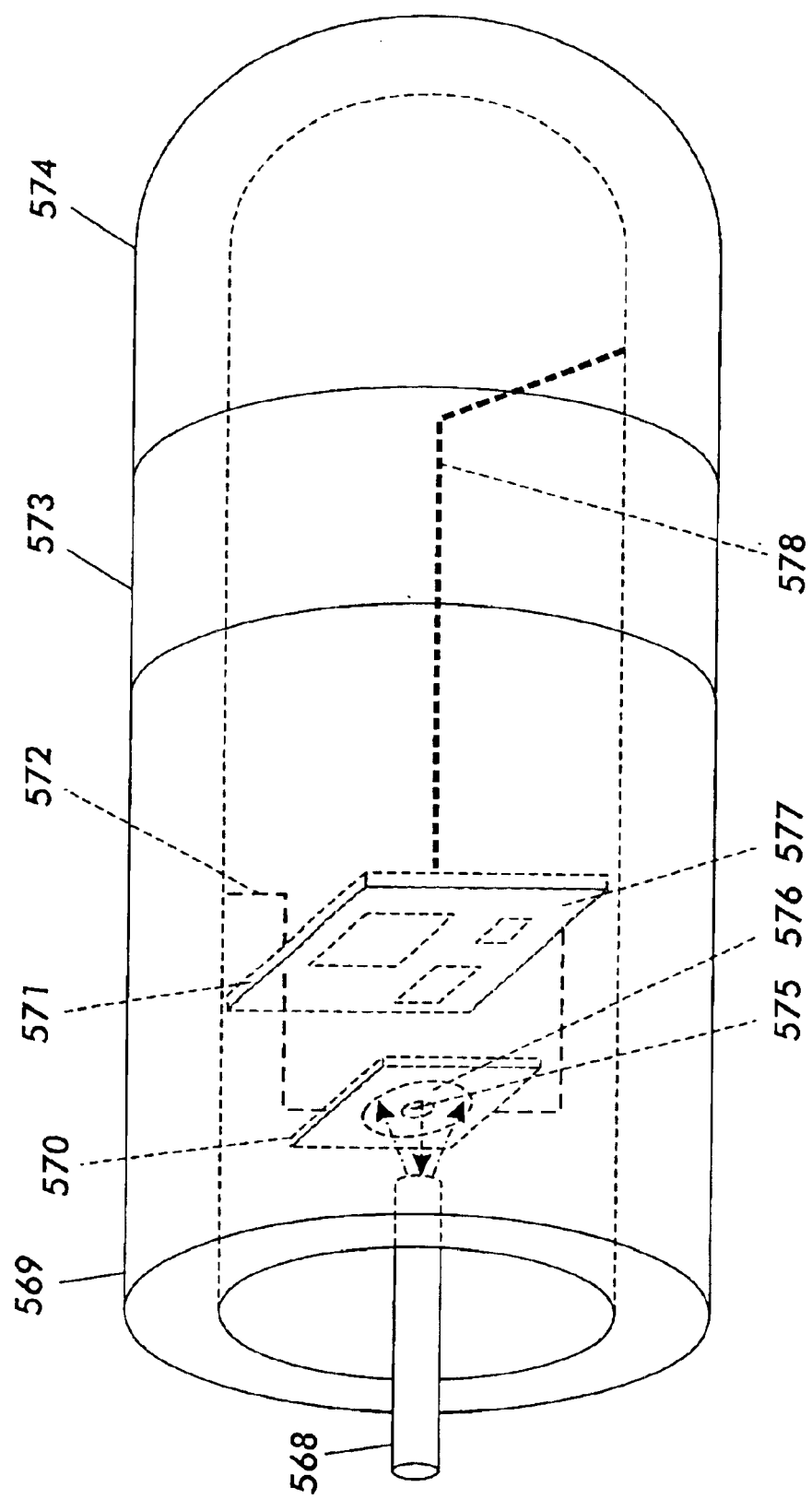
FIG. 58 is a perspective view of the component housing of FIG. showing details of exemplary components that may be housed therein.

FIG. 58 shows an exemplary implementation of the component array within the housing. This component array configuration is identical to the component array configuration of FIG. 55.

Figure 59:
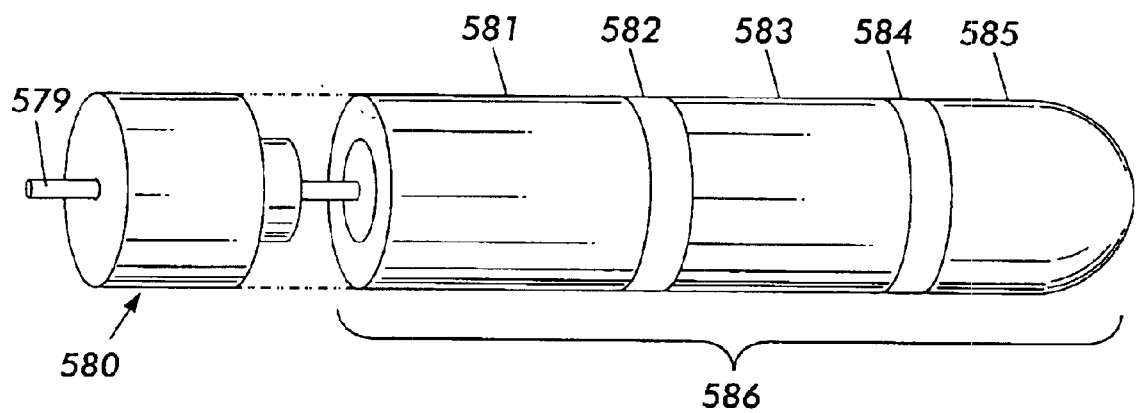
FIG. 59 is a partially exploded perspective view of a hermetic component housing according to some or all of the concepts of the present invention.
Figure 60:
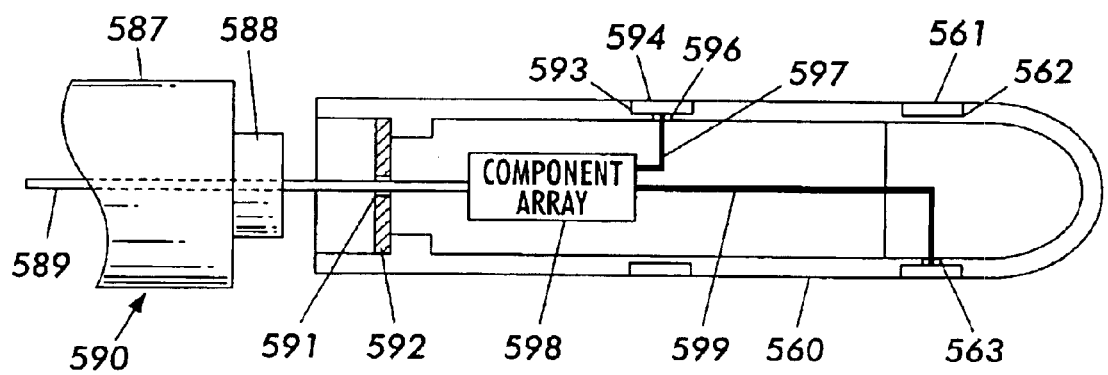
FIG. 60 is a sectional view taken along the axial centerline of the component housing of FIG. 59.

In FIG. 59, a modified hermetic housing again provides a complete electrode termination pair 586. The electrode termination pair 586 includes a tip electrode 584 and a ring electrode 582 that are constructed as electrically conductive band coatings on the hermetic housing, which is designated by reference numeral 581. A shallow well 562 of FIG. 60 formed near the distal end of the housing 560 of FIG. 60 may be used to mount the tip 561. A shallow well 593 of FIG. 60 formed toward the proximal end of the housing 560 of FIG. 60 may be used to mount the ring 594 of FIG. 60.

Figure 61:
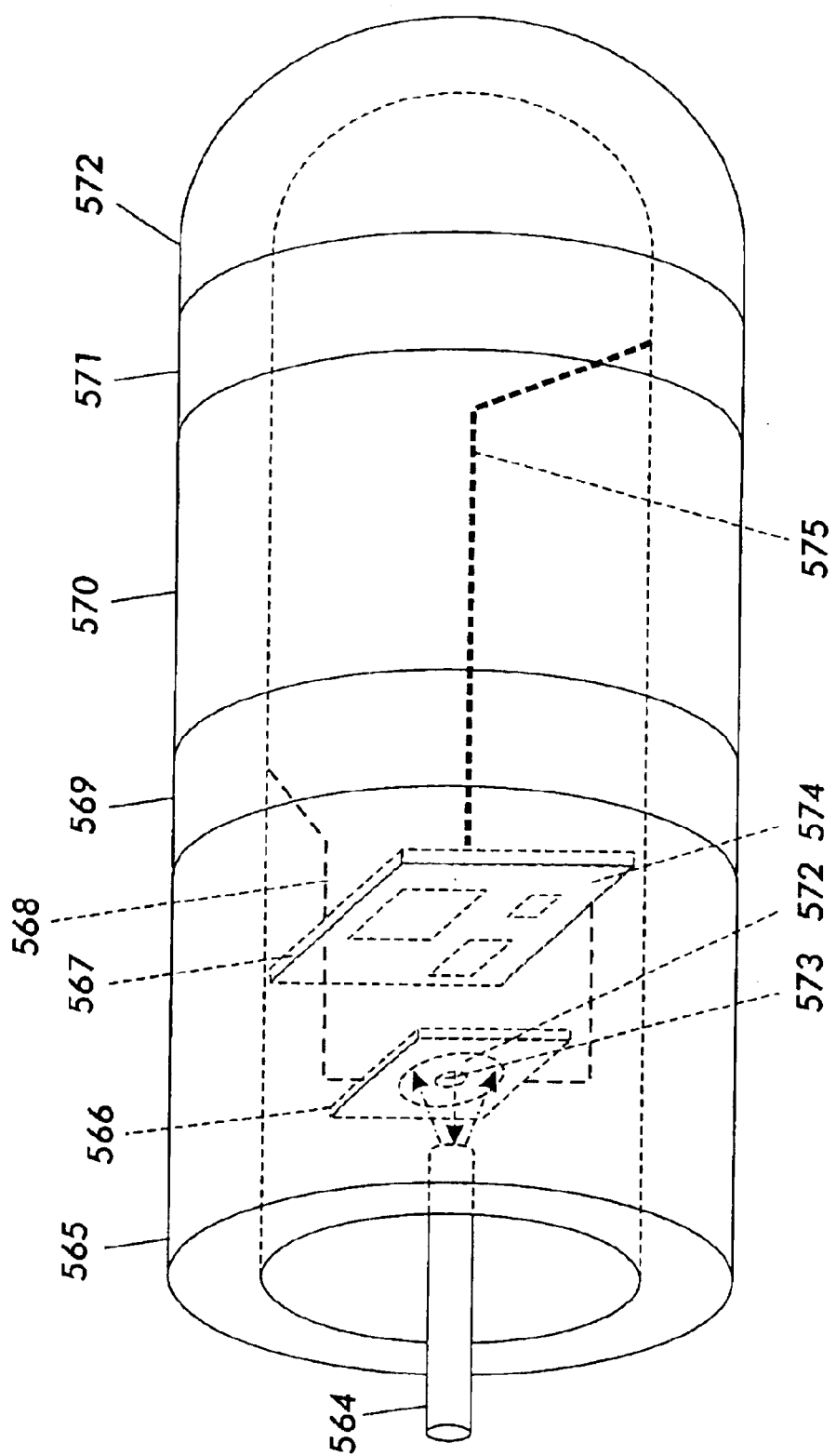
FIG. 61 is a perspective view of the component housing of FIG. 59 showing details of exemplary components that may be housed therein.

FIG. 61 shows an exemplary implementation of the component array within the housing. This component array configuration is identical to the component array configuration of FIG. 54.

Figure 31:
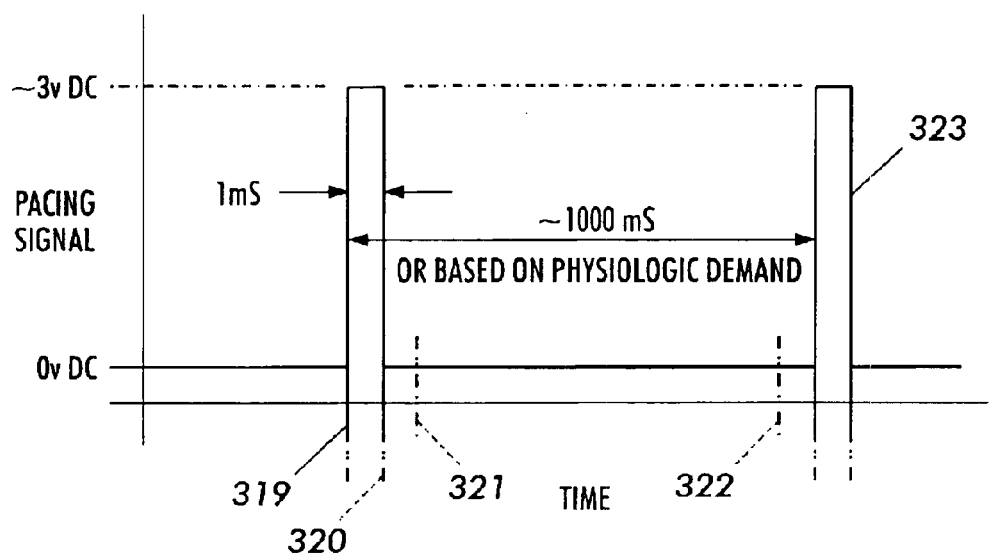
FIG. 31 is a graph depicting a typical pulse sequence used in pacing a human heart, over an interval equivalent to a nominal 1 Hz human heartbeat.

The output of a typical pacemaker is illustrated in FIG. 31, which is a graph of the electrical direct current voltage (vDC) applied to the electrode or electrodes at the distal end of a cardiac pacemaker lead, as a function of time. The indicated voltage of 3 vDC is a nominal value and is typically often selected by the physician based on the type of cardiac anomaly being corrected, the physical state of the patient's heart, and other factors. However, it should be understood that this value is intended to have a safety factor of two built into it; thus the typical voltage required to pace the heart is 1.5 volts direct current, or less.

Referring again to FIG. 31, and noting that the time axis is not to scale, the typical time between pacing events is nominally one second, or 1000 milliseconds (mS). In normal practice, using modem pacemakers, this time interval is not fixed but is variable based upon two factors. The first factor is whether or not the heart requires pacing in order to beat. The term 'demand pacemaker' applies to a device that senses heart activity electrically and does not send a pacing signal to the electrodes if the heart is beating on its own in a manner determined to be acceptable by the computer controller within the device, and based upon input programmed by the physician. Thus, during the time after the refractory period associated with the previous heartbeat ends 321, and up to a time when the next heartbeat is required 322, the pacemaker electrode is used to sense heart activity and to disable the next pacing signal 323 if the heartbeat is regular.

The second factor associated with demand pacing is physiologic demand; modem pacemakers are designed with additional sensing and analytical capability that permits the device to monitor physiologic demand associated with physical activity or other forms of stress that would result in an elevated heartbeat in a normal human subject. In response to this heightened physiologic demand, the pacing signal 323 would be generated at an earlier time than the 1000 mS delay indicated in FIG. 31.

Figure 32:
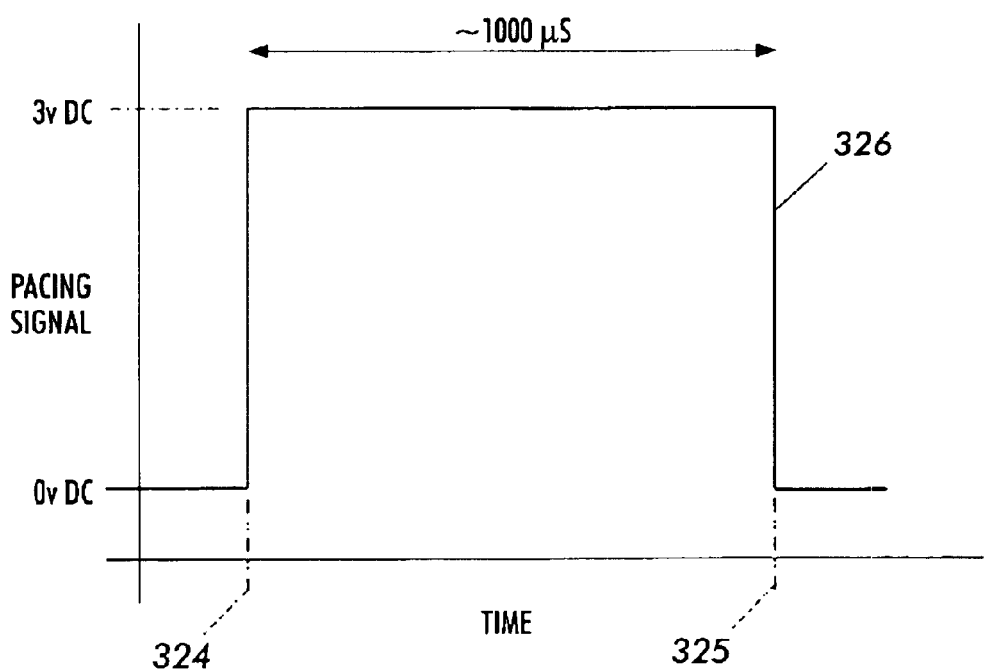
FIG. 32 is a similar graph depicting the pacing pulse as shown in FIG. 31, but with a much finer time scale.

FIG. 32 is an expanded view similar to FIG. 31, showing the pacing signal 326 over the nominal one-millisecond time interval of the actual pacing signal. The beginning of the pacing signal (319, 324) and the end of the pacing signal (320, 325) are shown in both FIG. 31 and FIG. 32 for reference. Note that there is no other activity in this one millisecond time interval; more particularly there is no attempt to sense heart activity nor the heart's response to the pacing signal during the time pacing time interval between times (319, 324) and (320, 325). This is in part due to the fact that while a relatively modest voltage (about 3 volts) is being applied to the heart cardiac tissue by the electrodes, the voltages sensed by the pacemaker in monitoring heart activity (typically in the millivolt range) would be immeasurable using traditional techniques. In addition, the tissues surrounding the pacing electrode develop a polarization potential in response to the energy in the pacing signal; this serves to make measurements of heart activity via those same electrodes very difficult using traditional techniques. However, the interval between times (319, 324) and (320, 325) is very long in the context of modem computational electronic devices.

Figure 33:
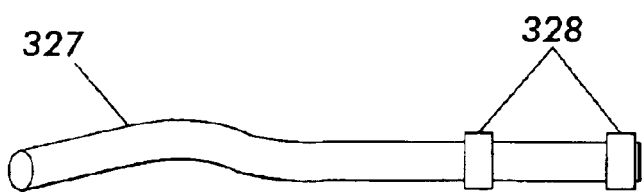
FIG. 33 is a schematic representation of a cardiac pacing lead with two electrodes.
Figure 34:
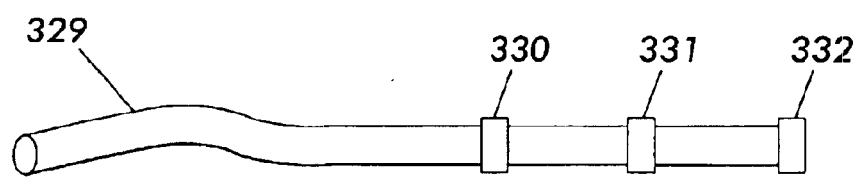
FIG. 34 is a schematic representation of a similar cardiac pacing lead with three electrodes.
Figure 35:
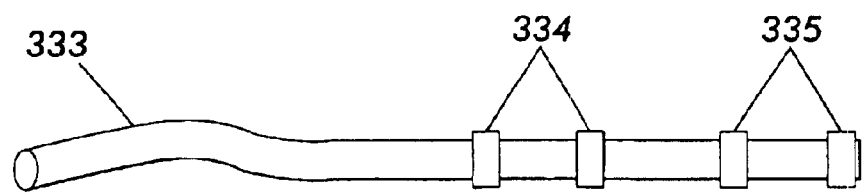
FIG. 35 is a schematic representation of yet another cardiac pacing lead with two pairs of electrodes.

FIGS. 33, 34, and 35 are schematic representations of a cardiac pacemaker lead (327, 329, 333) having various electrode configurations.

In one preferred embodiment, and referring to FIG. 33, pacemaker lead 327 comprises one or more electrical conductors communicating from a connector on the body of the pacemaker device (not shown) to the electrodes 328 that are affixed by one of a number of techniques to the sensitive cardiac tissue that initiates the natural heartbeat and that is paced when necessary by the implanted pacemaker system. The configuration shown in FIG. 33 is for a bipolar pacemaker; the positive and negative terminals for electron flow through the cardiac tissue are the two electrodes 328. It should be noted that there is an alternative configuration referred to as unipolar, and it is not shown in this figure. In the case of a unipolar configuration, there is a single electrode 328 at the heart; the return path for electron flow is through the general bulk tissue back to the case of the device itself. In either unipolar or bipolar configurations, electrodes 328 are used both to pace the heart during the period between times (319, 324) and (320, 325) shown in FIGS. 31 and 32, but are also used to sense heart activity electrically between times 321 and 322 shown in FIG. 31.

In the embodiment depicted in FIG. 34, sensing electrode 332 is disposed at a distance of at least about 5 millimeters from pacing electrode 330 in order to provide a degree of electrical isolation between tissues that will develop a polarization potential and tissues being sensed for heartbeat activity. Similarly, in the embodiment depicted in FIG. 35, sensing electrode pair 335 is disposed at a distance of at least about 5 millimeters from pacing electrode pair 334.

In another preferred embodiment, cardiac pacemaker lead is not an electrical conductor but rather comprises one or more optical fibers that carry light energy between the pacemaker device case and the electrodes. This embodiment may be used in order to create pacemaker leads that are immune to the intense radio frequency and magnetic fields associated with magnetic resonance imaging (MRI) and which fields can in some cases result in damage to the pacemaker and/or injury or death to the pacemaker patient who inadvertently undergoes MRI diagnosis. In this embodiment electrodes are more complex than in the former embodiment; for purposes of pacing they comprise a photodiode (not shown) used to convert light energy to electrical energy within them, and in the case of sensing cardiac activity they also comprise a miniature electrical amplifier and light emitting diode source that creates an optical signal that travels from the electrode back to a pacemaker device that uses the photonic catheter of this embodiment.

In another embodiment, and referring to FIG. 34, the pacemaker lead 329 connects the pacemaker device case (not shown) to a set of electrodes 330, 331, and 332 at its distal end and affixed to cardiac tissue as in the previous embodiment. Electrode 331, as in the previous embodiment, is capable of either pacing the heart or sensing heart activity electrically. Electrode 330 is used only to pace the heart, and is identical in its function to that part of the function of the dual-purpose electrode. In like manner electrode 332 is used only for sensing heart activity electrically, in a fashion identical to that part of the function of the dual-purpose electrode.

The reason for the configuration shown in FIG. 34 is that the cardiac tissue immediately involved in the pacing event, and which develops a polarization potential as a result of the pacing signal, is somewhat removed physically from the cardiac tissue immediately around the sensing electrode 332, thus providing some degree of isolation from polarization potential in the area where cardiac sensing is being done, but still providing ample opportunity for sensing any cardiac activity. Thus this embodiment provides the opportunity for sensing measurements to be made during dwell periods in the overall pacing signal wherein no voltage is being applied to the cardiac tissue.

In a further embodiment, and still referring to FIG. 34, pacemaker lead 329 does not contain electrical conductors but rather comprises one or more optical fibers, as described in a previous embodiment. Likewise, electrodes 330 and 331 have the capability to convert optical energy to electrical energy in order to pace the heart, and electrodes 331 and 332 comprise electrical amplifier and electricity-to-light conversion, as is also described in the previous embodiment.

In yet another preferred embodiment, shown in FIG. 35, pacemaker lead 333 connects the pacemaker device case (not shown) to a set of electrodes 334 and 335 at its distal end and is affixed to cardiac tissue as in the previous embodiments. In this embodiment, additional separation between the volume of cardiac tissue being paced (between electrodes 334) and the volume of cardiac tissue being sensed (between electrodes 335) is created in order to provide further improvements in electrical isolation between those areas, thereby providing further improvement in the ability to make sensing measurements during cardiac pacing.

In yet another embodiment, and still referring to FIG. 35, pacemaker lead 333 does not contain electrical conductors but rather one or more optical fibers, as described in a previous embodiment. Likewise, electrodes 334 have the capability to convert optical energy to electrical energy in order to pace the heart, and electrodes 335 comprise electrical amplifier and electricity-to-light conversion as also described in previous embodiments.

Figure 36:
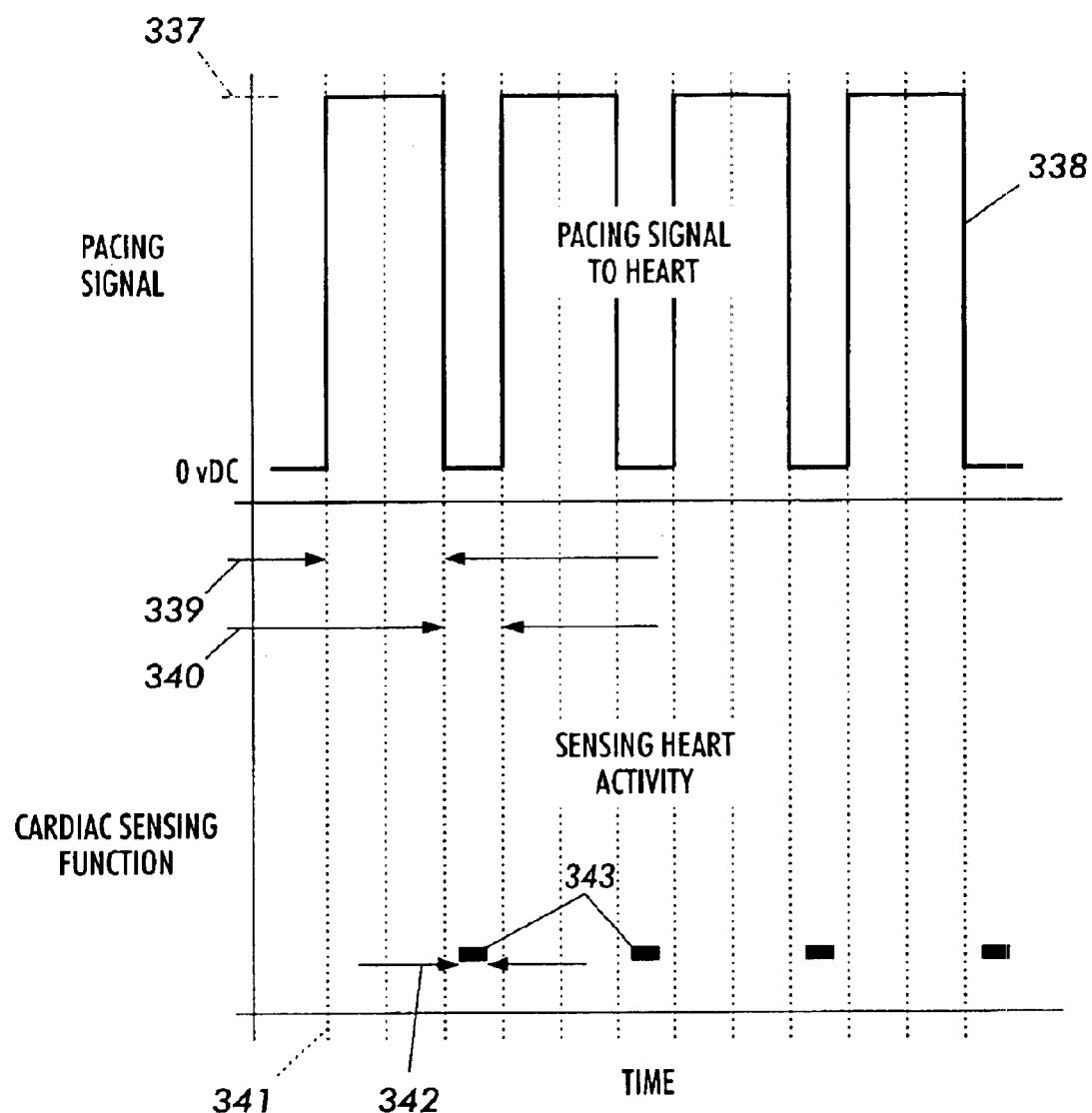
FIG. 36 is a graph depicting the use of pulse width pacing signals and interleaved periods for sensing heart activity.

In one preferred embodiment of the present invention, a technique of pulsewidth modulation is used to pace the heart and to provide the opportunity for real-time measurement of cardiac tissue activity. Referring to FIG. 36, it may be seen that a pacing signal 338 that begins at time 341 is not a traditional square wave pulse as shown in FIGS. 31 and 32, but is a series of much faster pulses that apply a voltage 337 for a time period 339 and that apply no voltage during time period 340.

For example, if time period 339 is chosen to be two microseconds and if time period 340 is chosen to be one microsecond, a single repeat of sequence 339 and 340 has a duration of three microseconds. If this sequence is repeated three hundred thirty-three times, the time interval for pulse 338 will be about one millisecond, corresponding to the time interval of a single traditional pacing signal to the heart. For purposes of this illustrative example and again referring to FIG. 36, voltage 337 may be chosen to compensate for the fact that no voltage is applied for one third of the time. In order for a pulsewidth signal 338 having 66% duty cycle as described in this illustration to deliver the same amount of electrical energy to the cardiac tissue as in a square wave 3 volt DC pulse of 1 millisecond duration, and taking into consideration the relationship of energy to voltage in a purely resistive medium (energy is proportional to the square of the applied voltage), the voltage 337 will be chosen to be 3 volts DC multiplied by the square root of 1.5, or 3.67 volts direct current. If the frequency of pulsewidth modulated pacing curve 338 is high with respect to the reaction time of cardiac tissue, that tissue will react in the same manner to the pulsewidth modulated signal having 66% duty cycle and 3.67 volt peak signal level as it would to a square wave of the same duration at 3.0 volt.

The foregoing example is intended to be illustrative only; in the embodiment depicted, time periods 339 and 340 may range from below 1 microseconds to over 100 microseconds in order to optimize the response of the system to design choices in the pacemaker device or the pacemaker lead and electrodes. In addition, this embodiment provides for time periods 339 and 340 to be variable over time, both in absolute duration and in their ratio. Further, the applied voltage 337 may be variable over time within a single pacing signal 338, or between pacing signals, as a function of changes in physiologic demand or based on changes in programmed response of the pacemaker system. For purposes of this specification, the overall signal that spans between times 339 and 340 will be referred to as the pacing signal, the shorter signals sent to the heart in multiples will be referred to as pulses, and the much shorter signals described in this illustrative example as having time duration 339 will be referred to as micropulses.

Referring once again to FIG. 36, it may be seen that a cardiac tissue sensing measurement 343 may be carried out during time period 342. In one embodiment, time period 342 may occur any time during the pacing signal and may have any duration appropriate to making said sensing measurement. In a preferred embodiment, time period 342 is selected to be shorter in duration than time period 340, and is further synchronized so as to fall within time period 340. The result is that the electrical measurement of cardiac tissue activity is done during a time period wherein there is not pacing signal applied to the tissue.

Referring again briefly to FIGS. 33, 34, and 35, it may be seen that in combination with the placement of electrodes on pacemaker lead that provides isolation between the tissue being paced and the tissue being sensed, the additional temporal isolation of sensing period from the active time period of the pulsewidth modulated pacing signal, a means is provided to measure the onset of cardiac response to the pacing signal while the signal is still being generated as a set of multiple shorter pulses.

Figure 37:
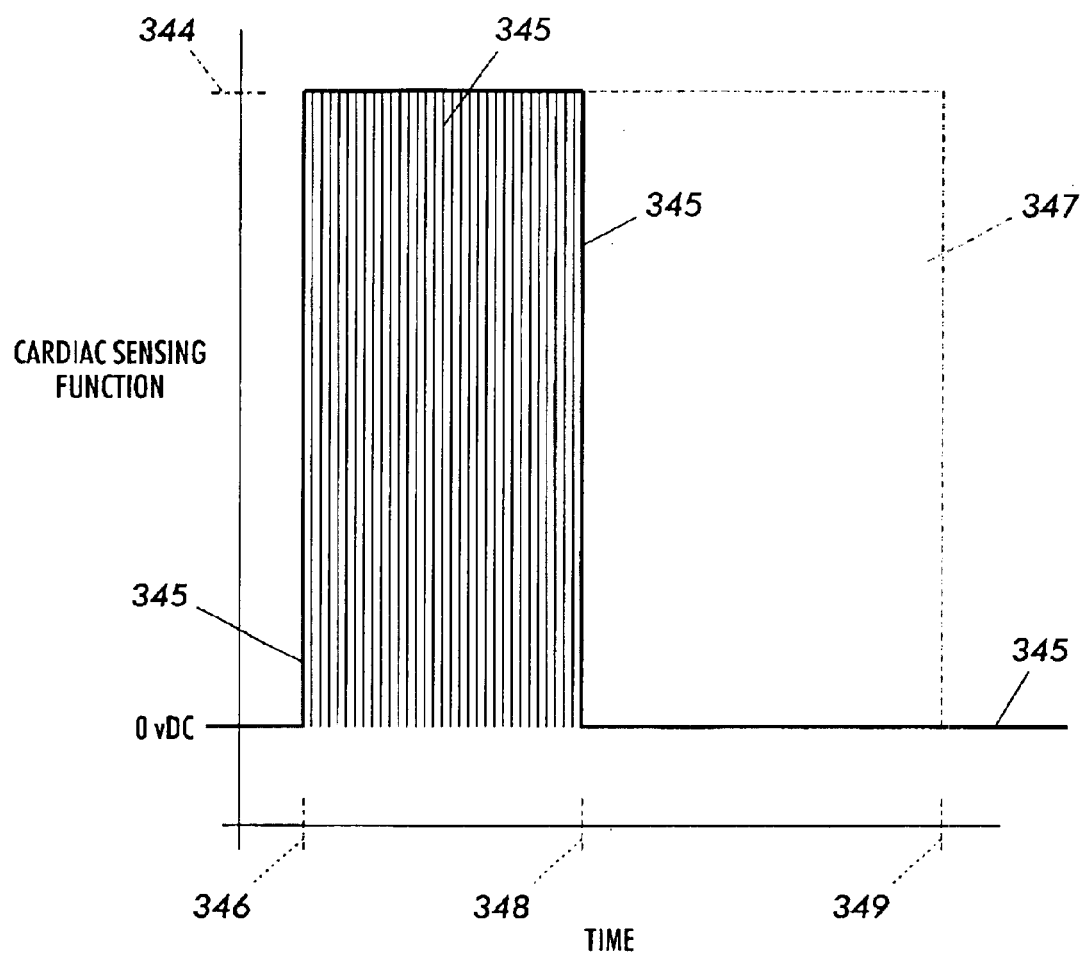
FIG. 37 is a graph depicting the operation of one embodiment according to some or all of the concepts of the present invention that gains energy efficiency by means of early termination of the pacing signal.

FIG. 37 is a graph depicting the operation of one preferred embodiment that gains energy efficiency by means of early termination of the pacing signal, but which uses a constant voltage applied to the micropulses comprising the pacing signal. The peak voltage of pulses that make up pacing signal 345 rises from zero to voltage 344 at time 346, as previously shown in FIG. 36. At time 348, when a signal from heart causes cessation of the micropulsing process, the pulsewidth pacing signal 345 returns to zero until the next pacing signal is commanded from the demand controller. The area 347 depicts the additional signal that a traditional pacemaker not practicing pulsewidth pacing would send to pace the heart after the onset of a beat at time 348. As discussed previously, standard clinical practice calls for a threefold safety factor in pulse duration; employing a pacemaker in a manner depicted in FIG. 37, would result in up to approximately a 65 percent reduction in energy consumption for the pacemaker system.

Figure 38:
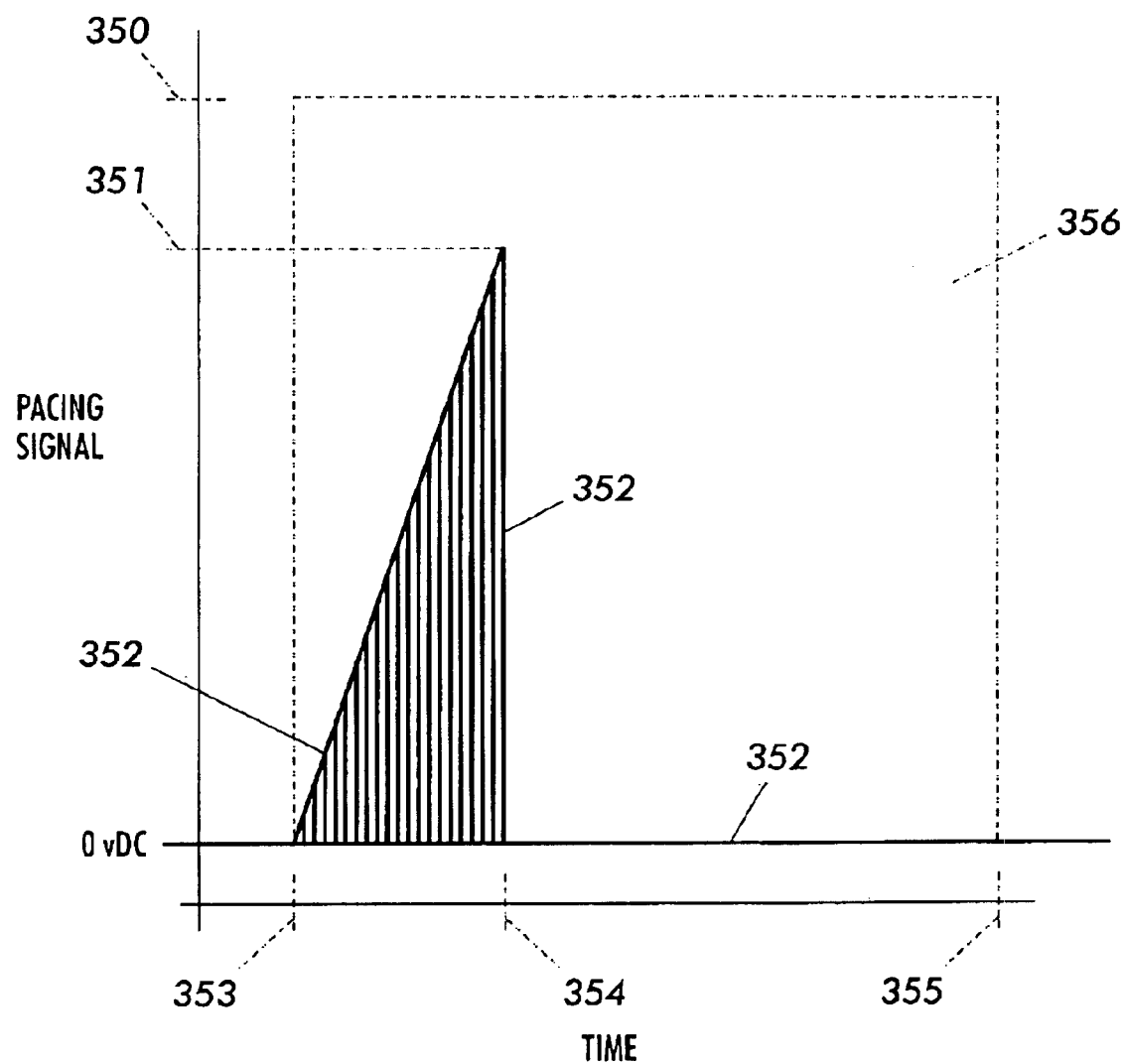
FIG. 38 is a graph depicting the operation of another embodiment according to some or all of the concepts of the present invention that gains energy efficiency by means of both early termination of the pacing signal and by gradient pulse width power control.

FIG. 38 is a graph depicting the operation of another preferred embodiment that gains energy efficiency by means of both early termination of the pacing signal and by the additional use of gradient pulsewidth power control. As in the previous embodiment, pulsewidth pacing signal 352 begins to rise from zero at time 353, and the voltage of each of the micropulses rises with each micropulse cycle. FIG. 38 depicts a linear rise with time, but experimentation may result in a different algorithm that better matches the electrochemistry of cardiac tissue; thus FIG. 38 should be considered as illustrative of a variety of waveforms that may be employed to excite the heart. At time 354, when a signal from heart causes cessation of the micropulsing process, the pulsewidth pacing signal 352 returns to zero until the next pacing signal is commanded from the demand controller. As in the example of FIG. 37, the area 356 depicts the signal that a traditional pacemaker not practicing pulsewidth pacing would send to pace the heart.

As discussed previously, standard clinical practice calls for a threefold safety factor in pulse duration. The typical twofold safety factor in applied voltage results in a power level that is four times higher than the minimum to pace the specific patient's heart. Thus in combination the joint safety factors applied to voltage and pulse duration result in an energy utilization that is twelve times higher than the minimum needed to reliably pace that individual's heart. By practicing pulsewidth pacing, which permits the cessation of the pulsewidth pacing signal virtually the instant the heart begins to beat, the energy consumption of a pacemaker may be reduced by as much as 90%.

It should also be understood that in using a pulsewidth modulation control technique, it is not necessary to alter the actual peak voltage of the pulses that make up the pacing signal to effect an apparent change in applied voltage. If the frequency of the pulses is high enough in comparison to the response time of the circuit and the cardiac tissue through which the pacing signal is conducted, the tissue will react in the same manner as if the applied voltage were the actual peak voltage multiplied by the duty cycle. Thus, the electronic circuit may be designed to utilize a single voltage and adjust duty cycle by adjusting the ratio of times 339 and 340. This permits optimization the energy efficiency of power sources and switching circuits.

Figure 39:
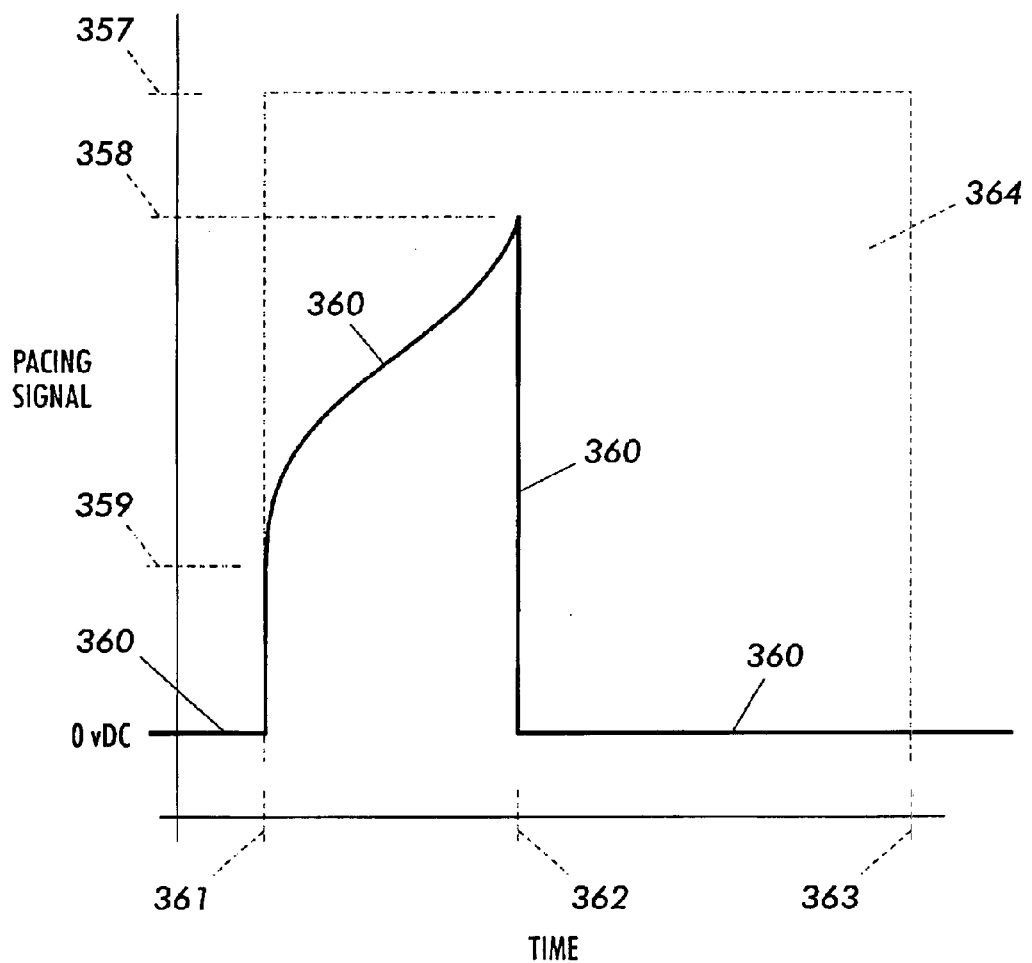
FIG. 39 is another graph of the embodiment in FIG. 38, but with alternate waveform of the pacing signal.

FIG. 39 depicts an alternative overall waveform for pacing signal 360. Note that for reasons of simplicity the overall value of peak voltage is shown for pacing signal 360, and not the individual pulsewidths, as shown in FIG. 38. However, this embodiment still makes use of the high-frequency pulsewidth approach shown in greater detail in FIGS. 37 and 38. Whereas FIG. 38 depicts a linear rise with time, FIG. 39 depicts an initial rise of pacing signal 360 at time 361 from 0 vDC to voltage 359, followed by a nonlinear increase to voltage 358, at which time 362 a heartbeat has been sensed, and pacing signal 360 is cut off as in the previous embodiments described herein.

Experimentation may result in a different algorithm that better matches the electrochemistry of cardiac tissue, and this algorithm may be developed for the specific patient during the initial post-implantation period. Thus, FIGS. 38 and 39 should be considered as illustrative of a variety of waveforms that may be employed to excite the heart, and may be made specific to the needs of each pacemaker patient.

As in the previous embodiment depicted in FIG. 38, the use of pulsewidth modulation techniques in the embodiment depicted in FIG. 39 permits optimization of energy efficiency by adjusting duty cycle rather than adjusting actual peak voltage.

The photonic catheter described above may be used for transmission of a signal to and from a body tissue of a vertebrate. The fiber optic bundle has a surface of non-immunogenic, physiologically compatible material and is capable of being permanently implanted in a body cavity or subcutaneously. The fiber optic bundle has a distal end for implantation at or adjacent to the body tissue and a proximal end. The proximal end is adapted to be coupled to and direct an optical signal source, and the distal end is adapted to be coupled to an optical stimulator. The fiber optic bundle delivers an optical signal intended to cause an optical stimulator coupled to the distal end to deliver an excitatory stimulus to a selected body tissue, such as a nervous system tissue region; e.g., spinal cord or brain. The stimulus causes the selected body tissue to function as desired.

The photonic catheter further includes a photoresponsive device for converting the light transmitted by the fiber optic bundle into electrical energy and for sensing variations in the light energy to produce control signals. A charge-accumulating device receives and stores the electrical energy produced by the photoresponsive device. A discharge control device, responsive to the control signals, directs the stored electrical energy from the charge-accumulating device to a cardiac assist device associated with a heart.

The photoresponsive device may include a charge transfer control circuit and a photodiode. The charge transfer control circuit controls a discharging of a photodiode capacitance in two separate discharge periods during an integration period of the photodiode such that a first discharge period of the photodiode capacitance provides the sensing of variations in the light energy to produce control signals and a second discharge period of the photodiode capacitance provides the converting the light transmitted by the photonic lead system into electrical energy. The first discharge period can be a shorter time duration that the time duration of the second discharge period. During the first discharge period, a control signal sensing circuit is connected to the photodiode, and during the second discharge period, the charge-accumulating device is connected to the photodiode. The charge-accumulating device may be a capacitor or a rechargeable battery.

The photonic catheter can also transmit between the primary device housing and the cardiac assist device, both power and control signals in the form of light. A photoresponsive device converts the light transmitted by the photonic lead system into electrical energy and to sense variations in the light energy to produce control signals. A charge-accumulating device receives and stores the electrical energy produced by the photoresponsive device, and a discharge control device, responsive to the control signals, directs the stored electrical energy from the charge-accumulating device to the cardiac assist device associated with the heart.

The photoresponsive device, in this embodiment, may include a charge transfer control circuit and a photodiode. The charge transfer control circuit controls a discharging of a photodiode capacitance in two separate discharge periods during an integration period of the photodiode such that a first discharge period of the photodiode capacitance provides the sensing of variations in the light energy to produce control signals and a second discharge period of the photodiode capacitance provides the converting the light transmitted by the photonic lead system into electrical energy. The first discharge period can be a shorter time duration that the time duration of the second discharge period. During the first discharge period, a control signal sensing circuit is connected to the photodiode, and during the second discharge period, the charge-accumulating device is connected to the photodiode. The charge-accumulating device may be a capacitor or a rechargeable battery.

The physical realization of the photodiode functions as light-detecting elements. In operation, the photodiode is first reset with a reset voltage that places an electronic charge across the capacitance associated with the diode. Electronic charge, produced by the photodiode when exposed to illumination, causes charge of the photodiode capacitance to dissipate in proportion to the incident illumination intensity. At the end of an exposure period, the change in photodiode capacitance charge is collected as electrical energy and the photodiode is reset.

Manipulating or adjusting the charge integration function of the photodiode can modify the creation of energy by the sensors. Charge integration function manipulation can be realized by changing of an integration time, $T_{int}$, for the photodiode. Changing the integration time, $T_{int}$, changes the start time of the charge integration period.

Integration time, $T_{int}$, is the time that a control signal is not set at a reset level. When the control signal is not at a reset value, the photodiode causes charge to be transferred or collected therefrom. The timing of the control signal causes charge to be transferred or collected from the photodiode for a shorter duration of time or longer duration of time. This adjustment can be used to manage the charge in the photodiode so that the photodiode does not become saturated with charge as well as to manage the current output of the sensor.

Another conventional way of manipulating the charge integration function is to use a stepped or piecewise discrete-time charge integration function. By using a stepped or piecewise discrete charge integration function, the charge in the photodiode can be further managed so that the photodiode does not become saturated with charge as well as to manage the current output of the photodiode.

The photonic catheter can also be used to measure displacement current. Unlike a standard conduction current of moving electrons, displacement current is a measure of the changing electric field in the air, generated by the shifting voltages on the skin surface. To accurately measure this subtle current in the air without shorting it, a sensor is needed with impedance higher than that of the air gap between the body and the sensor. Otherwise, the sensor will drain the electrical signal just like an ECG contact sensor does. The sensor can be a small copper disc about a centimeter across, which can produce sensitive ECGs.

Figure 66:
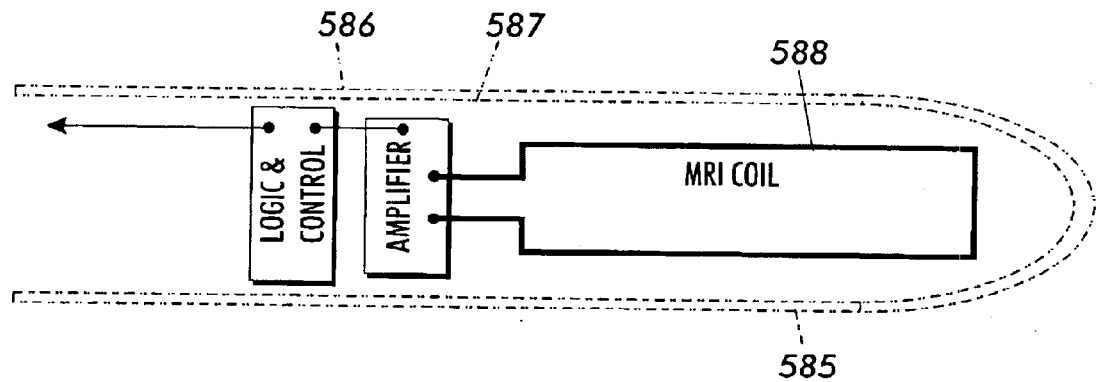
FIGS. 66 through 69 are schematics of various MRI coils for a photonic catheter according to some or all of the concepts of the present invention.
Figure 67:
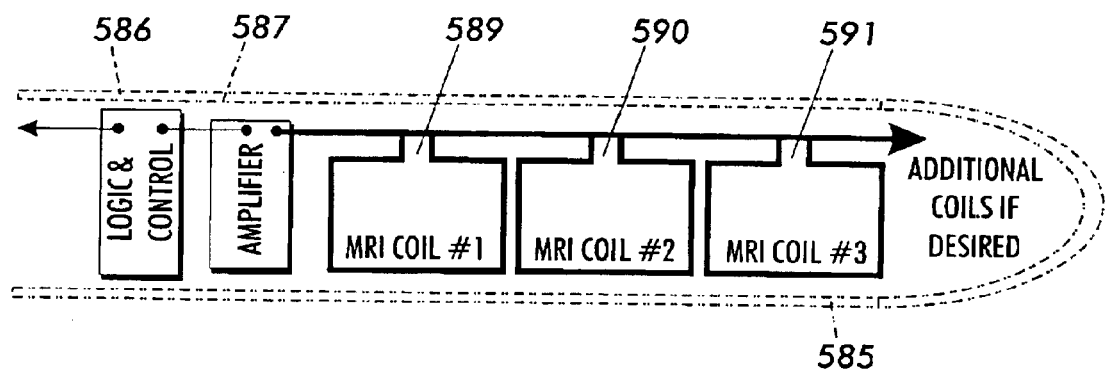
Figure 68:
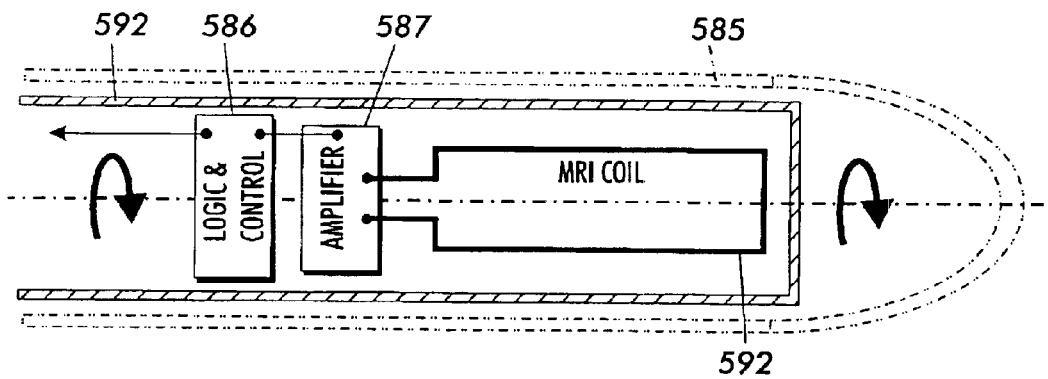
Figure 69:
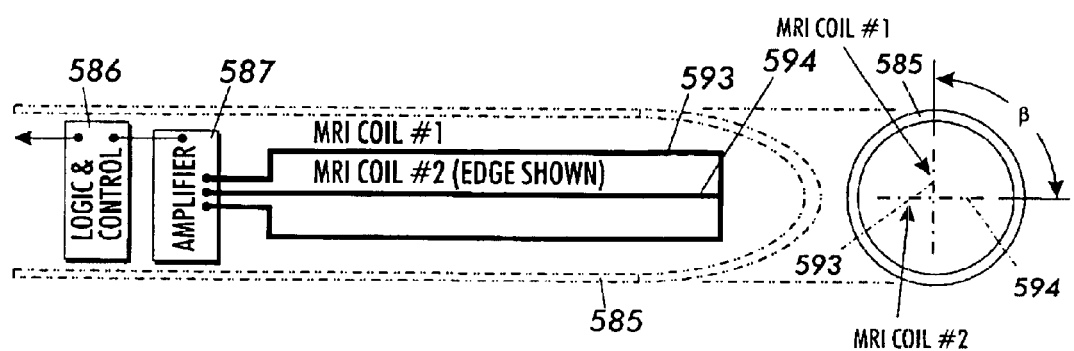

As illustrated in FIGS. 66–69, a photonic catheter 585 may contain a sensor to detect the presence of MRI insult. Most specifically, the photonic catheter 585 may include at a distal end a logic and control circuit 586 connected to an amplifier 587. The amplifier 587 may be connected to a single MRI coil as illustrated in FIG. 66 or to multiple MRI coils (589, 590, 591 . . . ) as illustrated in FIG. 67. In FIG. 68, the MRI insult sensor is encased in a sleeve 592 that enables the MRI coil 592 to be rotatable within the photonic catheter 585. Lastly, the photonic catheter 585, as illustrated in FIG. 69, may position two MRI coils 593 and 594 at predetermined angles β to each other, such as 90°. The MRI coils are located in the distal end of the photonic catheter and detects characteristics of magnetic radiation of a predetermined nature. Each coil may be designed to detect a different type of radiation.

Figure 21:
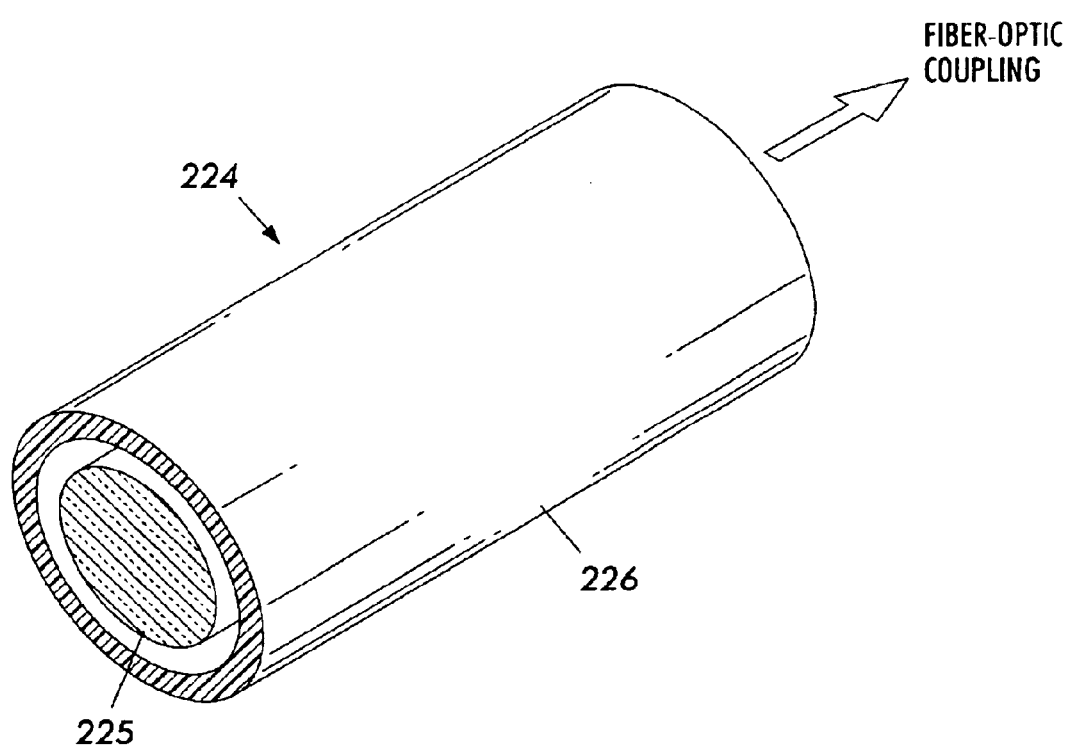
FIG. 21 illustrates a pressure optical transducer according to some or all of the concepts of the present invention.

FIG. 21 illustrates an optical transducer including a pressure sensor 225 in a porous non-conductive insert 226 that is coupled to a photonic catheter or other optical communication channel.

Figure 22:
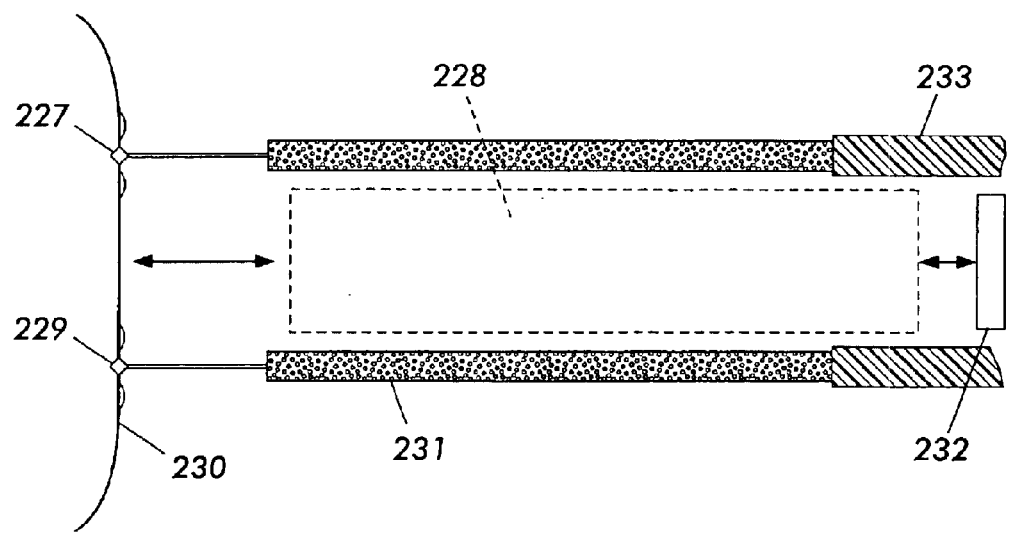
FIGS. 22 through 26 are block diagrams of various pressure optical transducers according to some or all of the concepts of the present invention.

FIG. 22 illustrates in more detail, the pressure optical transducer device of FIG. 21. In FIG. 22, an optical transducer device is anchored to a predetermined tissue region 230, such as a cardiac muscle region, by anchors 227 and 229. The anchors are connected to a porous sleeve 231 that houses a pressure sensor 228. The optical transducer device further includes a mechanical-optical transducer 232, within housing 233, to produce an optical signal corresponding to the movement of pressure sensor 228. Pressure sensor 228 moves back and forth in response to pressure generate by contractions of the predetermined tissue region 230. Based on the pressure gradient produced, the pressure sensor 228 will move and cause the mechanical-optical transducer 232 to produce a signal containing information on the characteristics of the predetermined tissue region 230.

Figure 23:
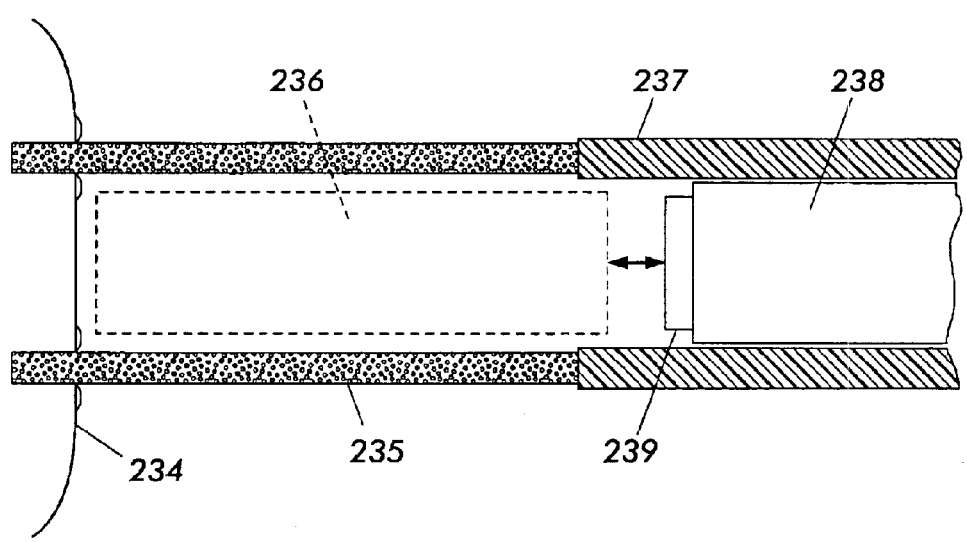

In FIG. 23, an optical transducer device is anchored to a predetermined tissue region 234, such as a cardiac muscle region, by a porous sleeve 235 that houses a pressure sensor 236. The optical transducer device further includes a mechanical-optical transducer 239, within housing 237 and connected to optical cable 238, to produce an optical signal corresponding to the movement of pressure sensor 236. Pressure sensor 236 moves back and forth in response to pressure generate by contractions of the predetermined tissue region 234. Based on the pressure gradient produced, the pressure sensor 236 will move and cause the mechanical-optical transducer 239 to produce a signal containing information on the characteristics of the predetermined tissue region 234.

Figure 24:
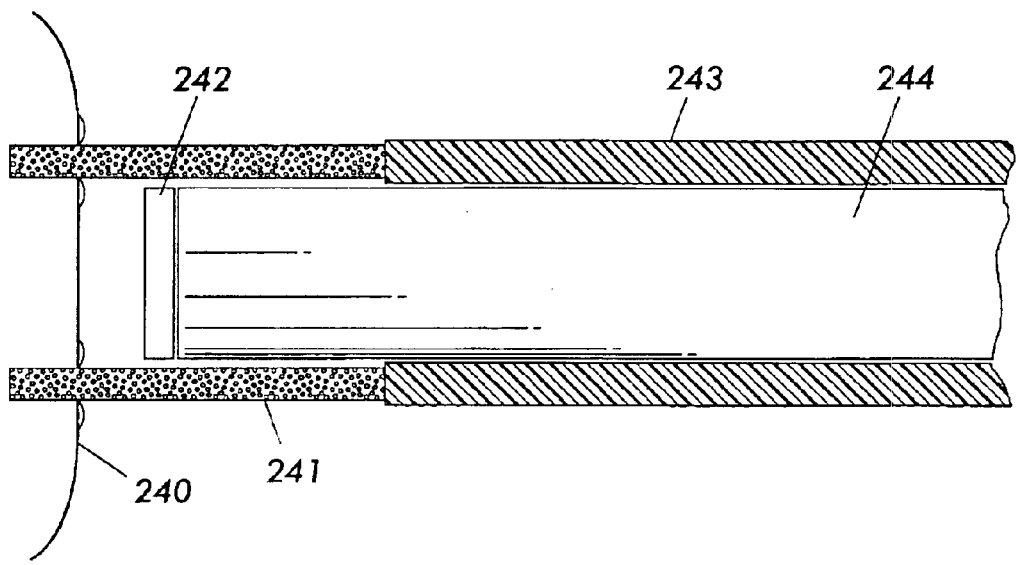

In FIG. 24, an optical transducer device is anchored to a predetermined tissue region 240, such as a cardiac muscle region, by a porous sleeve 241 that houses an optical device 242. The optical device 242 produces an optical signal that reflects off the predetermined tissue region 240. Based upon the nature of the reflection, optical device 242 produces optical signals corresponding to the characteristics of the predetermined tissue region 240. These optical signals are transmitted over an optical cable 244 within a housing 243.

Figure 25:
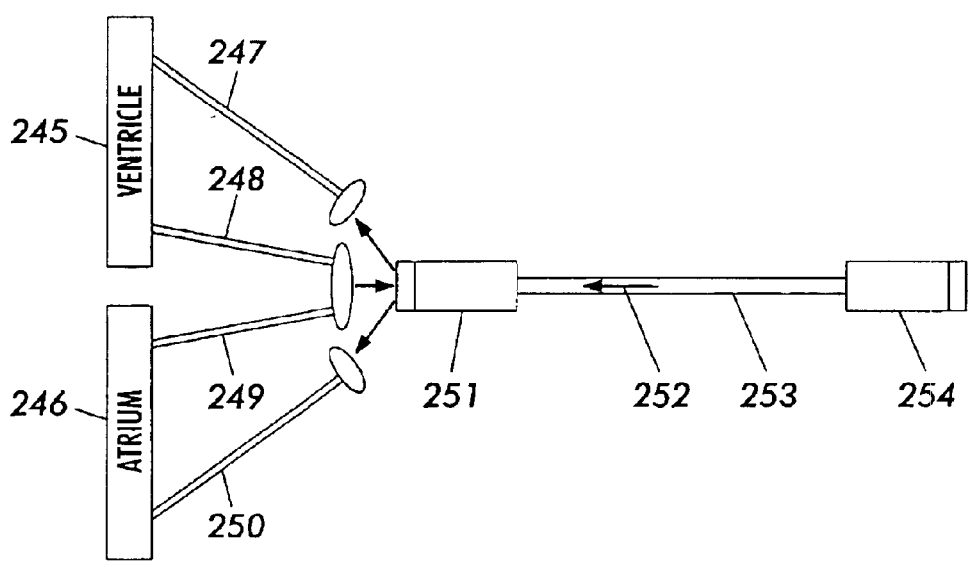

In FIG. 25, an optical transducer device for a cardiac region is illustrated. An optical device 251 produces light that is fed along fiber optics 247 and 250 to a ventricle area of the heart and an atrium area of the heart, respectively. The light is reflected off these areas and fed back to the optical device 251 through fiber optics 248 and 249. Based upon the nature of the reflection, optical device 251 produces optical signals corresponding to the characteristics of the monitored areas. These optical signals 252 are transmitted over an optical cable 253 to a control unit device 254 at a proximal end of the optical cable 253.

Figure 26:
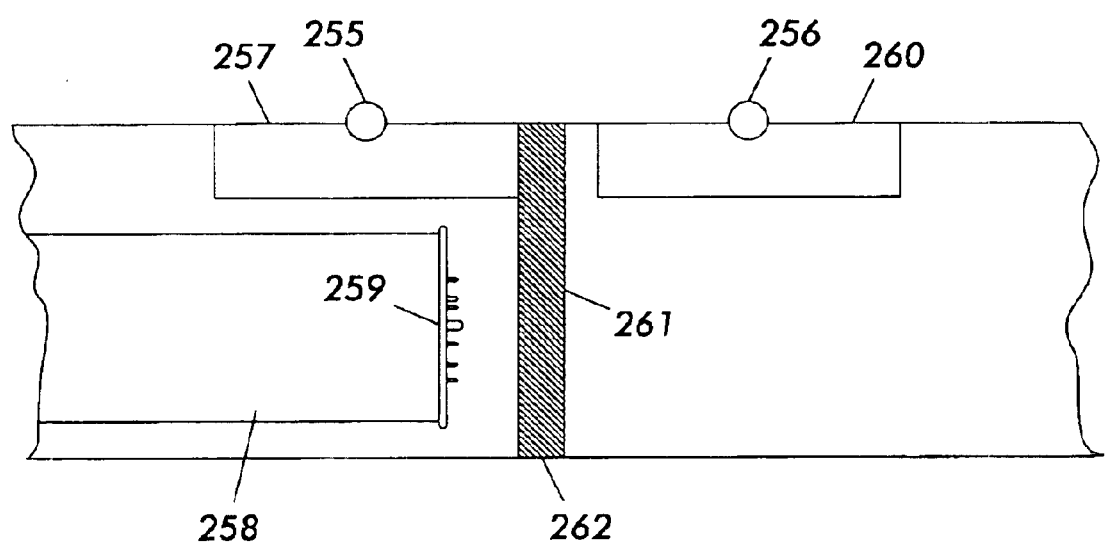

FIG. 26 illustrates one embodiment of an optical sensor. In FIG. 26, a fiber optic bundle 258 includes individual fiber optics 259. One of the fiber optics produces the reference light that is reflected off flap 261 within the optical sensor. The flap 261 will move between stops 257 and 260 based on characteristics within a predetermined tissue region. As the flap 261 moves on pivot 262, the light is reflected at different angles and thus is collected by a different fiber in the fiber optic bundle, depending upon the angle of reflection. In this way, the characteristics of the predetermined tissue region can be measured.

Figure 63:
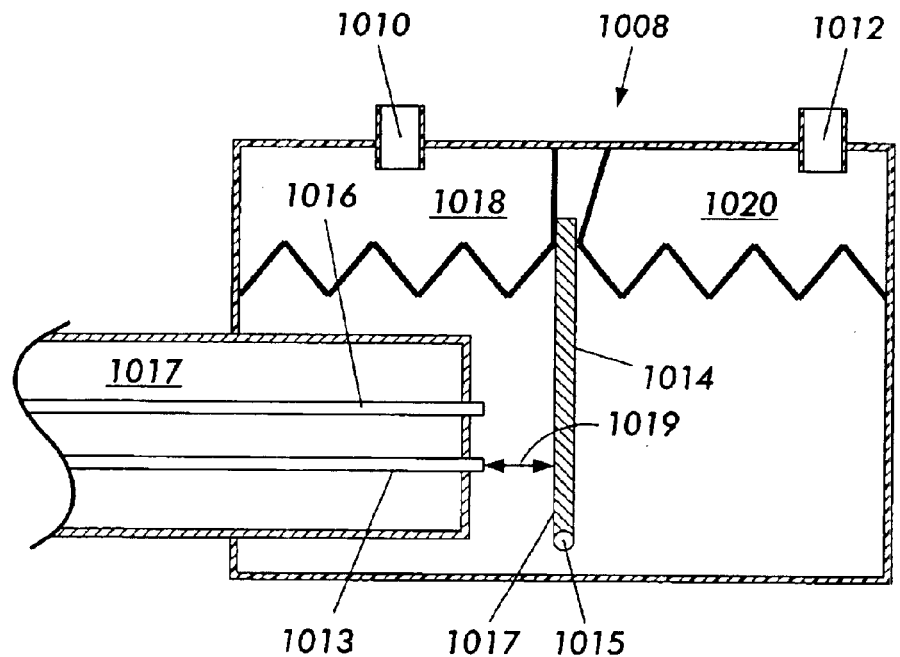
Figure 64:
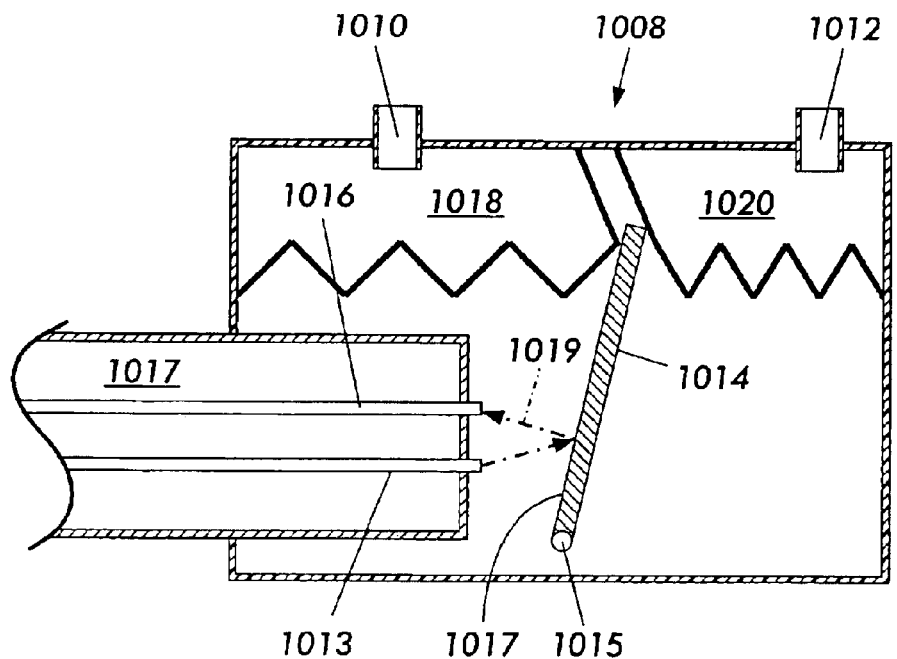

FIGS. 63 and 64 illustrate one embodiment of an optical sensor 1008. In FIGS. 63 and 64, a fiber optic bundle 1017 includes individual fiber optics 1013 and 1016. One of the fiber optics 1013 produces the reference light that is reflected off flap 1014 within the optical sensor 1008. The flap 261 will move based on muscle contractions of muscle tissue 1018 and 1020 in a predetermined tissue region that is within the optical sensor 1008 through openings 1010 and 1012. As the flap 1014 moves on pivot 1015, the light is reflected at different angles and thus is collected by a different fiber 1016 in the fiber optic bundle, depending upon the angle of reflection. In this way, the characteristics of the predetermined tissue region can be measured.

Figure 62:
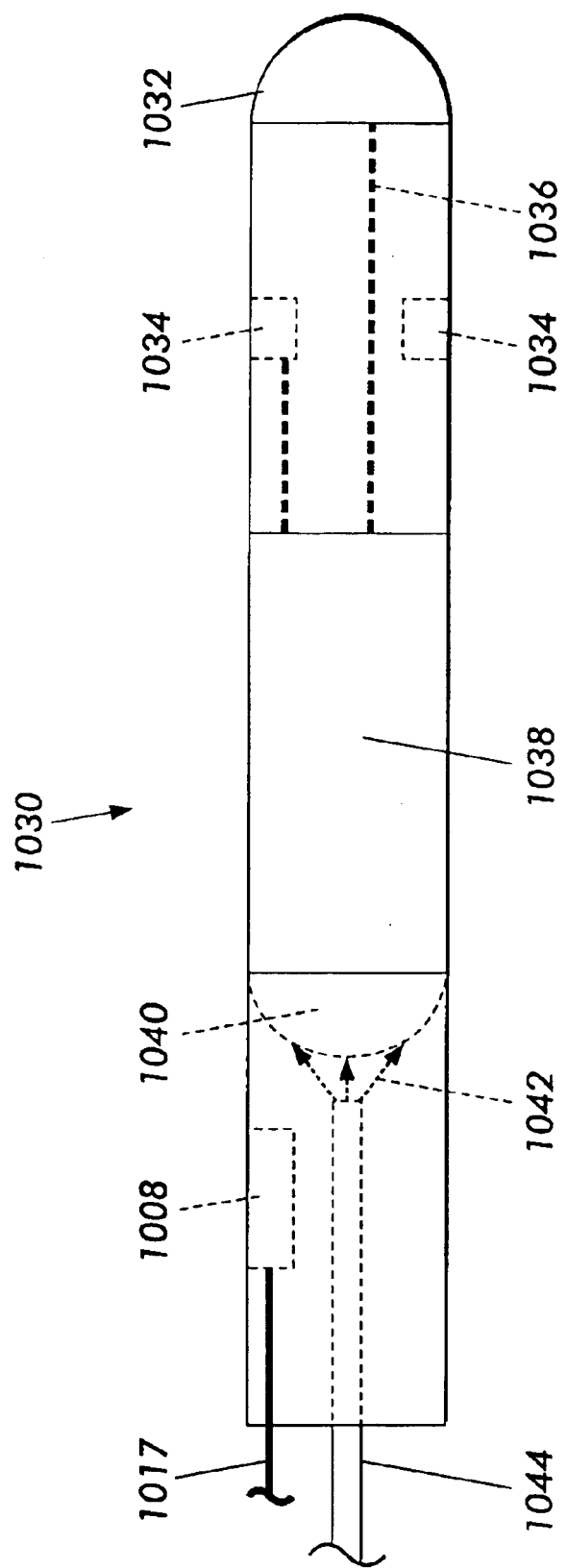
FIGS. 62 through 65 are schematics of various optical pressure transducers according to some or all of the concepts of the present invention.

FIG. 62 is an optical sensor and stimulation device 1030 for a photonic catheter. In FIG. 62, the optical sensor and stimulation device 1030 includes a ring electrode 1034 and a tip electrode 1032 to sense or stimulate a predetermined tissue region. The ring electrode 1034 and a tip electrode 1032 are connected to a control circuit 1038 that produces energy to enable the ring electrode 1034 and tip electrode 1032 to stimulate the predetermined tissue region or enables the ring electrode 1034 and tip electrode 1032 to sense characteristics of the predetermined tissue region. Control signals from a proximal end are communicated along a fiber optic 1044 and received by sensor 1040. Sensor 1040 also receives other light signals over channel 1044 that is converted into electrical energy to be stored for later use. The sensed characteristics of the predetermined region are transmitted by device 1008 over fiber optic 1017 to the proximal end.

Figure 65:
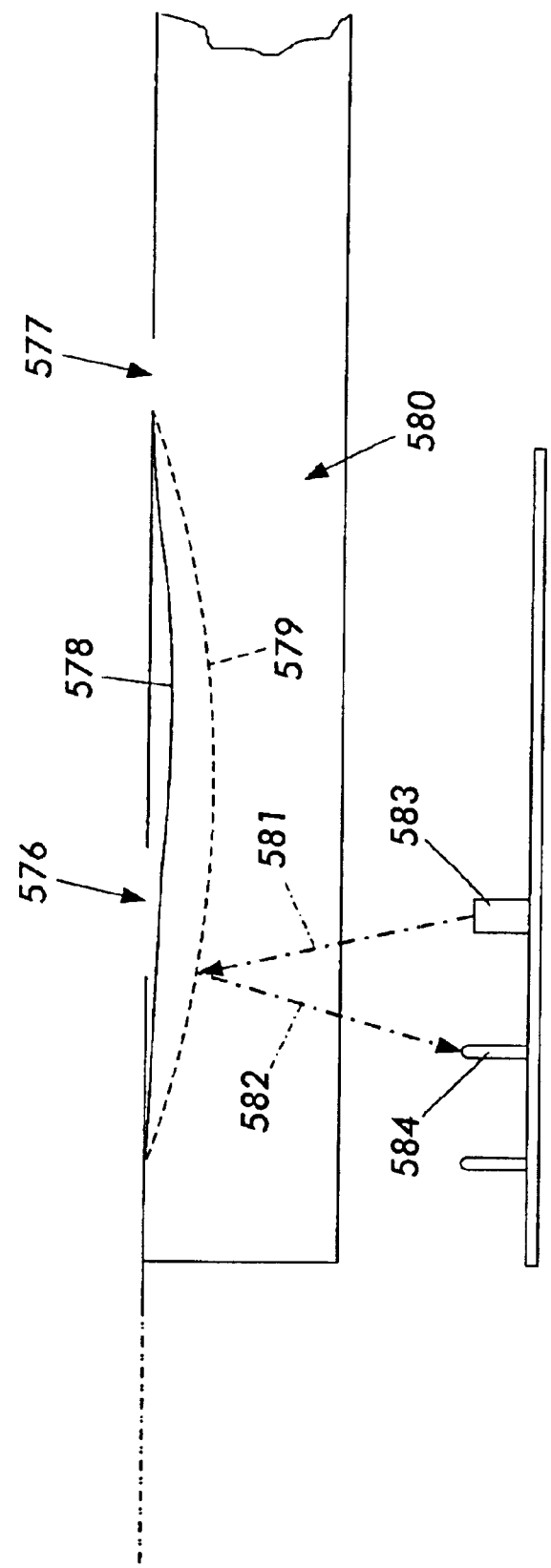

FIG. 65 illustrates a pressure pulse sensor 580. Cardiac tissue causes a mirror membrane to be at position 578 when the heart is in the diastolic interval because the pressure from the cardiac tissue decreases and in position 579 when the heart is in the systolic interval because the pressure from the cardiac tissue increases. When the mirror membrane is in position 579, laser light 581 from fiber optic 583 is reflected along ray 582 to fiber optic sensor 584. The pressure is transferred to the pressure pulse sensor 580 through openings 576 and 577.

Alternatively to the electromagnetic insult immune systems described above, a system can avoid failure during magnetic resonance imaging by determining a quiet period for a tissue implantable device and generating a magnetic resonance imaging pulse during a quiet period of the tissue implantable device. Moreover, a system can avoid failure due to an external electromagnetic field source by detecting a phase timing of an external electromagnetic field or external magnetic resonance imaging pulse field and altering operations of the tissue implantable device to avoid interfering with the detected external electromagnetic field or external magnetic resonance imaging pulse field. In these instances the tissue implantable device may be a cardiac assist device.

The concepts of the present invention may also be utilized in an electromagnetic radiation immune tissue invasive delivery system. The electromagnetic radiation immune tissue invasive delivery system has a photonic lead having a proximal end and a distal end. A storage device, located at the proximal end of the photonic lead, stores a substance to be introduced into a tissue region. A delivery device delivers a portion of the stored substance to a tissue region. A light source, in the proximal end of the photonic lead, produces a first light having a first wavelength and a second light having a second wavelength.

A wave-guide is located between the proximal end and distal end of the photonic lead. A bio-sensor, in the distal end of the photonic lead, senses characteristics of a predetermined tissue region, and a distal sensor, in the distal end of the photonic lead, converts the first light into electrical energy and, responsive to the bio-sensor, to reflect the second light back the proximal end of the photonic lead such that a characteristic of the second light is modulated to encode the sensed characteristics of the predetermined tissue region. A proximal sensor, in the proximal end of the photonic lead, converts the modulated second light into electrical energy, and a control circuit, in response to the electrical energy from the proximal sensor, controls an amount of the stored substance to be introduced into the tissue region.

In this embodiment, the sensed characteristic may be an EKG signal, a glucose level, hormone level, or cholesterol level. The stored substance may be a cardiac stimulating substance, a blood thinning substance, insulin, estrogen, progesterone, or testosterone.

The MRI compatible photonic catheter, according to the concepts of the present invention, can also be utilized to illuminate a multiple sector photodiode, whose sectors are electrically connected in series so that the voltage output of each sensor is additive, thereby producing a total output voltage in excess of what would be achieved from a single sensor.

In another embodiment of the present invention, a higher voltage and current outputs is achieved by increasing the number and size of detectors. This embodiment also provides very accurate and stable alignment of the radiation wave-guide to the sensor, and a uniform spatial intensity of the output beam that illuminates the multiple sensor sectors.

Figure 70:
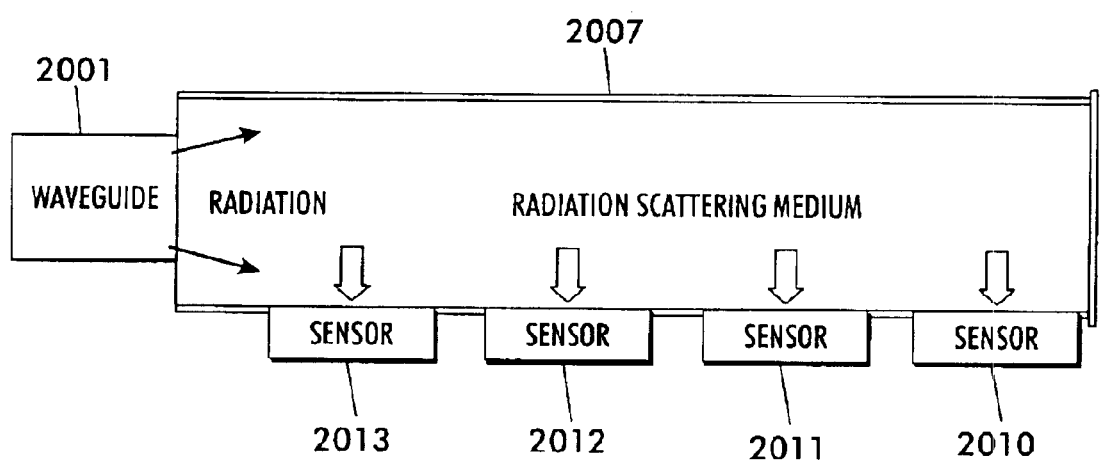
FIGS. 70 through 85 are schematics of various optical power transfer devices according to some or all of the concepts of the present invention.

An example of a MRI compatible photonic catheter being utilized to transfer power or energy to a tissue region located at a distal end of the catheter is illustrated in FIG. 70. FIG. 70 shows a wave-guide 2001 coupled to a radiation source (not shown). The wave-guide 2001 directs radiation into a radiation scattering medium 2007. Attached to the surface of the radiation scattering medium 2007 are multiple radiation sensors 2010–2013, mounted along the axis of scattering medium 2007, for receiving and converting incident radiation into electrical energy. The multiple radiation sensors 2010–2013 are electrically connected in series so that the voltage output of each sensor is additive, thereby producing a total output voltage in excess of what would be achieved from a single sensor.

The physical realization of the sensors is either a plurality of phototransistors or a plurality of photodiodes functioning as light-detecting elements. In operation, the sensor is first reset with a reset voltage that places an electronic charge across the capacitance associated with the diode. Electronic charge produced by, for example, a photodiode, when exposed to illumination, causes charge of the diode capacitance to dissipate in proportion to the incident illumination intensity. At the end of an exposure period, the change in diode capacitance charge is collected as electrical energy and the photodiode is reset.

Manipulating or adjusting the charge integration function of the sensor can modify the creation of energy by the sensors. Charge integration function manipulation can be realized by changing of an integration time, $T_{int}$, for the sensor. Changing the integration time, $T_{int}$, changes the start time of the charge integration period.

Integration time, $T_{int}$, is the time that a control signal is not set at a reset level. When the control signal is not at a reset value, the sensor causes charge to be transferred or collected therefrom. The timing of the control signal causes charge to be transferred or collected from the sensor for a shorter duration of time or longer duration of time. This adjustment can be used to manage the charge in the sensor so that the sensor does not become saturated with charge as well as to manage the current output of the sensor.

Another conventional way of manipulating the charge integration function is to use a stepped or piecewise discrete-time charge integration function. By using a stepped or piecewise discrete charge integration function, the charge in the sensor can be further managed so that the sensor does not become saturated with charge as well as to manage the current output of the sensor.

The radiation scattering medium 2007 and multiple sensors 2010–2013 are mounted such that there is little or no surface of the scattering medium that is not covered by a sensor. Any areas that are not covered by sensors are preferably covered with an internally reflective coating that directs incident radiation back into the scattering medium 2007 for absorption by the sensors 2010–2013. Together these features ensure that the sensors 2010–2013 absorb a maximum amount of radiation.

Figure 71:
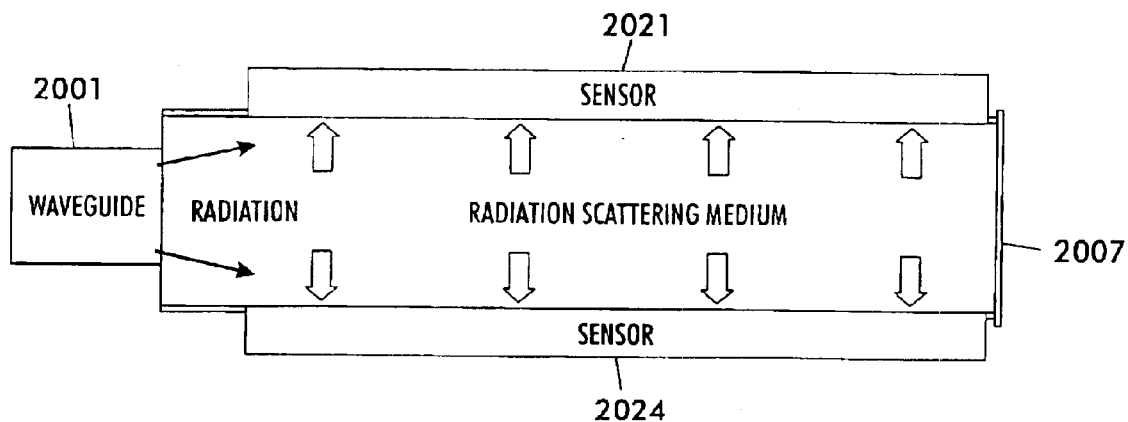
Figure 72:
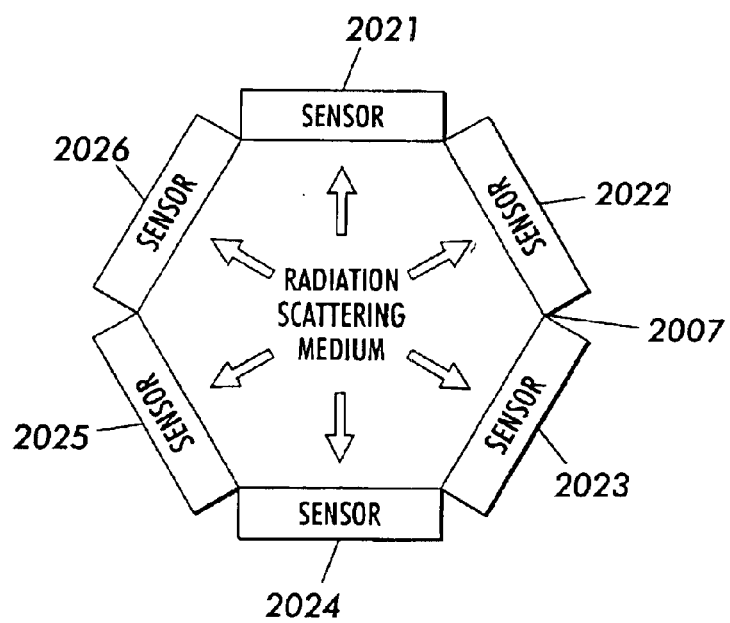

In FIGS. 71 and 72, multiple sensors 2021–2026 are alternately mounted circumferentially along the periphery of the scattering medium 2007, for receiving and converting incident radiation into electrical energy. The multiple radiation sensors 2021–2026 are electrically connected in series so that the voltage output of each sensor is additive, thereby producing a total output voltage in excess of what would be achieved from a single sensor.

Figure 73:
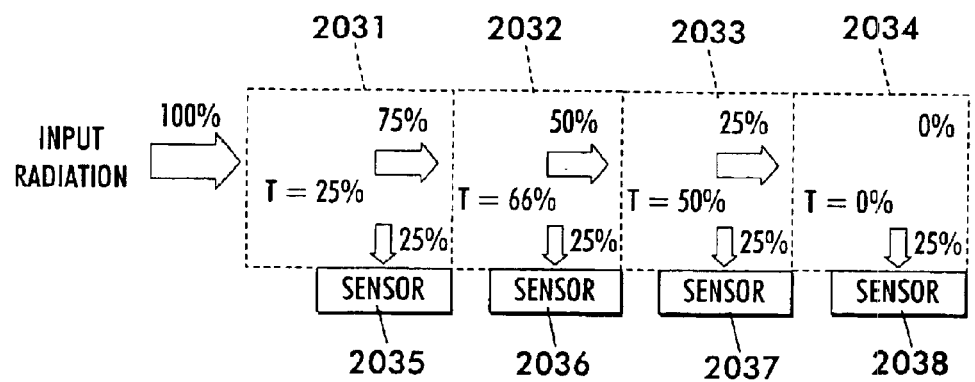

In FIG. 73, radiation scattering medium 2031–2034 with a decreasing radiation transmission rate along the axis of the medium 2031–2034 is used. A scattering medium 2031–2034 with these properties would be used when sensors 2035–2038 are electrically connected in series with consecutive sensors in the electrical circuit placed further along the axial direction of the scattering medium. This feature ensures that each sensor receives an equal exposure of radiation, produces a similar output current, thereby ensuring that the output current of the series circuit including all sensors is not limited by the output current of any individual sensor due to limited incident radiation.

Figure 74:
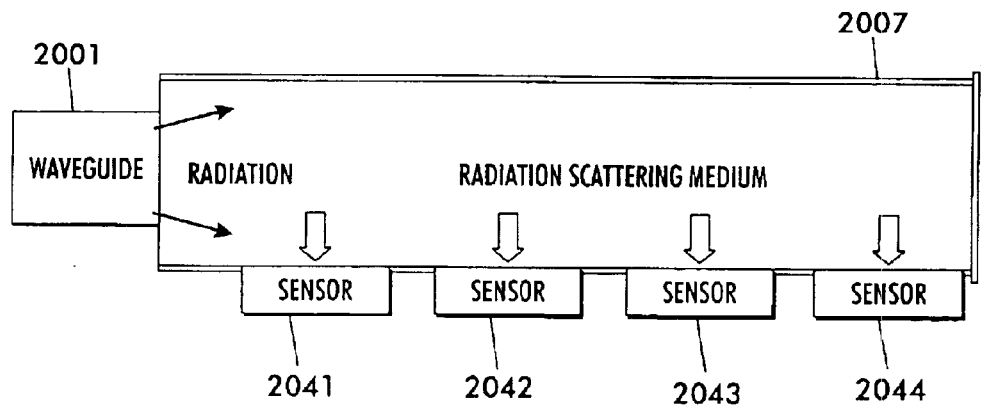

In FIG. 74, multiple sensors 2041–2044 of varying size along the axis of the scattering medium 2007 are used. By placing larger sensors towards the distal end of the scattering medium 2007, these sensors 2043–2044 receive an exposure of radiation equal to more proximally positioned sensors 2041–2042 and therefore produce equivalent output currents, even though the radiation intensity at the distal end of the scattering medium 2007 may be less than the radiation intensity at the proximal end of the scattering medium 2007.

Figure 75:
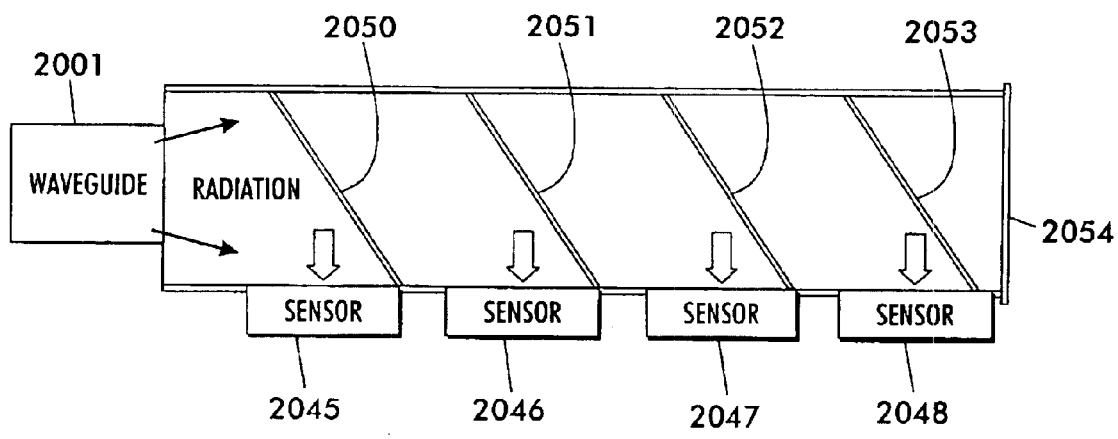

In FIG. 75, a wave-guide 2001 is coupled to a radiation source (not shown) to direct radiation into a second wave-guide 2054 with multiple radiation beam splitters 2050–2053 located along the optical axis of the wave-guide. Attached to the second wave-guide 2054 are multiple radiation sensors 2045–2048, mounted along the axis of the wave-guide 2054, for receiving and converting incident radiation into electrical energy. The multiple radiation sensors 2045–2048 are electrically connected in series so that the voltage output of each sensor is additive, thereby producing a total output voltage in excess of what would be achieved from a single sensor. The multiple sensors 2045–2048 are mounted such that there is little or no surface of the second wave-guide 2054 that is not covered by either a sensor or internally reflective coating. Together these features ensure that the sensors 2045–2048 absorb a maximum amount of radiation.

Figure 76:
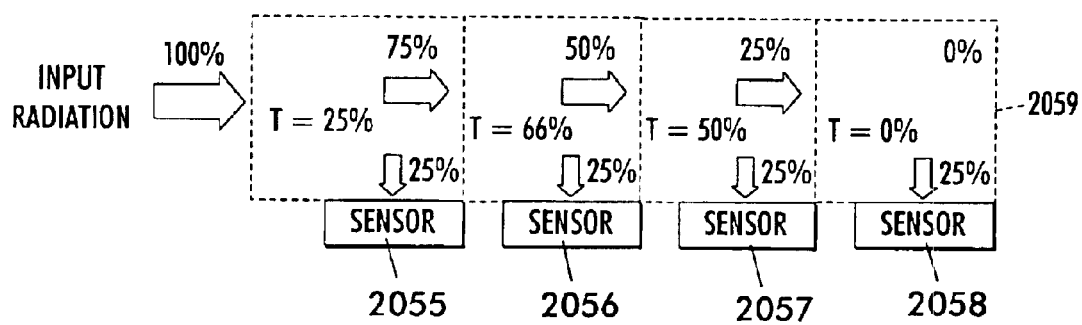

In FIG. 76, a second wave-guide 2059 with beam splitters that have decreasing radiation transmission rates along the axis of the medium 2059 is used. This feature would be used when sensors 2055–2058 are electrically connected in series with consecutive sensors in the electrical circuit placed further along the axial direction of the wave-guide 2059. Each sensor receives an equal exposure of radiation and produces a similar output current, thereby ensuring that the output current of the series circuit including all sensors is not limited by the output current of any individual sensor due to limited incident radiation.

Figure 77:
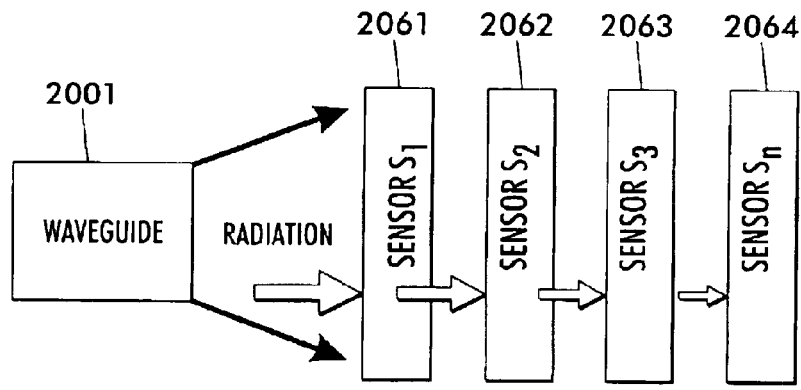

In FIG. 77, a wave-guide 2001 is coupled to a radiation source (not shown) to direct radiation onto a stack of sensors 2061–2064 such that each sensor absorbs a fraction of radiation incident upon the stack. The multiple radiation sensors 2061–2064 are electrically connected in series so that the voltage output of each sensor is additive, thereby producing a total output voltage in excess of what would be achieved from a single sensor. To ensure maximum current output of the series circuit containing all sensors 2061–2064, the radiation capture is increased with increasing distance into the sensor stack, which can be accomplished in several ways, including increasing sensor thickness that reduces radiation transfer through the consecutive sensors.

Figure 78:
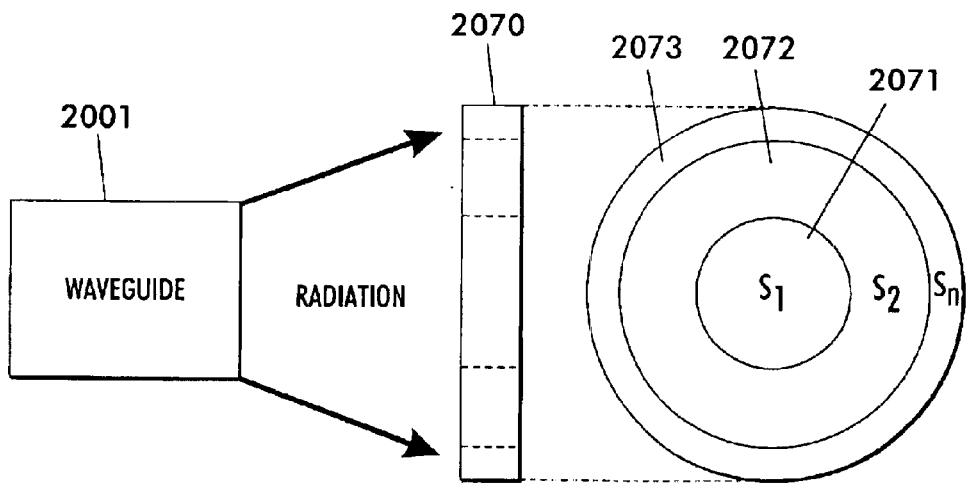

In FIG. 78, a wave-guide 2001 is coupled to a radiation source (not shown) to direct radiation onto a concentrically oriented array of sensors 2071–2073. Multiple radiation sensors 2071–2073 are electrically connected in series so that the voltage output of each sensor is additive, thereby producing a total output voltage in excess of what would be achieved from a single sensor. Each sensor has an equal area to ensure equal radiation exposure to all sensors 2071–2073, thereby producing maximum current output for the series connected sensor array. This embodiment would be used when it is desirable to over-illuminate the sensor array to ensure equal radiation exposure to all sensors.

Figure 79:
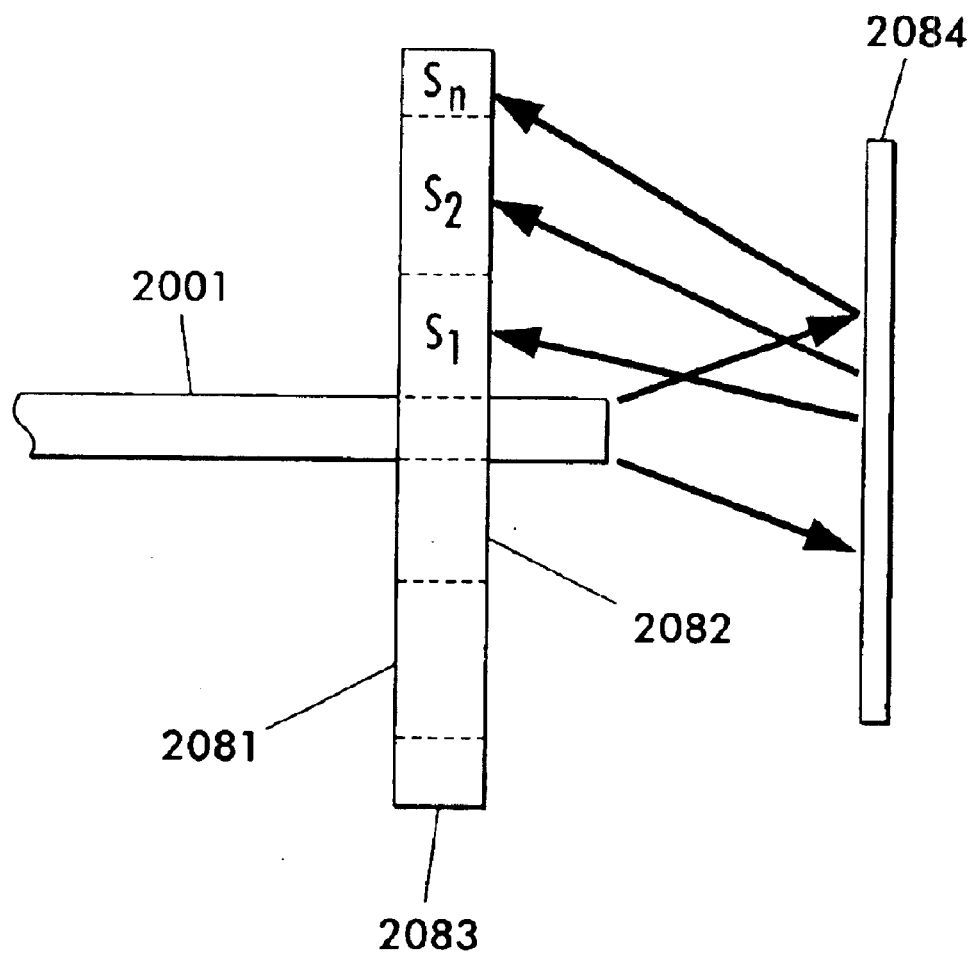

In FIG. 79, a wave-guide 2001 is coupled to a radiation source (not shown) to direct radiation onto a reflective grating 2084 that disperses 4radiation uniformly over the surface of multiple concentrically located sensors 2081–2083. The multiple radiation sensors are electrically connected in series so that the voltage output of each sensor is additive, thereby producing a total output voltage in excess of what would be achieved from a single sensor.

Figure 80:
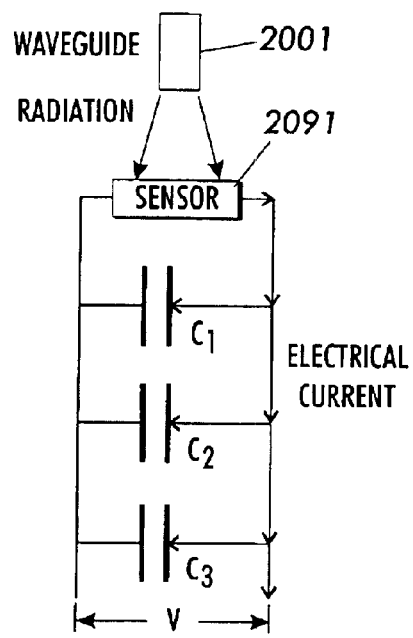

In FIG. 80, a wave-guide 2001 is coupled to a radiation source (not shown) to direct radiation onto a single radiation sensor 2091 that is connected to multiple capacitors ($C_1$, $C_2$, $C_3$, ..., $C_n$) electrically connected in parallel, enabling simultaneous charging of the capacitors ($C_1$, $C_2$, $C_3$, ... $C_n$) by the output voltage of the single sensor 2091. The voltage of each capacitor is controlled by the duration of the single pulse of radiation incident upon the single sensor.

Figure 81:
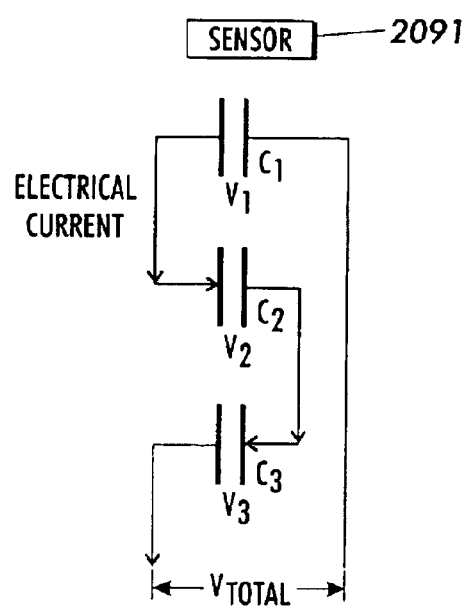

In FIG. 81, the charged capacitors ($C_1$, $C_2$, $C_3$, ..., $C_n$) are switchable to a series electrical circuit so that the voltage output of each capacitor is additive, thereby producing a total output voltage in excess of what would be achieved from a single capacitor.

Figure 82:
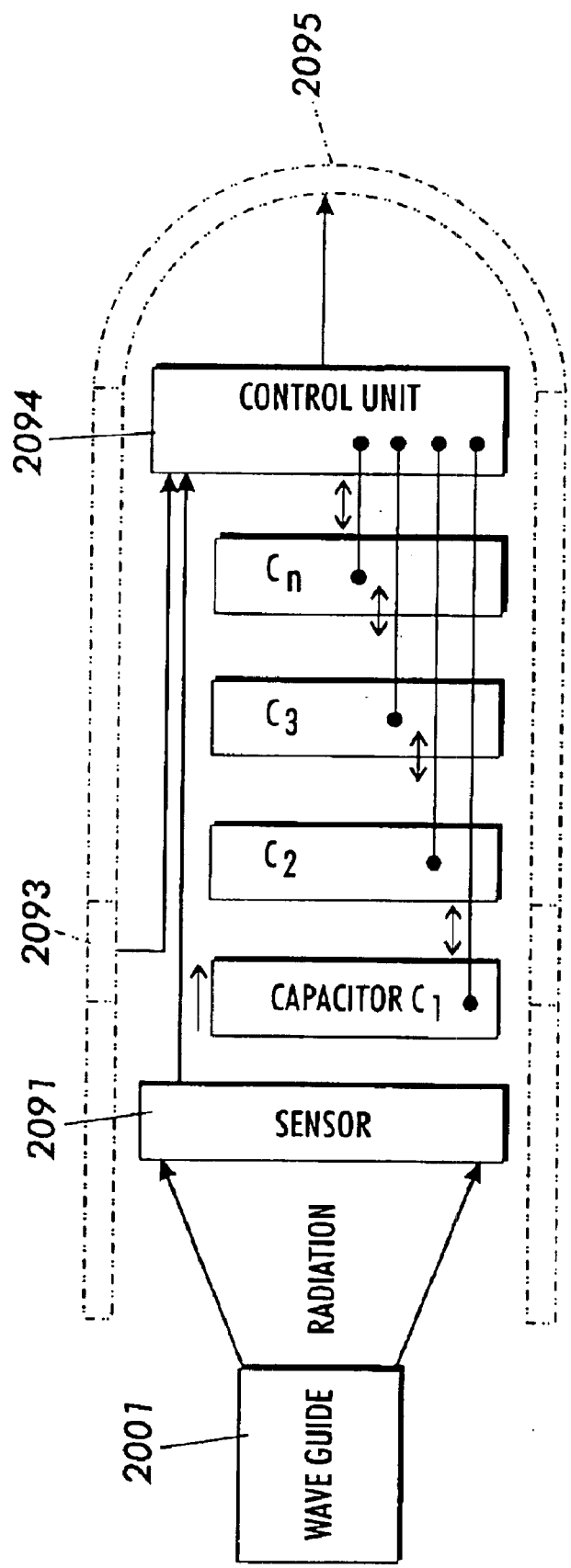

In FIG. 82, a catheter features a solid-state control circuit 2094 to manage capacitor charging, switching, and discharging functions, as well as other distal control functions. The control circuit 2094 is powered by electrical energy supplied by the illuminated sensor 2091. Additional features of this illustrated catheter include a housing and pacing electrodes 2093 and 2095.

Variable capacitance capacitors can be utilized that are tuned to precisely match individual capacitor capacitances, thereby providing extraordinary control over output voltage and power.

In FIGS. 81 and 82, the parallel electrical circuit ensures that each capacitor is charged to the same voltage level, ensuring a predictable output voltage when the parallel charged capacitors are connected in series and discharged. Moreover, the absence of multiple sensor sectors ensures that spatial variation in illumination intensity between sectors will not minimize the current of any one sector and thereby the entire circuit. Furthermore, the total energy dissipated by the series connected electrical circuit is determined by parameters that are easy to control; such as, the pre-selected capacitance of the capacitors (Power=$CV^2/2$), as well as the intensity and duration of the radiation pulse and duration of the discharge pulse which are controlled by the solid state control circuit. The diameter of the single sensor 2091 is limited only by the size of the radiation wave-guide 2001. Lastly, reliability is improved due to reduced switching operations.

Figure 83:
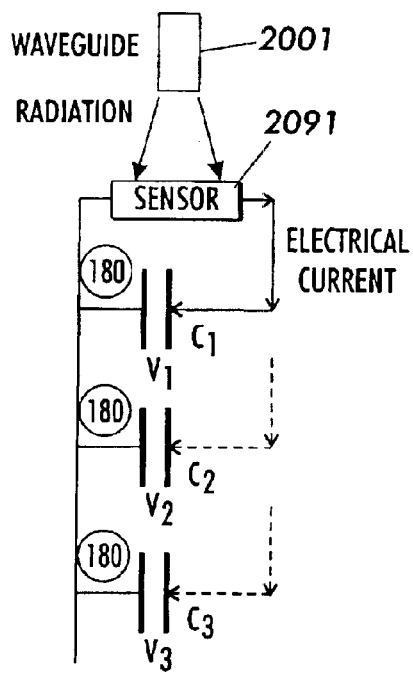

In FIG. 83, a wave-guide 2001 is coupled to a radiation source (not shown) to direct radiation onto a single radiation sensor 2091 that is sequentially connected to multiple capacitors ($C_1$, $C_2$, $C_3$, ..., $C_n$) for charging. The voltage of each capacitor is controlled by the duration of the radiation pulse incident upon the surface of the single sensor 2091.

Figure 84:
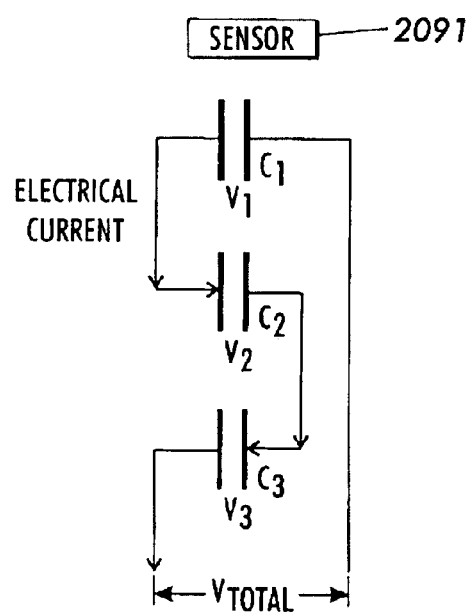

In FIG. 84, the capacitors ($C_1$, $C_2$, $C_3$, ..., $C_n$) are subsequently connected in series for discharging, thereby producing a total output voltage in excess of what would be achieved from a single sensor or single capacitor. A solid-state control circuit (not shown) is utilized to manage capacitor charging, switching, and discharging functions, as well as other distal control functions. The control circuit is powered by electrical energy supplied by the sensor 2091.

The electrical measurements of the charging characteristics of each capacitor are determined prior to utilizing the catheter. This calibration information is then pre-programmed into a proximally located control circuit to determine the duration and intensity of the radiation pulse required to achieve a specific voltage across the capacitor, thereby providing a predictable output voltage when the parallel charged capacitors are connected in series and discharged.

In FIGS. 83 and 84, the sequentially charging electrical circuit enables each capacitor to be charged with a pre-determined pulse intensity and duration, ensuring a predictable output voltage when the parallel charged capacitors are connected in series and discharged. The absence of multiple sensor sectors ensures that spatial variation in illumination intensity between sectors will not minimize the current of any one sector and thereby the entire circuit. Furthermore, the total energy dissipated by the series connected electrical circuit is determined by parameters that are easy to control; such as, the pre-selected capacitance of the capacitors (Power=$CV^2/2$), as well as the intensity and duration of the radiation pulse and duration of the discharge pulse which are controlled by the solid state control circuit. The diameter of the sensor 2091 is limited only by the size of the radiation wave-guide 2001.

Figure 85:
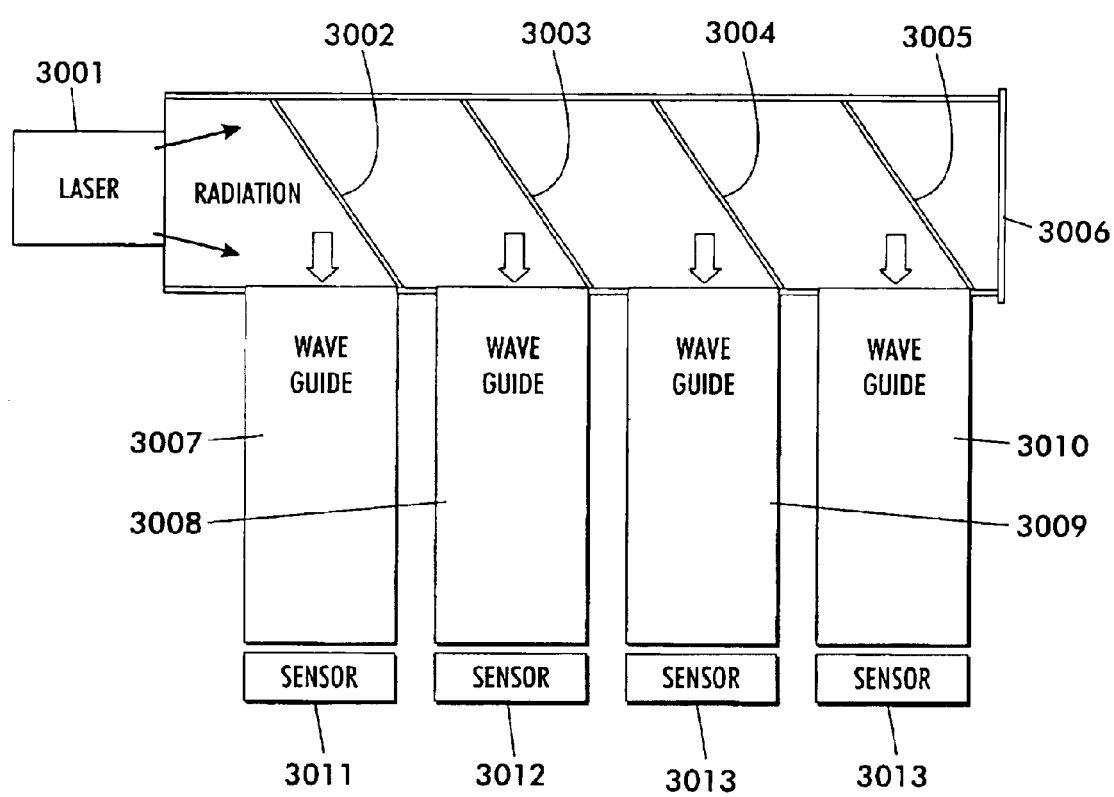

In FIG. 85, the output energy of a single radiation source 3001 is split into multiple beams by radiation beam splitter 3006 having multiple beam splitters 3002–3005 and directed into multiple wave-guides 3007–3010 to direct radiation onto multiple radiation sensors 3011–3013. Redundant sensors 3011–3013 are connected in series to produce a total output voltage in excess of what would be achieved from a single sensor.

Power transfer can also be realized by a radiation source coupled to a wave-guide to direct radiation onto a single radiation sensor. This photonic system design is repeated with additional radiation sources, additional wave-guides, and additional radiation sensors. Redundant sensors are connected in series to produce a total output voltage in excess of what would be achieved from a single sensor.

These embodiments may also utilize a variable intensity radiation source that can be used to vary the output current of the series connected sensors. Moreover, this embodiment may include a control circuit that controls the period and nature of the charge integration function of the sensors to maximize the output current of the sensors.

It is noted that the power transfer embodiments illustrated in FIGS. 70–85 can be combined with the photonic sensing embodiments illustrated in FIGS. 5–20 such that the photonic catheter has both power transfer and sensing capabilities.

The concepts of the present invention may also be utilized in implanted insulin pumps. Implanted insulin pumps typically consist of two major subsystems: a pump assembly for storing and metering insulin into the body, and a sensor for measuring glucose concentration. The two assemblies are typically connected by a metallic wire lead encased in a biocompatible catheter. The pump and sensor assemblies are typically located in separate locations within the body to accommodate the larger size of the reservoir and pump assembly (which is typically located in the gut), and to enable the sensor (typically located near the heart) to more accurately measure glucose concentration.

The output of the sensor is delivered to the reservoir and pump assembly as a coded electrical signal where it is used to determine when and how much insulin to deliver into the body. The fact that the lead connecting the two assemblies is a wire lead makes it susceptible to interference from external magnetic fields, particularly the intense magnetic fields used in MRI imaging. Interference from MRI fields can induce electrical voltages in the leads that can damage the pump assembly and cause incorrect operation of the pump which could lead to patient injury possibly even death.

Induced electrical currents can also cause heating of the lead that can also damage the pump and cause incorrect operation of the pump and injury to the patient due to pump failure as well as thermogenic injury to internal tissues and organs. Shielding of the reservoir and pump assembly and sensor assembly can reduce direct damage to these devices, but cannot prevent induced electrical voltages and currents from interfering with and damaging the devices.

According to the concepts of the present invention, a photonic lead replaces the metallic wire connecting the reservoir and pump assembly and sensor assembly with a wave-guide such as an optical fiber. The sensor assembly is also modified to include means to transduce the electrical signal generated by the sensor into an optical signal that is then transmitted to reservoir and pump assembly over the wave-guide. This transduction means can be achieved by various combinations of optical emitters, optical attenuators, and optical sensors located in either the sensor assembly or reservoir and pump assembly.

As noted above, the present invention is an implantable device that is immune or hardened to electromagnetic insult or interference.

In one embodiment of the present invention as illustrated in the figures, an implantable pacemaker or a cardiac assist system is used to regulate the heartbeat of a patient. The implantable cardiac assist system is constructed of a primary device housing that has control circuitry therein. This control circuitry may include a control unit such a microprocessor or other logic circuits and digital signal processing circuits. The primary device housing may also include an oscillator, memory, filtering circuitry, an interface, sensors, a power supply, and/or a light source.

The microprocessor may be an integrated circuit for controlling the operations of the cardiac assist system. The microprocessor integrated circuit can select a mode of operation for the cardiac assist system based on predetermined sensed parameters. In one embodiment, the microprocessor integrated circuit isolates physiological signals using an analog or digital noise filtering circuit.

The primary device housing also can contain circuitry to detect and isolate crosstalk between device pulsing operations and device sensing operations, a battery power source and a battery power source measuring circuit. In such an embodiment the microprocessor integrated circuit can automatically adjust a value for determining an elective replacement indication condition of a battery power source. The value is automatically adjusted by the microprocessor integrated circuit in response to a measured level of a state of the battery power source. The measured level is generated by the battery power source measuring circuit that is connected to the battery power source.

The microprocessor integrated circuit can be programmable from a source external of the cardiac assist system and can provide physiological or circuit diagnostics to a source external of the cardiac assist system.

The microprocessor integrated circuit may also include a detection circuit to detect a phase timing of an external electromagnetic field. The microprocessor integrated circuit alters its operations to avoid interfering with the detected external electromagnetic field. Moreover, the cardiac assist system would include sensors may detect a heart signal and to produce a sensor signal therefrom and a modulator to modulate the sensor signal to differentiate the sensor signal from electromagnetic interference or a sampling circuit to sample the sensor signal multiple times to differentiate the sensor signal from electromagnetic interference, undesirable acoustic signals, large muscle contractions, or extraneous infrared light.

The primary device housing has formed around it, in a preferred embodiment, a shield. The shield can be formed of various composite materials so as to provide an electromagnetic shield around the primary housing. Examples of such materials are metallic shielding or polymer or carbon composites such as carbon fullerenes. This shield or sheath around the primary device housing shields the primary device housing and any circuits therein from electromagnetic interference.

The cardiac assist system also includes a lead system to transmit and receive signals between a heart and the primary device housing. The lead system may be a fiber optic based communication system, preferably a fiber optic communication system contains at least one channel within a multi-fiber optic bundle, or the lead system may be a plurality of electrical leads. The lead system is coated with electromagnetic interference resistant material.

With respect to the electrical lead system, the plurality of electrical leads has a second shielding therearound, the second shielding preventing the electrical leads from conducting stray electromagnetic interference. The second shielding can be a metallic sheath to prevent the electrical leads from conducting stray electromagnetic interference; a carbon composite sheath to prevent the electrical leads from conducting stray electromagnetic interference; or a polymer composite sheath to prevent the electrical leads from conducting stray electromagnetic interference. The electrical leads may either be unipolar, bipolar or a combination of the two. Moreover, the lead system itself may be a combination of fiber optic leads and electrical leads wherein these electrical leads can be either unipolar, bipolar or a combination of the two.

The lead systems may include a sensing and stimulation system at an epicardial-lead interface with a desired anatomical cardiac tissue region. The sensing and stimulation system may include optical sensing components to detect physiological signals from the desired anatomical cardiac tissue region and/or electrical sensing components to detect physiological signals from the desired anatomical cardiac tissue region. The sensing and stimulation system may also include optical pulsing components to deliver a stimulus of a predetermined duration and power to the desired anatomical cardiac tissue region and/or electrical pulsing components to deliver a stimulus of a predetermined duration and power to the desired anatomical cardiac tissue region. The sensing and stimulation system may also include hydrostatic pressure sensing components to detect physiological signals from the desired anatomical cardiac tissue region.

Although the leads may be fiber optic strands or electrical leads with proper shielding, the actual interface to the tissue, the electrodes, cannot be shielded because the tissue needs to receive the stimulation from the device without interference. This causes the electrodes to be susceptible to electromagnetic interference or insult, and such insult can cause either damage to the tissue area or the circuitry at the other end. To realize immunity from the electromagnetic interference or insult, each electrode has an anti-antenna geometrical shape. The anti-antenna geometrical shape prevents the electrode from picking up and conducting stray electromagnetic interference.

Moreover, the primary device housing, may include for redundancy filtering circuits as the ends of the electrical leads at the primary housing interface to remove stray electromagnetic interference from a signal being received from the electrical lead. The filters may be capacitive and inductive filter elements adapted to filter out predetermined frequencies of electromagnetic interference.

In addition to the electromagnetic interference shielding, the primary device housing, and lead system, whether it is a fiber optic system or electrical lead system can be coated with a biocompatible material. Such a biocompatible material is preferably a non-permeable diffusion resistant biocompatible material.

In another embodiment of the present invention as illustrated in the figures, an implantable pacemaker or a cardiac assist system is used to regulate the heartbeat of a patient. The implantable cardiac assist system is constructed of a primary device housing that has control circuitry therein. This control circuitry may include a control unit such a microprocessor or other logic circuits and digital signal processing circuits. The primary device housing may also include an oscillator, memory, filtering circuitry, an interface, sensors, a power supply, and/or a light source. In a preferred embodiment, the control circuitry including the oscillator and an amplifier operate at an amplitude level above that of an induced signal from a magnetic-resonance imaging field.

The microprocessor may be an integrated circuit for controlling the operations of the cardiac assist system. The microprocessor integrated circuit can select a mode of operation for the cardiac assist system based on predetermined sensed parameters. In one embodiment, the microprocessor integrated circuit isolates physiological signals using an analog or digital noise filtering circuit.

The primary device housing also can contain circuitry to detect and isolate crosstalk between device pulsing operations and device sensing operations, a battery power source and a battery power source measuring circuit. In such an embodiment the microprocessor integrated circuit can automatically adjust a value for determining an elective replacement indication condition of a battery power source. The value is automatically adjusted by the microprocessor integrated circuit in response to a measured level of a state of the battery power source. The measured level is generated by the battery power source measuring circuit that is connected to the battery power source.

The microprocessor integrated circuit can be programmable from a source external of the cardiac assist system and can provide physiological or circuit diagnostics to a source external of the cardiac assist system.

The cardiac assist system also includes a lead system to transmit and receive signals between a heart and the primary device housing. The lead system may be a fiber optic based communication system, preferably a fiber optic communication system contains at least one channel within a multi-fiber optic bundle, or the lead system may be a plurality of electrical leads. The lead system is coated with electromagnetic interference resistant material.

The cardiac assist system further includes a detection circuit. The detection circuit is located in the primary device housing and detects an electromagnetic interference insult upon the cardiac assist system. Examples of such detection circuits are a thermistor heat detector; a high frequency interference detector; a high voltage detector; and/or an excess current detector. The control circuit places the cardiac assist system in an asynchronous mode upon detection of the electromagnetic interference insult by the detection system.

With respect to the electrical lead system, the plurality of electrical leads has a second shielding therearound, the second shielding preventing the electrical leads from conducting stray electromagnetic interference. The second shielding can be a metallic sheath to prevent the electrical leads from conducting stray electromagnetic interference; a carbon composite sheath to prevent the electrical leads from conducting stray electromagnetic interference; or a polymer composite sheath to prevent the electrical leads from conducting stray electromagnetic interference. The electrical leads may either be unipolar, bipolar or a combination of the two. Moreover, the lead system itself may be a combination of fiber optic leads and electrical leads wherein these electrical leads can be either unipolar, bipolar or a combination of the two.

The lead systems may include a sensing and stimulation system at an epicardial-lead interface with a desired anatomical cardiac tissue region. The sensing and stimulation system may include optical sensing components to detect physiological signals from the desired anatomical cardiac tissue region and/or electrical sensing components to detect physiological signals from the desired anatomical cardiac tissue region. The sensing and stimulation system may also include optical pulsing components to deliver a stimulus of a predetermined duration and power to the desired anatomical cardiac tissue region and/or electrical pulsing components to deliver a stimulus of a predetermined duration and power to the desired anatomical cardiac tissue region. The sensing and stimulation system may also include hydrostatic pressure sensing components to detect physiological signals from the desired anatomical cardiac tissue region.

Although the leads may be fiber optic strands or electrical leads with proper shielding, the actual interface to the tissue, the electrodes, cannot be shielded because the tissue needs to receive the stimulation from the device without interference. This causes the electrodes to be susceptible to electromagnetic interference or insult, and such insult can cause either damage to the tissue area or the circuitry at the other end. To realize immunity from the electromagnetic interference or insult, each electrode has an anti-antenna geometrical shape. The anti-antenna geometrical shape prevents the electrode from picking up and conducting stray electromagnetic interference.

Moreover, the primary device housing, may include for redundancy filtering circuits as the ends of the electrical leads at the primary housing interface to remove stray electromagnetic interference from a signal being received from the electrical lead. The filters may be capacitive and inductive filter elements adapted to filter out predetermined frequencies of electromagnetic interference.

The primary device housing has formed around it, in a preferred embodiment, a shield. The shield can be formed of various composite materials so as to provide an electromagnetic shield around the primary housing. Examples of such materials are metallic shielding or polymer or carbon composites such as carbon fullerenes. This shield or sheath around the primary device housing shields the primary device housing and any circuits therein from electromagnetic interference.

In addition to the electromagnetic interference shielding, the primary device housing, and lead system, whether it is a fiber optic system or electrical lead system can be coated with a biocompatible material. Such a biocompatible material is preferably a non-permeable diffusion resistant biocompatible material.

In a third embodiment of the present invention as illustrated in the figures, a cardiac assist system includes a primary device housing. The primary device housing has a control circuit, therein, to perform synchronous cardiac assist operations. The cardiac assist system further includes a secondary device housing that has a control circuit, therein, to perform asynchronous cardiac assist operations A detection circuit, located in either the primary or secondary device housing and communicatively coupled to the control circuits, detects an electromagnetic interference insult upon the cardiac assist system. The detection circuit can also be located in a third device housing. Examples of such detection circuits are a thermistor heat detector; a high frequency interference detector; a high voltage detector; and/or an excess current detector.

The detection circuit is communicatively coupled to the control circuits through a fiber optic communication system and/or through electromagnetic interference shielded electrical leads. The fiber optic communication system or the electromagnetic interference shielded electrical leads are coated with a biocompatible material.

The control circuit of the primary device housing terminates synchronous cardiac assist operations and the control circuit of the secondary device housing initiates asynchronous cardiac assist operations upon detection of the electromagnetic interference insult by the detection system. In this system the control circuit of the secondary device housing places the cardiac assist system in the asynchronous mode for a duration of the electromagnetic interference insult and terminates the asynchronous mode of the cardiac assist system upon detection of an absence of an electromagnetic interference insult by the detection system. The control circuit of the primary device housing terminates the synchronous mode of the cardiac assist system for the duration of the electromagnetic interference insult and re-initiates the synchronous mode of the cardiac assist system upon detection of an absence of an electromagnetic interference insult by the detection system.

The primary and secondary device housings have formed around them, in a preferred embodiment, a shield. The shield can be formed of various composite materials so as to provide an electromagnetic shield around the primary housing. Examples of such materials are metallic shielding or polymer or carbon composites such as carbon fullerenes. This shield or sheath around the primary device housing shields the primary device housing and any circuits therein from electromagnetic interference.

In addition to the electromagnetic interference shielding, the primary and secondary device housings are coated with a biocompatible material. Such a biocompatible material is preferably a non-permeable diffusion resistant biocompatible material.

The cardiac assist system also includes a lead system to transmit and receive signals between heart and the primary and secondary device housings. The lead system may be a fiber optic based communication system, preferably a fiber optic communication system contains at least one channel within a multi-fiber optic bundle, or the lead system may be a plurality of electrical leads. The lead system is coated with electromagnetic interference resistant material.

With respect to the electrical lead system, the plurality of electrical leads has a second shielding therearound, the second shielding preventing the electrical leads from conducting stray electromagnetic interference. The second shielding can be a metallic sheath to prevent the electrical leads from conducting stray electromagnetic interference; a carbon composite sheath to prevent the electrical leads from conducting stray electromagnetic interference; or a polymer composite sheath to prevent the electrical leads from conducting stray electromagnetic interference. The electrical leads may either be unipolar, bipolar or a combination of the two. Moreover, the lead system itself may be a combination of fiber optic leads and electrical leads wherein these electrical leads can be either unipolar, bipolar or a combination of the two.

The lead systems may include a sensing and stimulation system at an epicardial-lead interface with a desired anatomical cardiac tissue region. The sensing and stimulation system may include optical sensing components to detect physiological signals from the desired anatomical cardiac tissue region and/or electrical sensing components to detect physiological signals from the desired anatomical cardiac tissue region. The sensing and stimulation system may also include optical pulsing components to deliver a stimulus of a predetermined duration and power to the desired anatomical cardiac tissue region and/or electrical pulsing components to deliver a stimulus of a predetermined duration and power to the desired anatomical cardiac tissue region. The sensing and stimulation system may also include hydrostatic pressure sensing components to detect physiological signals from the desired anatomical cardiac tissue region.

Although the leads may be fiber optic strands or electrical leads with proper shielding, the actual interface to the tissue, the electrodes, cannot be shielded because the tissue needs to receive the stimulation from the device without interference. This causes the electrodes to be susceptible to electromagnetic interference or insult, and such insult can cause either damage to the tissue area or the circuitry at the other end. To realize immunity from the electromagnetic interference or insult, each electrode has an anti-antenna geometrical shape. The anti-antenna geometrical shape prevents the electrode from picking up and conducting stray electromagnetic interference.

In a fourth embodiment of the present invention, an implantable pacemaker or a cardiac assist system is used to regulate the heartbeat of a patient. The implantable cardiac assist system is constructed of a primary device housing that has control circuitry therein. This control circuitry may include a control unit such a microprocessor or other logic circuits and digital signal processing circuits. The primary device housing may also include an oscillator, memory, filtering circuitry, an interface, sensors, a power supply, and/or a light source.

The microprocessor may be an integrated circuit for controlling the operations of the cardiac assist system. The microprocessor integrated circuit can select a mode of operation for the cardiac assist system based on predetermined sensed parameters. In one embodiment, the microprocessor integrated circuit isolates physiological signals using an analog or digital noise filtering circuit.

The primary device housing also can contain circuitry to detect and isolate crosstalk between device pulsing operations and device sensing operations, a battery power source and a battery power source measuring circuit. In such an embodiment the microprocessor integrated circuit can automatically adjust a value for determining an elective replacement indication condition of a battery power source. The value is automatically adjusted by the microprocessor integrated circuit in response to a measured level of a state of the battery power source. The measured level is generated by the battery power source measuring circuit that is connected to the battery power source.

The microprocessor integrated circuit can be programmable from a source external of the cardiac assist system and can provide physiological or circuit diagnostics to a source external of the cardiac assist system.

The microprocessor integrated circuit may also include a detection circuit to detect a phase timing of an external electromagnetic field. The microprocessor integrated circuit alters its operations to avoid interfering with the detected external electromagnetic field. Moreover, the cardiac assist system would include sensors may detect a heart signal and to produce a sensor signal therefrom and a modulator to modulate the sensor signal to differentiate the sensor signal from electromagnetic interference or a sampling circuit to sample the sensor signal multiple times to differentiate the sensor signal from electromagnetic interference, undesirable acoustic signals, large muscle contractions, or extraneous infrared light.

The primary device housing has formed around it, in a preferred embodiment, a shield. The shield can be formed of various composite materials so as to provide an electromagnetic shield around the primary housing. Examples of such materials are metallic shielding or polymer or carbon composites such as carbon fullerenes. This shield or sheath around the primary device housing shields the primary device housing and any circuits therein from electromagnetic interference.

The cardiac assist system also includes a fiber optic lead system to transmit and receive signals between a heart and the primary device housing. The fiber optic communication system preferably contains at least one channel within a multi-fiber optic bundle. The lead system can be coated with electromagnetic interference resistant material.

The optic fiber lead systems may include a sensing and stimulation system at an epicardial-lead interface with a desired anatomical cardiac tissue region. The sensing and stimulation system may include optical sensing components to detect physiological signals from the desired anatomical cardiac tissue region and/or electrical sensing components to detect physiological signals from the desired anatomical cardiac tissue region (in the electrical sensing components, electrical pulses are converted to light pulses before being transmitted over the lead system). The sensing and stimulation system may also include optical pulsing components to deliver a stimulus of a predetermined duration and power to the desired anatomical cardiac tissue region and/or electrical pulsing components to deliver a stimulus of a predetermined duration and power to the desired anatomical cardiac tissue region (in the electrical delivering components, light pulses are converted to electrical pulses after the light pulses are received from the lead system). The sensing and stimulation system may also include hydrostatic pressure sensing components to detect physiological signals from the desired anatomical cardiac tissue region.

Although the leads are fiber optic strands, the actual interface to the tissue, the electrodes, cannot be fiber optics because the tissue needs to receive electrical stimulation from the device. This causes the electrodes to be susceptible to electromagnetic interference or insult, and such insult can cause either damage to the tissue area or the circuitry at the other end. To realize immunity from the electromagnetic interference or insult, each electrode has an anti-antenna geometrical shape. The anti-antenna geometrical shape prevents the electrode from picking up and conducting stray electromagnetic interference.

In addition, the primary device housing and the fiber optic lead system are coated with a biocompatible material. Such a biocompatible material is preferably a non-permeable diffusion resistant biocompatible material. The primary device housing further includes an electronic signal generator and a controlled laser light pulse generator linked to the electronic signal generator. A fiber optic light pipe for receives the laser light pulse from the controlled laser light pulse generator at a proximal end of the fiber optic light pipe. A photodiode, at a distal end of the fiber optic light pipe converts the laser light pulse back into an electrical pulse. The electrical pulse drives the cardiac electrodes coupled to the photodiode and to a cardiac muscle.

In a fifth embodiment of the present invention as illustrated in the figures, an implantable cable for transmission of a signal to and from a body tissue of a vertebrate is constructed of a fiber optic bundle having a cylindrical surface of non-immunogenic, physiologically compatible material. The fiber optic bundle is capable of being permanently implanted in a body cavity or subcutaneously. An optical fiber in the fiber optic bundle has a distal end for implantation at or adjacent to the body tissue and a proximal end. The proximal end is adapted to couple to and direct an optical signal source. The distal end is adapted to couple to an optical stimulator. The optical fiber delivers an optical signal intended to cause the optical stimulator located at a distal end to deliver an excitatory stimulus to a selected body tissue. The stimulus causes the selected body tissue to function as desired.

The optical stimulator is constructed, in a preferred embodiment, is constructed of a photoresponsive device for converting the light received from the optical signal source into electrical energy and for sensing variations in the light energy to produce control signals. A charge-accumulating device, such as a CCD, receives and stores the electrical energy produced by the photoresponsive device. A discharge control device, responsive to the control signals, directs the stored electrical energy from the charge-accumulating device to the cardiac assist device associated with the heart.

A second optical fiber has a distal end coupled to a sensor and a proximal end coupled to a device responsive to an optical signal delivered by the second optical fiber. The sensor generates an optical signal to represent a state of a function of the selected body tissue to provide feedback to affect the activity of the optical signal source.

In a sixth embodiment of the present invention, an implantable photonic cable system is constructed from a photonic cable, a light source and a light detector. The light source and the light detector form an optical sensor unit. The photonic cable, in this embodiment, receives signals from a selected tissue area and delivering signals to the selected tissue area. The system further includes transducers.

The light source illuminates a tissue area, and the light detector detects properties of the tissue by measuring the output of the light signals reflective from the tissue area. A hollow porous cylinder is used to attach the optical sensor unit to the tissue area. Preferably, the light source is a light emitting diode and the light detector is a photodiode comprising multiple channels. The multiple channels detect light emission at multiple wavelengths. Moreover, the optical sensor unit includes either a pressure-optical transducer or a reflective element mechanically driven by a moving part of the selected body tissue.

In a seventh embodiment of the present invention, a cardiac assist system is constructed of a primary device housing having a control circuit therein. A shielding is formed around the primary device housing to shield the primary device housing and any circuits therein from electromagnetic interference. A lead system to transmit and receive signals between a heart and the primary device housing. A switch places the control circuitry into a fixed-rate mode of operation. A changing magnetic field sensor to sense a change in magnetic field around the primary housing. The switch places the control circuitry into a fixed-rate mode of operation when the changing magnetic field sensor senses a predetermined encoded changing magnetic field.

In another embodiment of the present invention, a method prevents a cardiac assist system from failing during magnetic resonance imaging. A magnetic-resonance imaging system determines a quiet period for a cardiac assist system. Upon making this determination, the magnetic-resonance imaging system locks the timing of a magnetic resonance imaging pulse to occur during a quiet period of the cardiac assist system.

In an eighth embodiment of the present invention, a cardiac assist system is constructed of a primary device housing having a control circuit therein. A shielding is formed around the primary device housing to shield the primary device housing and any circuits therein from electromagnetic interference. A lead system to transmit and receive signals between a heart and the primary device housing. A switch places the control circuitry into a fixed-rate mode of operation. An acoustic sensor senses a predetermined acoustic signal, and the switch places the control circuitry into a fixed-rate mode of operation when the acoustic sensor senses the predetermined acoustic signal.

In a ninth embodiment of the present invention, a cardiac assist system is constructed of a primary device housing having a control circuit therein. A shielding is formed around the primary device housing to shield the primary device housing and any circuits therein from electromagnetic interference. A lead system to transmit and receive signals between a heart and the primary device housing. A switch places the control circuitry into a fixed-rate mode of operation. A near infrared sensor senses a predetermined near infrared signal. The switch places the control circuitry into a fixed-rate mode of operation when the near infrared sensor senses the predetermined near infrared signal.

The present invention also contemplates an electromagnetic radiation immune tissue invasive stimulation system that includes a photonic lead having a proximal end and a distal end; a light source, in the proximal end of the photonic lead, to produce a first light having a first wavelength; a wave-guide between the proximal end and distal end of the photonic lead; a distal sensor, in the distal end of the photonic lead, to convert the first light into electrical energy into control signals; an electrical energy storage device to store electrical energy; and a control circuit, in response to the control signals, to cause a portion of the stored electrical energy to be delivered to a predetermined tissue region. In this embodiment, the predetermined tissue region may be, for example, a region of the spinal cord, a region of the brain, a region associated with a deep brain structure, the vagal nerve, peripheral nerves that innervate muscles, sacral nerve roots to elicit functional contraction of muscles innervated by the sacral nerve roots, sacral nerve roots associated with bladder function, a region of the cochlea, a region of the stomach, or the hypoglossal nerve.

The present invention also contemplates an electromagnetic radiation immune tissue invasive sensing system that includes a photonic lead having a proximal end and a distal end; a light source, in the proximal end of the photonic lead, to produce a first light having a first wavelength; a wave-guide between the proximal end and distal end of the photonic lead; a distal sensor, in the distal end of the photonic lead, to convert the first light into electrical energy into control signals; an electrical energy storage device to store electrical energy; and a bio-sensor, in the distal end of the photonic lead, to sense a characteristic of a predetermined tissue region. The light source, in the proximal end of the photonic lead, produces a second light having a second wavelength. The distal sensor, in the distal end of the photonic lead and responsive to the bio-sensor, reflects the second light back the proximal end of the photonic lead such that a characteristic of the second light is modulated to encode the sensed characteristic of the predetermined tissue region. In this embodiment, the sensed characteristic may be, for example, an ECG, an EKG, an esophageal ECG, a level of oxygen, blood pressure, intracranial pressure, or temperature.

The present invention also contemplates an electromagnetic radiation immune sensing system that includes a photonic lead having a proximal end and a distal end; a light source, in the proximal end of the photonic lead, to produce a first light having a first wavelength and a second light having a second wavelength; a wave-guide between the proximal end and distal end of the photonic lead; a bio-sensor, in the distal end of the photonic lead, to measure changes in an electric field located outside a body, the electric field being generated by the shifting voltages on a body's skin surface; and a distal sensor, in the distal end of the photonic lead, to convert the first light into electrical energy and, responsive to the bio-sensor, to reflect the second light back the proximal end of the photonic lead such that a characteristic of the second light is modulated to encode the measured changes in the electric field. In this embodiment, the measured electric field may correspond to an ECG signal. Also in this embodiment, the bio-sensor has impedance higher than an impedance of an air gap between the bio-sensor and the body.

While various examples and embodiments of the present invention have been shown and described, it will be appreciated by those skilled in the art that the spirit and scope of the present invention are not limited to the specific description and drawings herein, but extend to various modifications and changes all as set forth in the following claims.

What is claimed is:

1. A cardiac assist system, comprising:
a primary device housing;
said primary device housing having a control circuit therein;
an optical-electrical lead system to transmit and receive signals between a heart and said primary device housing;
a shielding formed around said optical-electrical lead system to shield said optical-electrical lead system from electromagnetic interference; and
a biocompatible material formed around said shielding.

2. The cardiac assist system as claimed in claim 1, wherein said shielding is a metallic sheath to shield said optical-electrical lead system from electromagnetic interference.

3. The cardiac assist system as claimed in claim 1, wherein said shielding is a carbon composite sheath to shield said optical-electrical lead system from electromagnetic interference.

4. The cardiac assist system as claimed in claim 1, wherein said shielding is a polymer composite sheath to shield said optical-electrical lead system from electromagnetic interference.

5. The cardiac assist system as claimed in claim 1, wherein said bio compatible material is a non-permeable diffilsion resistant biocompatible material.

6. The cardiac assist system as claimed in claim 1, wherein said optical-electrical lead system includes a fiber optic based communication system.

7. The cardiac assist system as claimed in claim 6, wherein said fiber optic communication system contains at least one channel within a multi-fiber optic bundle.

8. The cardiac assist system as claimed in claim 1, wherein said optical-electrical lead system includes a plurality of electrical leads.

9. The cardiac assist system as claimed in claim 8, wherein an electrode located on an end of an electrical lead has an anti-antenna geometrical shape, said anti-antenna geometrical shape preventing said electrode from picking up and conducting stray electromagnetic interference.

10. The cardiac assist system as claimed in claim 8, wherein said electrical leads are unipolar leads.

11. The cardiac assist system as claimed in claim 8, wherein said electrical leads are bipolar leads.

12. The cardiac assist system as claimed in claim 8, wherein said electrical leads are a combination of unipolar and bipolar leads.

13. A tissue invasive device, comprising:
a primary device housing;
said primary device housing having a control circuit therein;
an optical-electrical lead system to transmit and receive signals between a selected tissue region and said primary device housing;
a shielding formed around said optical-electrical lead system to shield said optical-electrical lead system from electromagnetic interference; and
a biocompatible material formed around said shielding.

14. The tissue invasive device as claimed in claim 13, wherein said shielding is a metallic sheath to shield said optical-electrical lead system from electromagnetic interference.

15. The tissue invasive device as claimed in claim 13, wherein said shielding is a carbon composite sheath to shield said optical-electrical lead system from electromagnetic interference.

16. The tissue invasive device as claimed in claim 13, wherein said shielding is a polymer composite sheath to shield said optical-electrical lead system from electromagnetic interference.

17. The tissue invasive device as claimed in claim 13, wherein said biocompatible material is a non-permeable diffusion resistant biocompatible material.

18. The tissue invasive device as claimed in claim 13, wherein said optical-electrical lead system includes a fiber optic based communication system.

19. The tissue invasive device as claimed in claim 18, wherein said fiber optic communication system contains at least one channel within a multi-fiber optic bundle.

20. The tissue invasive device as claimed in claim 13, wherein said optical-electrical lead system includes a plurality of electrical leads.

21. The tissue invasive device as claimed in claim 20, wherein an electrode located on an end of an electrical lead has an anti-antenna geometrical shape, said anti-antenna geometrical shape preventing said electrode from picking up and conducting stray electromagnetic interference.

22. The tissue invasive device as claimed in claim 20, wherein said electrical are unipolar leads.

23. The tissue invasive device as claimed in claim 20, wherein said electrical leads are bipolar leads.

24. The tissue invasive device as claimed in claim 20, wherein said electrical leads are a combination of unipolar and bipolar leads.

* * * * *